(12) United States Patent
Yoshimura et al.

(10) Patent No.: US 7,855,076 B2
(45) Date of Patent: Dec. 21, 2010

(54) USE OF DISCOIDIN DOMAIN RECEPTOR 1 (DDR1) AND AGENTS THAT AFFECT THE DDR1/COLLAGEN PATHWAY

(75) Inventors: Teizo Yoshimura, Frederick, MD (US); Hidenobu Kamohara, Kumamoto (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 552 days.

(21) Appl. No.: 10/507,385

(22) PCT Filed: Dec. 11, 2002

(86) PCT No.: PCT/US02/39793

§ 371 (c)(1),
(2), (4) Date: Sep. 9, 2004

(87) PCT Pub. No.: WO03/082328

PCT Pub. Date: Oct. 9, 2003

(65) Prior Publication Data

US 2005/0118170 A1 Jun. 2, 2005

Related U.S. Application Data

(60) Provisional application No. 60/363,734, filed on Mar. 12, 2002, provisional application No. 60/380,978, filed on May 15, 2002, provisional application No. 60/419,179, filed on Oct. 16, 2002.

(51) Int. Cl.
*C12N 5/00* (2006.01)
*C12N 5/02* (2006.01)
(52) U.S. Cl. .................. 435/377; 435/355; 435/372; 435/385; 435/386
(58) Field of Classification Search .............. 435/377, 435/355, 372, 385, 386
See application file for complete search history.

(56) References Cited

U.S. PATENT DOCUMENTS

| 6,022,694 | A | 2/2000 | Radziejewski et al. | |
|---|---|---|---|---|
| 2003/0148316 | A1* | 8/2003 | Lipford et al. | 435/6 |

FOREIGN PATENT DOCUMENTS

| WO | 98/34954 | 8/1998 |
|---|---|---|

OTHER PUBLICATIONS

Clontech pLXSN vector information. Gene Bank Accession No. M28248.*
Clontech pLXSN vector information. Gene Bank Accession No. M28248 2001.*
Kamohara et al., "Discoidin domain receptor 1 isoform-a (DDR1a) promotes migration of leukocytes in three-dimensional collage lattices," *The FASEB Journal* express article 10.1096/fj.01-0359fje, http://www.fasebj.org/cgi/reprint/01-0359fjev1.pdf, published online Oct. 15, 2001.

Banchereau et al., "Dendritic cells as vectors for therapy," *Cell* 106:271-274, 2001.

Bhatt et al., "Discoidin domain receptor 1 functions in axon extension of cerebellar granule neurons," *Genes & Dev.* 14:2216-2228, 2000.

Brand et al., "Influence of extracellular matrix proteins on the development of cultured human dendritic cells," *Eur. J Immunol.* 28:1673-1680, 1998.

Curat et al., "Mapping of epitopes in discoidin domain receptor 1 critical for collagen binding," *J. Biol. Chem.* 276:45952-45958, 2001.

Jacob et al., "Influence of non-enzymatically glycated collagen on monocyte-macrophage differentiation," *Artherosclerosis* 159:333-341, 2001a.

Jacob et al., "Monocyte-macrophage differentiation in three dimensional collagen lattice," *Biochimica et Biophysica Acta* 1540:50-58, 2001b.

Jönsson et al., "Repression of Wnt-5a impairs DDR1 phosphorylation and modifies adhesion and migration of mammary cells," *J. Cell Sci.* 114:2043-2053, 2001.

Kamohara et al., "Discoidin domain receptor 1 isoform-a (DDR1a) promotes migration of leukocytes in three-dimensional collage lattices," *FASEB J.* 15(14):2724-2726, 2001.

Lapteva et al., "Profiling of genes expressed in human monocytes and monocyte-derived dendritic cells using cDNA expression array," *British Journal of Haematology* 114:191- 197, 2001.

L'Hôte et al., "Functional analysis of discoidin domain receptor 1: effect of adhesion on DDR1 phsophorylation," *FASEB J.* 16:234-236, 2002.

Lu et al., "Propagation of dendritic cell progenitors from normal mouse liver using granulocyte/macrophage colony-stimulating factor and their maturational development in the presence of type-1 collagen," *J. Exp. Med.* 179:1823-1834, 1994.

Mahnke et al., "Interaction of murine dendritic cells with collagen up-regulates allostimulatory capacity, surface expression of heat stable antigen, and release of cytokines," *Journal of Leukocyte Biology* 60:465-472, 1996.

Matsuyama et al., "Collagen-activation of discoidin domain receptor 1 isoform b (DDR1b) transduces signals that promote differentiation to macrophages and chemokine production in the human monocytic leukemia cell line, THP-1." Abstract for the 2002 Gordon conference (2002a).

(Continued)

*Primary Examiner*—Maria Leavitt
(74) *Attorney, Agent, or Firm*—Klarquist Sparkman, LLP.

(57) ABSTRACT

The disclosure provides methods of modulating the activity of DDR1. Methods for screening for agents that activate DDR1 are disclosed. Methods for inducing the maturation of immature macrophages and immature dendritic cells are also disclosed. In addition, methods for increasing neutrophil activation using a DDR1 activating agent, and methods for increasing leukocyte migration using a DDR1 activating agent, are provided.

26 Claims, 9 Drawing Sheets

OTHER PUBLICATIONS

Matsuyama et al., "Discoidin domain receptor 1 (DDR1) plays a role in migration and differentiation of leukocytes in a tissue microenvironment." Abstract for 2002 AAI meeting (2002b).

Nemoto et al., "Overexpression of protein tyrosine kinases in human esophageal cancer," *Pathobiology* 65(4):195-203, 1997 (abstract only).

Sakuma et al., "Receptor protein tyrosine kinase *DDR* is up-regulated by p53 protein," *FEBS Letters* 398:165-169, 1996.

Vogel et al., "Discoidin domain receptor 1 tyrosine kinase has an essential role in mammary gland development," *Molecular and Cellular Biology* 21(8):2906-2917, Apr. 2001.

Vogel et al., "Discoidin Domain Receptor 1 Is Activated Independently of $\beta_1$ Integrin," *J. Biol. Chem.* 275(8):5779-5784, 2000.

Vogel, "Discoidin domain receptors: structural relations and functional implications," *FASEB J.* 13:S77-S82, 1999 Supplement.

Vogel et al., "The discoidin domain receptor tyrosine kinases are activated by collagen," *Molecular Cell* 1:13-23, Dec. 1997.

\* cited by examiner

SEQUENCE LISTING

<160> NUMBER OF SEQ ID NOS: 16

<210> SEQ ID NO 1
<211> LENGTH: 6
<212> TYPE: PRT
<213> ORGANISM: Artificial sequence
<220> FEATURE:
<223> OTHER INFORMATION: concensus binding motif
<220> FEATURE:
<221> NAME/KEY: MISC_FEATURE
<222> LOCATION: (2)..(2)
<223> OTHER INFORMATION: Xaa is unknown
<220> FEATURE:
<221> NAME/KEY: MISC_FEATURE
<222> LOCATION: (2)..(2)
<223> OTHER INFORMATION: Xaa is unknown or other
<220> FEATURE:
<221> NAME/KEY: MISC_FEATURE
<222> LOCATION: (5)..(5)
<223> OTHER INFORMATION: Xaa is unknown

<400> SEQUENCE: 1

Leu Xaa Asn Pro Xaa Tyr
1               5

<210> SEQ ID NO 2
<211> LENGTH: 20
<212> TYPE: DNA
<213> ORGANISM: Artificial sequence
<220> FEATURE:
<223> OTHER INFORMATION: sense primer

<400> SEQUENCE: 2
ctttactgct gctgctcttg                                              20

<210> SEQ ID NO 3
<211> LENGTH: 20
<212> TYPE: DNA
<213> ORGANISM: Artificial sequence
<220> FEATURE:
<223> OTHER INFORMATION: antisense primer

<400> SEQUENCE: 3
ttgctccatc ccacatagtc                                              20

<210> SEQ ID NO 4
<211> LENGTH: 20
<212> TYPE: DNA
<213> ORGANISM: Artificial sequence
<220> FEATURE:
<223> OTHER INFORMATION: sense primer

<400> SEQUENCE: 4
gctcctgctg ctcatcattg                                              20

<210> SEQ ID NO 5
<211> LENGTH: 20
<212> TYPE: DNA
<213> ORGANISM: Artificial sequence
<220> FEATURE:
<223> OTHER INFORMATION: antisense primer

<400> SEQUENCE: 5 taatgggga cgctgttctg                                               20

<210> SEQ ID NO 6

```
<211> LENGTH: 12
<212> TYPE: PRT
<213> ORGANISM: Artificial sequence
<220> FEATURE:
<223> OTHER INFORMATION: synthetic peptide

<400> SEQUENCE: 6

Cys Val Pro Asn Gly Ser Ala Tyr Ser Gly Asp Tyr
1               5                   10

<210> SEQ ID NO 7
<211> LENGTH: 17
<212> TYPE: PRT
<213> ORGANISM: Artificial sequence
<220> FEATURE:
<223> OTHER INFORMATION: synthetic peptide

<400> SEQUENCE: 7

Cys Ala Arg Pro Pro Arg Gly Pro Gly Pro Pro Thr Pro Ala Trp Ala
1               5                   10                  15

Lys

<210> SEQ ID NO 8
<211> LENGTH: 17
<212> TYPE: PRT
<213> ORGANISM: Artificial sequence
<220> FEATURE:
<223> OTHER INFORMATION: synthetic peptide

<400> SEQUENCE: 8

Pro Arg Gly Pro Gly Pro Pro Thr Pro Ala Trp Ala Lys Pro Thr Asn
1               5                   10                  15

Cys

<210> SEQ ID NO 9
<211> LENGTH: 20
<212> TYPE: DNA
<213> ORGANISM: Artificial sequence
<220> FEATURE:
<223> OTHER INFORMATION: forward PCR primer

<400> SEQUENCE: 9
tttctgggca cccgcctcac                                              20

<210> SEQ ID NO 10
<211> LENGTH: 20
<212> TYPE: DNA
<213> ORGANISM: Artificial sequence
<220> FEATURE:
<223> OTHER INFORMATION: reverse PCR primer

<400> SEQUENCE: 10
ctgggggaag gtggctgaga                                              20

<210> SEQ ID NO 11
<211> LENGTH: 18
<212> TYPE: DNA
<213> ORGANISM: Artificial sequence
<220> FEATURE:
<223> OTHER INFORMATION: forward primer

<400> SEQUENCE: 11
cggatttggt cgtattgg                                                18

<210> SEQ ID NO 12
```

-continued

```
<211> LENGTH: 18
<212> TYPE: DNA
<213> ORGANISM: Artificial sequence
<220> FEATURE:
<223> OTHER INFORMATION: reverse primer

<400> SEQUENCE: 12
tcctggaaga tggtgatg                                                 18

<210> SEQ ID NO 13
<211> LENGTH: 25
<212> TYPE: DNA
<213> ORGANISM: Artificial sequence
<220> FEATURE:
<223> OTHER INFORMATION: sense primer

<400> SEQUENCE: 13
cgtatggcag gacaaatgct tcttc                                         25

<210> SEQ ID NO 14
<211> LENGTH: 21
<212> TYPE: DNA
<213> ORGANISM: Artificial sequence
<220> FEATURE:
<223> OTHER INFORMATION: antisense primer

<400> SEQUENCE: 14
ttccctccag gctgccatga g                                             21

<210> SEQ ID NO 15
<211> LENGTH: 22
<212> TYPE: DNA
<213> ORGANISM: Artificial sequence
<220> FEATURE:
<223> OTHER INFORMATION: oligonucleotide probe

<400> SEQUENCE: 15
agttgagggg actttcccag gc                                            22

<210> SEQ ID NO 16
<211> LENGTH: 20
<212> TYPE: DNA
<213> ORGANISM: Artificial sequence
<220> FEATURE:
<223> OTHER INFORMATION: oligonucleotide probe

<400> SEQUENCE: 16
agagtgggaa tttccactca                                               20
```

USE OF DISCOIDIN DOMAIN RECEPTOR 1 (DDR1) AND AGENTS THAT AFFECT THE DDR1/COLLAGEN PATHWAY

CROSS-REFERENCE TO RELATED APPLICATIONS

This is the §371, U.S. National Stage of International Application No. PCT/US02/39793, filed Dec. 11, 2002, which was published in English under PCT Article 21(2), which in turn claims the benefit of U.S. Provisional Application No. 60/363,734, filed Mar. 12, 2002, U.S. Provisional Application No. 60/380,978, filed May 15, 2002, and U.S. Provisional Application No. 60/419,179, filed Oct. 16, 2002, all of which are incorporated by reference herein in their entirety.

FIELD

This application relates to the field of discoidin domain receptors (DDRs), specifically to the use of agents that affect the activation of DDRs, and that affect cellular processes such as dendritic cell maturation.

BACKGROUND

One of the hallmarks of the inflammatory reaction is the accumulation of leukocytes at sites of injury or infection. During an immune response, circulating blood monocytes traverse the endothelial monolayer and the basement membrane of a blood vessel to reach an inflammatory site. This transmigration requires a multistep process involving an interaction between leukocytes and endothelial cells. Once at the inflammatory site, the monocytes interact with a wide variety of substances that include cytokines and the components of the extracellular matrix (ECM), such as collagen. Monocytes are then stimulated to differentiate into macrophages or antigen-presenting dendritic cells (DCs).

DCs are pivotal antigen-presenting cells for initiation of an immune response. Indeed, dendritic cells provide the basis for the production of an effective immune response to a vaccine, particularly for antigens wherein conventional vaccination is inadequate. DCs are also important in the production of an immune response to tumor antigens. Components of the ECM, such as collagen, may be involved in regulating the maturation of DCs, and may alter the ability of DCs to present antigens to the other cells of the immune system.

Collagen, a major component of the ECM, is a ligand for the discoidin domain receptor (DDR) tyrosine kinases DDR1, and DDR2. DDRs are a subfamily of receptor tyrosine kinases that possess an extracellular domain related to the lectin discoidin, found in the slime mold *Dictyostelium discoideum*. All members of the subfamily share an approximately 160-amino acid-long amino terminal discoidin (DS) homology domain, a single transmembrane region, extended juxtamembrane region, and a catalytic tyrosine kinase domain. DDR1, appears in at least five isoforms, a, b, c, d, and e, which are generated by alternative splicing. The DDR1b isoform contains 37, additional amino acids in the juxtamembrane region, relative to the DDR1a isoform. Contained within the additional amino acids in DDR1b is the LXNPXY motif that corresponds to the consensus binding motif for the Shc phosphotyrosine binding (PTB) domain. Collagen activation of DDR1b induces the autophosphorylation of DDR1b at specific residues within the binding motif.

Although the biological function of DDR1, is unknown, its expression pattern has been analyzed in a variety of normal and malignant tissues. Northern blot and in situ hybridization analysis demonstrate that human DDR1, is expressed predominantly in epithelial cells, such as those in the kidney, lung, gastrointestinal tract and brain. Upregulated DDR1, expression has been detected in breast, ovarian, esophageal, and brain tumors, and has been demonstrated to be at least three-fold higher in tumor cells than in the adjacent, normal, epithelium. Thus, DDR1 activation may be involved in tumorigenesis.

DDR1, mutants and DDR1-null mice have been used to study the function of DDR1. DDR1-null mice lack DDR1, protein expression. These mice are born alive, but are small compared to their heterozygous littermates. The DDR1-null females show multiple reproductive defects, although the female DDR1-null mice that are successful at reproducing are unable to nourish their litters because the mammary gland epithelium fails to secrete milk.

Regulating the activation of DDR1, may be important for controlling cell growth and differentiation. Thus, there exists a need for identifying agents that regulate the activation of DDR1, and, in turn, regulate the activation of DDR1 downstream signaling molecules.

SUMMARY

It is disclosed herein that activation of DDR1, by a DDR1-activating agent induces the maturation of a dendritic cell precursor, for example a monocyte, into a macrophage or a dendritic cell. Contacting a dendritic cell precursor with an effective amount of an antigen, in addition to an effective amount of a DDR1-activating agent, can induce the maturation of the dendritic cell precursor into an antigen-presenting dendritic cell. Thus, the activation of DDR1, can enhance antigen presentation to T cells and enhance T cell responses in a subject.

The activation of DDR1, is disclosed herein to induce cytokine and/or chemokine production in DDR1-expressing cells, such as macrophages, dendritic cells, and neutrophils. Leukocyte migration is also enhanced by the activation of DDR1. Thus, DDR1-activating agents (i.e. DDR1, agonists) can be used to enhance an immune response in a subject. Alternatively, agents that inhibit DDR1, activation (i.e. DDR1, antagonists) can be used to reduce or inhibit an immune response in a subject.

A method is provided for screening for an agent that induces the maturation of an immature macrophage or dendritic cell into a macrophage or a dendritic cell, respectively. The method includes contacting a cell expressing the DDR1, with the agent to determine if the agent is capable of binding to the DDR1. An agent that specifically binds the DDR1, is selected, as binding indicates that the agent induces the maturation of a dendritic cell.

A method is also disclosed for producing a macrophage or a mature dendritic cell from an immature macrophage or an immature dendritic cell, respectively. The method includes contacting a immature dendritic cell or the immature macrphage with an agent that induces expression of DDR1b, thereby inducing maturation of the immature cell. In one embodiment, the monocyte or dendritic cell precursor is also contacted with an antigen for a time sufficient to allow the antigen to be presented on the macrophage or mature dendritic cell.

A method of decreasing expression of a cytokine or a chemokine in a subject is also disclosed. The method includes administering to the subject an agent that binds DDR1b, thereby decreasing the expression of the cytokine or the chemokine in the subject. In several, non-limiting examples, the cytokine is interleukin (IL)-1β, IL-10,, or granulocyte-macrophage-colony stimulating factor (GM-CSF). In several, non-limiting examples, the chemokine is monocyte chemoattractant protein (MCP)-1,, macrophage inflammatory protein-1α (MIP-1α), or IL-8.

A method is provided for screening for an agent that activates DDR1b. The method includes contacting a cell that expresses DDR1b with the agent and determining if expression of a cytokine or a chemokine by the cell is induced. Induction of the expression of the cytokine or the chemokine indicates that the agent activates DDR1b. In several, non-limiting examples, the cytokine is IL-1β, IL-10, or GM-CSF. In several, non-limiting examples, the chemokine is MCP-1,, MIP-1α, or IL-8.

A method is provided for activating leukocyte migration. The method includes contacting a leukocyte with an antibody that specifically binds and activates DDR1a, thereby inducing migration of the leukoctye.

A method of inhibiting leukocyte migration is also provided. The method includes contacting a leukocyte with an antibody that specifically binds and prevents DDR1a activation, thereby inhibiting leukocyte migration.

The foregoing and other features and advantages will become more apparent from the following detailed description of several embodiments, which proceeds with reference to the accompanying figures.

BRIEF DESCRIPTION OF THE FIGURES

In FIG. 3A, results are shown from experiments where inner wells and outer wells were separated by a membrane only. Chambers were incubated at 37° C. for 3 hours. In FIG. 3B, results are shown from experiments where approximately 3 mm of collagen lattice was created above the membrane. Chambers were incubated at 37° C. for 8 hours. The number of migrated cells was counted in each 400× magnified field. The results were presented as migration index denoting the fold increase of cell migration over control (the number of migrated parental cells=1). Data are representative of three experiments with two independent clones overexpressing either DDR1, a or DDR1b.

SEQUENCE LISTING

Figure 1:
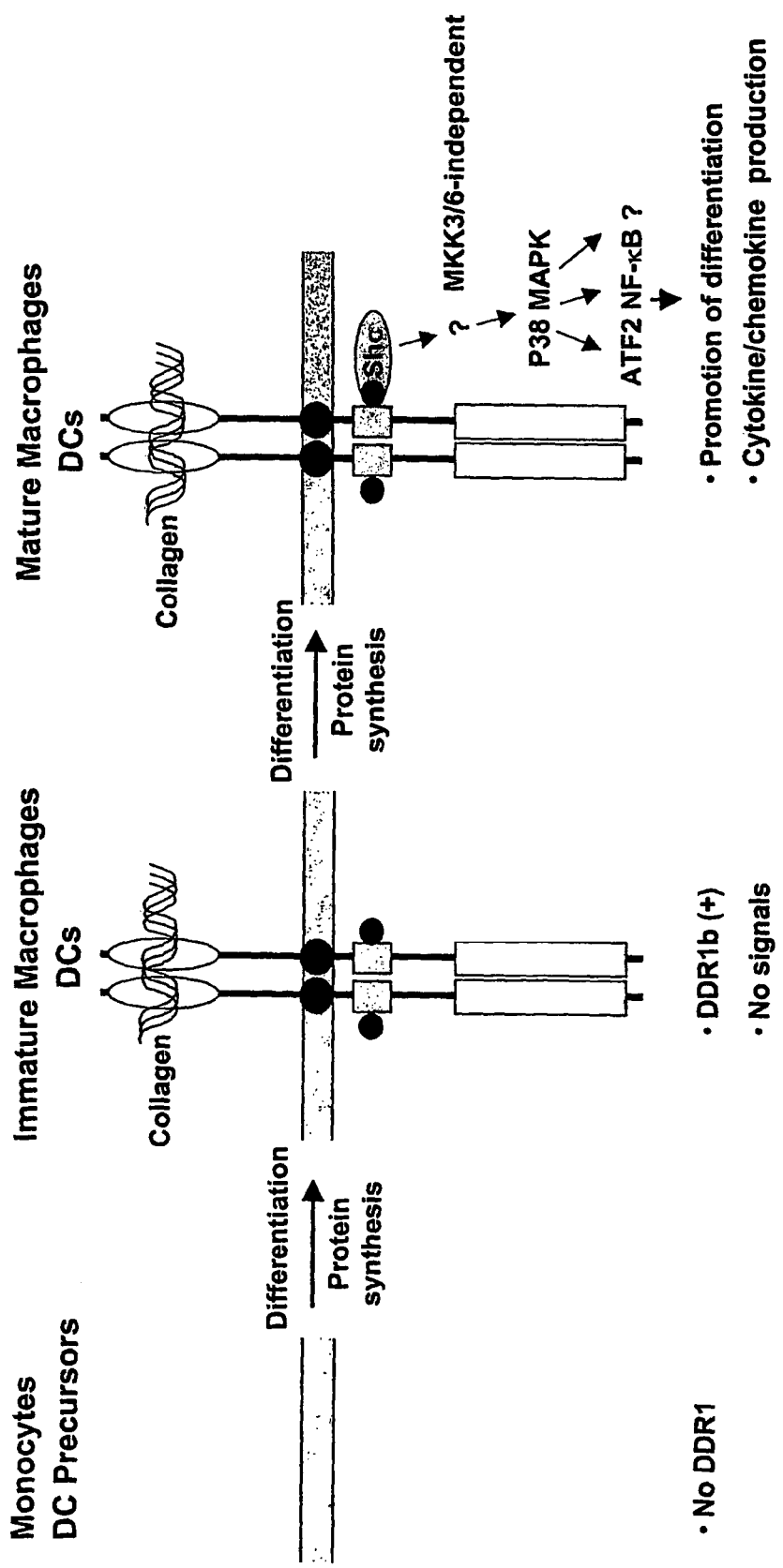
FIG. 1 is a schematic drawing of the effect of DDR1, expression on macrophage and DC maturation.

The nucleic and amino acid sequences listed in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 is the LXNPXY motif that corresponds to the consensus binding motif for the Shc phosphotyrosine binding (PTB) domain.

SEQ ID NO: 2 is a sense primer corresponding to the nucleotide sequence between 68-87 of the trkE cDNA.

SEQ ID NO: 3 is the antisense primer corresponding to the sequence between nucleotides 805 and 824 of trkE cDNA.

SEQ ID NO: 4 is the DDR1 sense primer that recognizes exon 9.

SEQ ID NO: 5 is the DDR1 antisense primer that recognizes exon 12.

SEQ ID NO: 6 is a synthetic peptide.

SEQ ID NO: 7 is a synthetic peptide.

SEQ ID NO: 8 is a synthetic peptide.

SEQ ID NO: 9 is the CIITA forward reverse transcription-polymerase chain reaction (RT-PCR) primer.

SEQ ID NO: 10 is the CIITA reverse RT-PCR primer.

SEQ ID NO: 11 is the glyceraldehyde-3-phosphate dehydrogenase forward primer.

SEQ ID NO: 12 is the glyceraldehyde-3-phosphate dehydrogenase reverse primer.

SEQ ID NO: 13 is the IL-1β forward primer.

SEQ ID NO: 14 is the IL-1β reverse primer.

SEQ ID NO: 15 is an oligonucleotide probes corresponding to the NF-κB binding site of the Ig κ chain gene.

SEQ ID NO: 16 is an oligonucleotide probes corresponding to the NF-κB binding site of the MCP-1 gene.

DETAILED DESCRIPTION

1. Abbreviations

| Ab | antibody |
|---|---|
| BSA | bovine serum albumin |
| C | constant |
| CHX | cycloheximide |
| DC | dendritic cell |
| DDR | discoidin domain receptor |
| DMSO | dimethlysulfoxide |
| ECM | extracellular matrix |
| ELISA | enzyme-linked immunosorbent assay |
| EMSA | electrophoretic mobility shift assay |
| FACS | fluorescence activated cell sort |
| FCS | fetal calf serum |
| G-CSF | granulocyte-colony stimulating factor |
| GM-CSF | granulocyte-macrophage-colony stimulating factor |
| GM-macrophage | GM-CSF-induced macrophage |
| GST | glutathione-S-transferase |
| H | heavy |
| iDC | immature dendritic cell |
| IFN | interferon |
| Ig | immunoglobulin |
| IL | interleukin |
| KLH | keyhole limpet hemocyanin |
| L | light |
| LPS | lipopolysaccharide |
| MCP | monocyte chemoattractant protein |
| mDC | mature dendritic cell |
| MIP | macrophage inflammatory protein |
| MLR | mixed leukocyte reaction |

-continued

| PAGE | polyacrylamide gel electrophoresis |
|---|---|
| PBMC | peripheral blood mononuclear cell |
| PBS | phosphate buffered saline |
| PGA | protein G-agarose |
| PGS | protein G-Sepharose |
| PHA | Phytohemagglutinin |
| PI | propidium iodide |
| PMA | phorbol 12-myristate 13-acetate |
| PMN | polymorphonuclear leukocyte |
| PTB | phosphotyrosine binding |
| RT-PCR | reverse transcription-polymerase chain reaction |
| SDS | sodium dodecyl sulfate |
| TNF | tumor necrosis factor |

II. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Activation of Discoidin Domain Receptor 1 (DDR1): Stimulation of DDR1 by a DDR1 activating agent. Examples of DDR1 activating agents include DDR1 ligands, such as collagen, or other agents, such as an antibody, a small molecule, a chemical compound, a peptidomimetic or a protein. Activation of DDR1 results in the recruitment and phosphorylation of intracellular signaling molecules, such as, but not limited to, molecules of the p38 MAP kinase pathway. Activation of DDR1 also results in increased expression of cell surface markers including, but not limited to, CD80, CD83, CD86, or HLA-DR; increased migration of leukocytes in a three-dimensional collagen matrix; increased expression of allogenic mixed leukocyte reaction (MLR); maturation/differentiation of leukocytes; and increased cytokine/chemokine production by dendritic cells and leukocytes. Activation of DDR1 can be increased by contacting DDR1 with a DDR1 ligand or an agent that acts as an agonist of DDR1. Alternatively, activation of DDR1 can be decreased by contacting DDR1 with an agent that acts as an antagonist.

Activation of neutrophils: Stimulation of neutrophils with an agent that induces the neutrophils to change morphology or activity. In one embodiment, an activated neutophil releases increased levels of cytokines and/or chemokines, such as MCP-1.

Agent: Any substance, including, but not limited to, an antibody, chemical compound, small molecule, peptide mimetic, peptide or protein. An agent can increase or decrease DDR1 activation. An agent can be a DDR1 agonist or a DDR1 antagonist.

Animal: Living multi-cellular vertebrate organisms, a category that includes, for example, mammals and birds. The term mammal includes both human and non-human mammals. Similarly, the term "subject" includes both human and veterinary subjects, such as, but not limited to, dogs, cats, and farm animals.

Antibody: Immunoglobulin (Ig) molecules and immunologically active portions of Ig molecules, i.e., molecules that contain an antigen binding site which specifically binds (immunoreacts with) an antigen. In one embodiment the antigen is a DDR1. In specific non-limiting examples, the antigen is DDR1a or DDR1b. Polyclonal, monoclonal, chimeric, and humanized immunoglobulins are all antibody forms. The term "antibody" includes synthetic and genetically engineered variants of these immunoglobulins.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Chemokines: A molecule that affects cellular trafficking. Generic name of a family of pro-inflammatory activation-inducible cytokines. These proteins are mainly chemotactic for different cell types. Chemokines have molecular masses of 8-10 kDa and show approximately 20-50 percent sequence homology among each other at the protein level. The proteins also share common gene structures and tertiary structures. All chemokines possess a number of conserved cysteine residues involved in intramolecular disulfide bond formation. Two different subfamilies of chemokines are distinguished by the chromosomal locations of individual genes. Examples of chemokines include, but are not be limited to, monocyte chemoattractant protein-1 (MCP-1) and macrophage inflammatory protein-1α (MIP-1α).

Collagen: Any of a family of extracellular, closely related proteins occurring as a major component of connective tissue, giving it strength and flexibility. At least 14 types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, nonperiodic but structured networks. Collagen type I, II, I, IV, and V have been reported to activate DDR1 (Vogel, *FASEB J.* 13 (Suppl.) S77-S82, 1999).

Cytokines: Proteins made by cells that affect the behavior of other cells, such as lymphocytes and neutrophils. In one embodiment, a cytokine is a chemokine, a molecule that affects cellular trafficking. Cytokines include, but may not be limited to, MIP-β, interleukin (IL)-1β, IL-10, granulocyte-macrophage colony stimulating factor (GM-CSF), granulocyte colony stimulating factor (G-CSF), neurokinin, and tumor necrosis factor-alpha (TNF-α).

Dendritic cell (DC): Dendritic cells are the principle antigen presenting cells involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells. In one embodiment, a dendritic cell is a myleoid dendritic cell. Myeloid dendritic cells (e.g. monocytes) differentiate from dendritic cell precursors called "DC1" while plasmacytoid dendritic cells differentiate from dendritic cell precursors termed "DC2."

DCs are capable of evolving from immature, antigen-capturing cells to mature, antigen-presenting, T cell-priming cells, converting antigens into immunogens and expressing molecules such as cytokines, chemokines, co-stimulatory molecules and proteases to initiate an immune response.

DCs are derived from hematopoietic stem cells in the bone marrow and are widely distributed as immature cells within all tissues, particularly those that interface with the environment (e.g. skin, mucosal surfaces) and in lymphoid organs. Immature DCs are recruited to sites of inflammation in peripheral tissues following pathogen invasion. Chemokine responsiveness and chemokine receptor expression are essential components of the DC recruitment process to sites of inflammation and migration to lymphoid organs. "Immature" DCs may express DDR1 (FIG. 1) as well as the chemokine receptors CCR1, CCR2, CCR5, CCR6 and CXCR1. Immature DCs capture antigens by phagocytosis, macropinocytosis or via interaction with a variety of cell surface receptors and endocytosis. Internalization of foreign antigens can subsequently trigger their maturation and migration from peripheral tissues to lymphoid organs.

The ability of DCs to regulate immunity is dependent on DC maturation. A variety of factors can induce differentiation following antigen uptake and processing within DCs, including: contact with whole bacteria or bacterial-derived antigens (e.g. lipopolysaccharide, LPS), cytokines (e.g. TNF-α, IL-4, GM-CSF), ligation of select cell surface receptors (e.g. CD40) and viral products (e.g. double-stranded RNA). During their conversion from immature to mature cells, DCs undergo a number of phenotypical and functional changes. The process of DC maturation, in general, involves a redistribution of major histocompatibility complex (MHC) molecules from intracellular endocytic compartments to the DC surface, down-regulation of antigen internalization, an increase in the surface expression of co-stimulatory molecules, morphological changes (e.g. formation of dendrites), cytoskeleton re-organization, secretion of chemokines, cytokines and proteases, and surface expression of adhesion molecules and chemokine receptors. Mature DCs express DDR1, which, when contacted with the appropriate agent, is activated and transmits an intracellular signal via the p38 MAP kinase pathway (see FIG. 1, Example 4).

Dendritic Cell Precursor: Immature cells that can differentiate into dendritic cells. In one embodiment a dendritic cell precursor is a DC1 cell that differentiates into myeloid cells (e.g. monocytes). In other embodiments, a dendritic cell precursor is a DC1 cell that differentiates into a myeloid dendritic cell, or a monocyte that differentiates into a macrophage which, in turn, differentiates into a dendritic cell. A dendritic cell precursor can also be a DC2 cell that differentiates into a plasmacytoid dendritic cell. Myeloid dendritic cells and plasmacytoid dendritic cells are also dendritic cell precursors as they differentiate into mature dendritic cells. In one embodiment, dendritic cell precursors do not express DDR1 or express low levels of DDR1 while mature dendritic cells express high levels of DDR1.

Differentiation: The process by which cells become more specialized to perform biological functions, and differentiation is a property that is totally or partially lost by cells that have undergone malignant transformation. For example, dendritic cell precursors such as monocytes or plasmacytoid dendritic cells can differentiate (or mature) into dendritic cells under the influence of certain cytokines and growth factors. In one embodiment, a dendritic cell differentiates into a mature dendritic cell. Inducers of differentiation (differentiation agents) include TNF-α, LPS, PMA, and GM-CSF.

Discoidin Domain Receptor (DDR): A subfamily of receptor tyrosine kinases which possess an extracellular domain related to the lectin discoidin, found in the slime mold *Dictyostelium discoideum*. All members of the subfamily share the approximately 160-amino acid-long amino terminal discoidin homology domain followed by a single transmembrane region, and extended juxtamembrane region, and a catalytic tyrosine kinase domain.

Two receptor tyrosine kinases with discoidin homology have been cloned and are known as discoidin domain receptor (DDR) 1 and DDR2. DDR1 appears in five isoforms, a (Accession No. NM_013993), b (Accession No. NM_001954), c (Accession No. NM_013994), d (Accession No. AF353182), and e (Accession No. AF353183), which are generated by alternative splicing (all GenBank entries are incorporated by reference). The DDR1b isoform contains an additional 37, amino acids (exon 11) in the juxtamembrane region, relative to the DDR1a isoform, which contains the LXNPXY (SEQ ID NO: 1) motif that corresponds to the consensus binding motif for the Shc phosphotyrosine binding (PTB) domain. In the DDR1c isoform, another six amino acids are inserted just at the beginning of the kinase domain. DDR1d arises from the deletion of exons 11 and 12, whereas in DDR1e, the first half of exon 10 and all of exons 11 and 12 are deleted. DDR1d and DDR1e do not have a kinase domain.

Northern blot and in situ hybridization demonstrate that DDR1 and DDR2 are widely expressed in the organs and tissues in humans and mice, including brain, lung, kidney. DDR1 is also inducible in leukocytes, including polymorphonuclear leukocytes (PMN), monocytes and lymphocytes. DDRs may also be involved in tumorigenesis, as both DDR1a and DDR1b transcripts have been detected in various human tumors, particularly in primary breast tumors, as well as in ovarian, esophageal and pediatric brain tumors. Moreover, in situ hybridization studies demonstrate that DDR1 is expressed in the tumor cells, whereas DDR2 is expressed in the stromal cells surrounding the tumor. Various types of collagen bind to DDR1 and DDR2 and induce autophosphorylation of the receptors with delayed kinetics.

Discoidin domain receptor 1 signaling pathway: Interaction of DDR1 with a DDR1 activating agent, for example, a collagen molecule, or a part thereof, to form a collagen-DDR1 complex thereby activating a series of downstream regulatory pathways in the cell that affect the cell metabolism and cellular function. Pathways that can be activated by a DDR1 activating agent-DDR1 ineraction, such as a collagen-DDR1 interaction, include those that control gene expression, cell division, cytoskeletal architecture, cell metabolism, migration, cell-cell interaction, spatial positioning, extracellular matrix synthesis, degradation and remodeling, protein expression, and/or cell adhesion. The downstream regulatory pathways can include any number of downstream signaling molecules. In one embodiment, activation of a downstream regulatory pathway initiates the recruitment and phosphorylation of downstream signaling molecules. In one embodiment, the downstream signaling molecule p38 MAP kinase is activated in response to a collagen-DDR1 interaction. Another example of a downstream signaling molecule is Shc. In other embodiments, chemokines (for example IL-8, MCP-1 and MIP-1α), cytokines (for example GM-CSF, IL-1β) or cell surface proteins (for example HLA-DR, CD14, CD11c, CD40) are up-regulated.

Epitope: An antigenic determinant. Epitopes are particular chemical groups or peptide sequences on a molecule that are antigenic, i.e. that elicit a specific immune response. An antibody binds a particular antigenic epitope.

Granulocyte/macrophage colony-stimulating factor (GM-CSF): A factor which modulates the maturation and function of dendritic cells (Witmer-Pack et al., *J. Exp. Med.* 166:1484-98, 1987).

GM-CSF is a monomeric protein of 127 amino acids with two glycosylation sites. The protein is synthesized as a precursor of 144 amino acids, which included a hydrophobic secretory signal sequence at the amino terminal end. The human gene has a length of approximately 2.5 kb and contains four exons. The distance between the GM-CSF gene and the IL-3 gene is approximately 9 kb. The human GM-CSF gene maps to chromosome 5q22-31.

GM-CSF was isolated initially as a factor stimulating the growth of macrophage/granulocyte-containing colonies in soft agar cultures. GM-CSF is also involved in the growth and development of granulocyte and macrophage progenitor cells. It stimulates myeloblasts and monoblasts and triggers irreversible differentiation of these cells. GM-CSF synergizes with erythropoietin in the proliferation of erythroid and megakaryocytic progenitor cells.

GM-CSF has been used clinically for the physiological reconstitution of hematopoiesis in diseases characterized either by an aberrant maturation of blood cells or by a reduced production of leukocytes. The usual dose, route and schedules for GM-CSF are 5-10 micrograms/kg/day either by 4-6 hours intravenous infusion or by subcutaneous injection.

Immune cell: Any cell involved in a host defense mechanism. These can include, for example, dendritic cells (DC), T cells, B cells, natural killer cells, monocytes, mast cells, macrophages, antigen-presenting cells, basophils, eosinophils, and neutrophils.

Immune response: A response of a cell of the immune system, such as a monocyte, a macrophage, a DC, a neutrophil, a B cell, or a T cell, to a stimulus. In one embodiment, the immune response involves the phagocytosis of a microbe by a macrophage. In another embodiment, the response is specific for a particular antigen (an "antigen-specific response").

Infectious agent: An agent that can infect a subject, including, but not limited to, viruses, bacteria, and fungi.

Examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria*, sps (such as. *M tuberculosis, M avium, M intracellulare, M kansaii, M. gordonae*), *Staphylococcus aureus, Neisseria gonorrhoeae, Neisseria meningitidis, Listeria monocytogenes, Streptococcus pyogeites*, (Group A *Streptococcus*), *Streptococcus agalactiae*, (Group B *Strepto-*

*coccus*), *Streptococcus*, (*viridans*, group), *Streptococcus faecalis*, *Streptococcus bovis*, *Streptococcus*, (*anaerobic*, sps.), *Streptococcus pneuinoniae*, *pathogenic Campylobacter*, sp., *Enterococcus*, sp., *Haemophilus influenzae*, *Bacillus antracis*, *corynebacterium diphtheriae*, *corynebacterium*, sp., *Erysipelothrix rhusiopathiae*, *Clostridium perfringers*, *Clostridium tetani*, *Enterobacter aerogenes*, *Klebsiella pneumoniae*, *Pasturella multocida*, *Bacteroides*, sp., *Fusobacterium nucleatum*, *Streptobacillus moniliformis*, *Treponema pallidum*, *Treponema pertenue*, *Leptospira*,, and *Actinomyces israelli*.

Examples of infectious fungi include, but are not limited to, *Cryptococcus neoformans*, *Histoplasma capsulatum*, *Coccidioides immitis*, *Blastomyces dermatitidis*, *Chlamydia trachomatis*, *Candida albicans*.

Other infectious organisms (such as protists) include: *Plasmodium falciparum*, and *Toxoplasma gondii*.

Inflammation: When damage to tissue occurs, the body's response to the damage is usually inflammation. The damage can be due to trauma, lack of blood supply, hemorrhage, autoimmunity, transplanted exogenous tissue, or infection. This generalized response by the body includes the release of many components of the immune system (e.g., defensins, IL-1 and tumor necrosis factor), attraction of cells to the site of the damage, swelling of tissue due to the release of fluid, and other processes.

During the inflammatory processes, a variety of soluble factors are involved in leukocyte recruitment through increased expression of cellular adhesion molecules and chemoattraction. Many of these soluble mediators regulate the activation of both the resident cells (such as fibroblasts, endothelial cells, tissue macrophages, and mast cells) and newly recruited inflammatory cells (such as monocytes, lymphocytes, neutrophils, and eosinophils). In one embodiment, activated neutrophils release azurophilic granules that contain defensins.

Interferon-γ: A dimeric protein with subunits of 146 amino acids. The protein is glycosylated at two sites, and the pI is 8.3-8.5. Interferon (IFN)-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40-60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an enzyme-linked immunosorbent assay (ELISA) test that allows detection of individual cells producing IFN-γ. Minute amounts of IFN-γ can be detected indirectly by measuring IFN-γ-induced proteins such as Mx protein. The induction of the synthesis of IP-10 has been used also to measure IFN-γ concentrations. In addition, bioassays can be used to detect IFN-γ, such as an assay that employs induction of indoleamine 2,3-dioxygenase activity in 2D9 cells.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B cells and T cells.

Macrophage: A large white blood cell derived from monocytes (a subclass of mononuclear leukocytes). Properties include phagocytosis and antigen presentation to T cells. Macrophages may assume different morphologic forms. Some develop abundant cytoplasm and are called epithelioid cells because of their resemblance to epithelial cells of the skin. Macrophages can fuse to form multinucleate giant cells. Macrophages are not found in the bloodstream but at locations where body organs interface with the environment or the bloodstream. For example, in the lungs, spleen, bone marrow and liver.

Macrophages function as accessory cells in the recognition and activation phases of adaptive inmmune responses. Their function as accessory cells is to display antigen in a form that can be recognized by T cells. Macrophages also produce membrane and secreted proteins that serve as second signals for T cell activation. Macrophages also serve numerous roles in the effector phases of adaptive immune responses. These cells phagocytose microbes and produce cytokines that recruit and activate other inflammatory cells.

Immature macrophages can be induced to differentiate and mature into mature macrophages or dendritic cells. Both immature and mature macrophages express DDR1 (FIG. 1).

Maturation: The process in which an immature cell, changes in form or function to become a functionally mature cell. Inducers of maturation (e.g. differentiation agents) include TNF-α, LPS, PMA, and GM-CSF. In one embodiment, a monocyte matures into a macrophage. In another embodiment, a dendritic cell precursor matures into a dendritic cell.

Monocyte: A white blood cell which can ingest dead or damaged cells (through phagocytosis) and provide immunological defences against many infectious organisms. Monocytes migrate into tissues and differentiate into macrophages. In one embodiment, monocytes express low levels of DDR1. In another embodiment, monocytes do not express DDR1 (FIG. 1).

Neoplasm: An abnormal cellular proliferation, which includes benign and malignant tumors, as well as other proliferative disorders.

Neutrophil: A polymorphonuclear (PMN) cell. A granular leukocyte that will stain with neutral dyes and eosin and which has a multi-lobed, irregular nucleus. A type of white blood cell which is most commonly found in the body and which is formed in the bone marrow. Neutrophils have the properties of chemotaxis, adherence to immune complexes, and phagocytosis. In one embodiment, neutrophils express DDR1.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. The promoter can be an inducible promoter or a constitutive promoter. Generally, operably linked DNA sequences are contiguous and, where necessary to join two protein coding regions, in the same reading frame.

Peptide mimetics: Structures that serve as substitutes for peptides in interactions between molecules. Peptide mimetics include synthetic structures that may or may not contain amino acids and/or peptide bonds but which retain structural and functional features of a peptide, or enhancer or inhibitor of DDR Pharmaceutical agent or drug: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

A "therapeutically effective amount" is a quantity of a specific substance sufficient to achieve a desired effect in a subject being treated. For instance, this can be the amount necessary to inhibit viral, fungal, or bacterial replication or to measurably alter symptoms of the viral, fungal, or bacterial infection. When administered to a subject, a dosage will generally be used that will achieve target tissue concentrations (for example, in lymphocytes) that has been shown to achieve a desired in vitro effect.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A linear nucleotide sequence, including sequences of greater than 100 nucleotide bases in length.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as ADP-ribosylated proteins, ribosyl-proteins, and glycoproteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

Preventing or treating a disease: "Preventing" a disease refers to inhibiting the full development of a disease, for example in a person who is known to have a predisposition to a disease such as a chronic inflammatory disease. An example of a person with a known predisposition is someone with a history of inflammatory diseases in the family, or who has been exposed to factors that predispose the subject to a condition, such as atherosclerosis, rheumatoid arthritis, inflammatory bowel disease, or lung fibrosis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Small molecule: A small naturally occurring or chemically synthesized molecule, that is active in a subject. A small molecule can be a peptide molecule or a pharmaceutical agent. Some small molecules are steroid-like. A tyrosine kinase inhibitor is an example of a small molecule. Tyrosine kinase inhibitors include, but are not limited to, leflunomides, genistein, herbimycin A, 2-Hydroxy-5-(2,5-Dihydroxybenzylamino)-2-hydroxybenzoic acid, tyrphostin and STI 571 (Gleevec).

Tumor: A neoplasm that may be either malignant or non-malignant. Tumors of the same tissue type are primary tumors originating in a particular organ (such as breast, prostate, bladder or lung). Tumors of the same tissue type may be divided into tumor of different sub-types (a classic example being bronchogenic carcinomas (lung tumors) which can be an adenocarcinoma, small cell, squamous cell, or large cell tumor). Breast cancers, for example, can be divided histologically into scirrhous, infiltrative, papillary, ductal, medullary and lobular.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

Methods for Inducing DDR1 Expression

Discoidin domain receptors (DDR) are a subfamily of receptor tyrosine kinases that possess an extracellular domain related to the lectin discoidin, found in the slime mold *Dictyostelium discoideum*. All members of the subfamily share an approximately 160-amino acid-long amino terminal discoidin homology domain, a single transmembrane region, extended juxtamembrane region, and a catalytic tyrosine kinase domain. Two receptor tyrosine kinases with discoidin homology have been cloned and are known as DDR1 and DDR2. DDR1 appears in five isoforms, a, b, c, d, and e, which are generated by alternative splicing. Ligands for DDR1 have been identified, including collagen, which induce auto-phosphorylation of the DDR receptors.

A method is provided herein for inducing DDR1 expression. The method includes contacting a dendritic cell or a leukocyte with an agent that induces DDR1 expression (a DDR1-inducing agent), thereby inducing DDR1 expression. This method provides for increased leukocyte migration (e.g. neutrophil or lymphocyte migration, see the examples section below), increased cytokine and chemokine release from dendritic cells and leukocytes, increased cell surface marker expression on dendritic cells or leukocytes, and the phosphorylation and activation of the p38 MAP kinase signaling pathway in dendritic cells or leukocytes.

Specific, non-limiting, examples of DDR1-inducing agents include fetal calf serum (FCS), IFN-γ, IL-1β, TNF-α, phytohemagglutinin (PHA), or GM-CSF. Any combination of one or more DDR1-inducing agents can be used simultaneously or sequentially in order to induce DDR1 expression. In one embodiment, a dendritic cell or a leukocyte is contacted with two DDR1-inducing agents. In other embodiments, a dendritic cell or a leukocyte is contacted with three, four, five, or more DDR-1 inducing agents. A dendritic cell or a leukocyte can also be contacted with collagen, or at least one differentiation agent, in addition to at least one DDR1-inducing agent. In one specific, non-limiting example, a dendritic cell or a leukocyte is contacted with collagen and a differentiation agent, such as, but not limited to, TNF-α or LPS, in addition to at least one DDR1-inducing agent in order to induce DDR1 expression.

Leukocytes and dendritic cells can be obtained from bone marrow, peripheral blood, umbilical cord blood, or fetal blood by any means known to one of skill in the art. Specific, non-limiting, examples of leukocytes include PMN, peripheral blood mononuclear cells (PBMC), lymphocytes, neutrophils, and monocytes. The leukocytes induced to express DDR1 can be mature (differentiated) or immature cells. Dendritic cells can be dendritic cell precursors, immature DCs, or mature DCs.

Chemokines that are released from cells, such as dendritic cells and leukocytes, in response to a DDR1-inducing agent include, but are not limited to, IL-8, MCP-1, and MW-1α. Examples of cytokines that are released in elevated levels from cells in response to a DDR1-inducing agent include, but are not limited to, IL-6 and IL-1β. Cell surface proteins increased in response to a DDR1-inducing agent include, but are not limited to, HLA-DR, CD11c, CD14, CD40, CD80, CD83, or CD86.

Induction of DDR1 expression can be detected by any means known to one of skill in the art. In one embodiment, induction of DDR1 expression is detected by Western blot analysis. In other embodiments, DDR1 expression is detected by Northern blot analysis, ELISA, electrophoretic mobility shift assay (EMSA), RT-PCR, immunofluorescence, flow cytometry or in situ hybridization.

Methods are provided herein where dendritic cells and leukocytes can be induced in vitro to express DDR1. In one embodiment, dendritic cells and leukocytes induced in vitro to express DDR1 are cultured on plastic dishes. The plastic dishes can be coated or uncoated. In one specific, non-limiting, example, the dishes are coated with collagen. The dendritic cells and leukocytes can be cultured for any length of time before being exposed to the DDR1-inducing agent. For example, the dendritic cells and leukocytes can be cultured for about 0, 1, 2, 5, 10, 12, 16, 24, or more hours before being exposed to the DDR1-inducing agent. Alternatively, the dendritic cells and leukocytes can be cultured for about 1, 2, 3, 5, 7, 10, or more days before being exposed to the DDR1-inducing agent.

The amount of DDR1-inducing agent contacting the dendritic cells and leukocytes in vitro can vary. For example, in one embodiment, the incubation medium contains between about 1% and about 20% FCS. In other embodiments, the incubation medium contains between about 2% and about 15%, between about 5% and about 12%, or about 10% FCS.

Methods are also disclosed herein for inducing the expression of DDR1 in dendritic cells and leukocytes in vivo. The method includes administering a therapeutically effective amount of a DDR1-inducing agent to a subject, thereby inducing the expression of DDR1 in dendritic cells or leukocytes. The subject can be a mammal, for example a human. In one embodiment, inducing the expression of DDR1 in dendritic cells or leukocytes in a subject with a DDR1-inducing agent stimulates an immune response.

The DDR1-expressing dendritic cells or leukocytes generated by the methods disclosed herein can also be used for tumor immunotherapy. In one embodiment, DDR1-expressing leukocytes are generated to recognize and eliminate a cell expressing a tumor antigen. A therapeutically effective amount of DDR1-expressing leukocytes can be administered to a subject with a tumor that expresses the tumor antigen. In another embodiment, the DDR1-expressing leukocytes are administered in conjunction with a chemotherapeutic agent.

In one embodiment, dendritic cells and leukocytes are induced in vitro to express DDR1 and the resultant DDR-expressing dendritic cells or leukocytes are subsequently administered to a subject. In one embodiment, the subject suffers from a disease, for example a tumor. Thus, a therapeutically effective amount of DDR1-expressing dendritic cells or leukocytes, generated by contacting dendritic cells or leukocytes in vitro with a DDR1-inducing agent, can be administered to a subject in order to preferentially stimulate an immune response.

Methods for Inducing Dendritic Cell and Macrophage Maturation

A method is provided herein for generating mature dendritic cells or macrophages from immature precursor cells. The method includes contacting an immature dendritic cell or an immature macrophage with a DDR1-inducing agent and an agent that activates DDR1 (a DDR1-activating agent), thereby generating mature (differentiated) dendritic cells or macrophages. This method further provides for the enhancement of T cell responses by increasing dendritic cell maturation, and thus enhancing antigen presentation to T cells. The method of generating mature dendritic cells or macrophages from a dendritic cell precursor or a monocyte can be performed either in vitro or in vivo.

One of skill in the art can readily identify tissue sources of monocytes or dendritic cell precursors, such as fetal blood, peripheral blood, umbilical cord blood, or bone marrow. To increase the number of monocytes or dendritic cell precursor cells in animals, including humans, the subject can be treated with substances that stimulate hematopoiesis, such as stem cell factor, IL-3 or GM-CSF. One of skill in the art can readily identify the concentration of the cytokine of use. In one specific, non-limiting example, cytokines are present in concentrations ranging from about 25 to about 100 ng/ml, depending on the specific cytokine used. U.S. Pat. No. 5,994,126, discloses methods for isolating dendritic cell precursors and methods for increasing the number of dendritic cell precursors in a sample.

An immature dendritic cell or an immature macrophage can be contacted with a DDR1-activating agent simultaneously with, or sequentially with, a DDR1-inducing agent. Any combination of one or more DDR1-activating agents can be used with any combination of one or more DDR1-inducing agents. Specific, non-limiting examples of DDR1-activating agents include collagen and anti-DDR1 activating antibodies. Specific, non-limiting examples of DDR1-inducing agents include, but are not limited to, FCS, IFN-γ, IL-1β, TNF-α, PHA, or GM-CSF.

In one embodiment, a cell that does not express DDR1, for example a monocyte or a dendritic cell precursor, is contacted with a differentiation agent, in addition to a DDR-inducing agent and a DDR1-activating agent, thereby inducing the maturation or differentiation of a monocyte or a dendritic cell precursor into a mature, DDR1-expressing cell. Examples of differentiation agents include PMA, TNF-α, IL-4, LPS, and GM-CSF. Other examples of differentiation agents include agents that bind CD40, such as the CD40 ligand. Any combination of one or more differentiation agents can be used simultaneously in order to induce the maturation of a monocyte or a dendritic cell precursor. In several examples, two, three, four, five, or more differentiation agents are utilized.

In one specific, non-limiting example, a moncyte or a dendritic cell precursor is transfected with a nucleic acid encoding DDR1 operably linked to a promoter. The protein coding sequences for DDR1 are known (e.g. see Genbank for the sequences of DDR1a (Accession No. NM_013993), b (Accession No. NM_001954), c (Accession No. NM_013994), d (Accession No. AF353182), and e (Accession No. AF353183, all GenBank entries are incorporated by reference). The promoter can be a cell-type specific, tissue-specific, or inducible by external signals or agents. Both constitutive and inducible promoters, are included (see e.g. Bitter et al., *Methods in Enzymology* 153:516-544, 1987). For example, in a mammalian cell systems, promoters derived from the genome of mammalian cells (e.g., metallothionein promoter, immunoglobulin promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences encoding DDR1.

The promoter and the DDR1 coding sequence can be included in an expression vector. The expression vector can be any plasmid, virus or other vehicle known in the art that inlcudes nucleic acid sequences designed to promote the expression of a polypeptide that has been manipulated by insertion or incorporation of the DDR1 coding sequence. Expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codon An expression vector typically contains an origin of replication, a promoter, as well as specific genes which allow phenotypic selection of the transformed cells. Methods of expressing DNA sequences having eukaryotic or viral sequences in are well known in the art. Biologically functional viral and plasmid DNA vectors capable of expression and replication in a host are known in the art. Such vectors are used to incorporate DNA sequences of the invention.

A transfected cell is a cell into which (or into an ancestor of which) has been introduced, by means of recombinant DNA techniques, a DNA molecule encoding DDR1. Transfection of a host cell with recombinant DNA may be carried out by conventional techniques as are well known to those skilled in the art. For example, methods of transfection of DNA such as calcium phosphate co-precipitation, conventional mechanical procedures such as microinjection, electroporation, insertion of a plasmid encased in liposomes, or virus vectors may be used. Dendritic cell precursors and monocytes can also be cotransfected with DNA sequences encoding DDR1 and a second foreign DNA molecule encoding a selectable phenotype, such as the herpes simplex thymidine kinase gene.

Methods for generating mature dendritic cells and macrophages from immature macrophages or immature dendritic cells are thus disclosed herein. In one embodiment, the immature macrophages or immature dendritic cells express DDR1. The method includes contacting a DDR1-expressing cell, such as an immature macrophage or an immature dendritic cell, with an effective amount of a DDR1-activating agent, thereby inducing maturation of the cells. In one embodiment, an agent that enhances the maturation of a DDR1-expressing immature macrophage or a DDR1-expressing immature dendritic cell (for example, a differentiation agent) is administered simultaneously or sequentially with a DDR1-activating agent such as PMA, TNF-α, IL-4, LPS, and/or GM-CSF. In another embodiment, a DDR1-expressing cell, for example an immature macrophage or an immature dendritic cell, is contacted with an effective amount of a DDR1-activating agent in the absence of an additional agent.

In one embodiment, an immature dendritic cell or an immature macrophage is contacted with an effective amount of a DDR1-activating agent for a sufficient period of time to differentiate a mature dendritic cell or macrophage in vitro. In one specific, non-limiting example, peripheral blood mononuclear cells (PBMCs) are contacted with an effective amount of one or more agents that mimic the effect of DDR1 activation by collagen, for a sufficient period of time to differentiate into mature macrophages in vitro. In specific, non-limiting examples, a culture of isolated peripheral blood monocytes containing about $1 \times 10^5$ to about $1 \times 10^7$, about $1 \times 10^6$ to about $1 \times 10^7$, about $1 \times 10^6$ to about $5 \times 10^6$, or about $4 \times 10^6$ cells/ml are treated with an effective amount of a DDR1-activating agent in vitro. In one specific non-limiting example, the culture is maintained for at least one day. In another specific non-limiting example, the culture is maintained for about 1 to about 4 days. In another specific non-limiting example, the culture is maintained for about 1 to about 7 days.

The present disclosure also relates to methods for generating enriched populations of mature, antigen-presenting macrophages or dendritic cells that can function to present antigen to T cells. The method includes contacting an immature macrophage or an immature dendritic cell with an effective amount of a DDR1-activating agent and an effective amount of an antigen, thereby differentiating the cell into an antigen-presenting cell in vitro. The cells are contacted with the antigen for a time sufficient to allow the antigen to be internalized, processed, and presented by the mature macrophage or mature dendritic cell. In some embodiments, the cells are also contacted with a DDR1-inducing agent and/or a differentiation agent.

Antigens of interest include any immunogenic biomolecules, which can be produced by recombinant methods or isolated from natural sources. Exemplary antigens include, but are not limited to, epitopes or antigens from tumors, antigens from infectious agents (for example, viruses, parasites, fungi) or allergens. These antigens may be composed of protein, DNA, RNA, lipid, sugar, whole cell lysates, apoptotic cells, or any combination thereof.

The antigen can be delivered to the cells of interest via any method known in the art, including, but not limited to, pulsing the cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1, µg to about 100 µg of a selected antigen. An antigen preparation can also contain buffers, excipients, and preservatives, amongst other ingredients.

In one embodiment the immature macrophage or immature dendritic cell is contacted with an additional agent, such as a cytokine, to expand the number of cells in vitro, and then the cells are contacted with a DDR1-activating agent and the antigen. The cells can be contacted with the antigen and the DDR1-activating agent either sequentially or simultaneously.

In one specific, non-limiting example, mature macrophages or dendritic cells are obtained in vitro by culturing immature monocytes or immature dendritic cells with a DDR1-activating agent for about 12 to about 72 hours. In other embodiments, the mature macrophages or dendritic cells are contacted with antigen for a time sufficient to allow the antigen to be internalized, processed, and presented by the mature macrophages or dendritic cells, thereby producing antigen-presenting macrophages or dendritic cells.

One of skill in the art can readily identify mature macrophages, dendritic cells, antigen-presenting macrophages and antigen-presenting dendritic cells. These techniques include, but are not limited to, detection of specific antigens present on mature macrophages or dendritic cells with monoclonal antibodies and assays for mixed lymphocyte reactions.

In a one embodiment, the presence of mature macrophages or dendritic cells can be confirmed by the use of antibodies specific for various mature dendritic cell surface markers, such as CD80, CD83 and CD86. Among the specific monoclonal antibodies suitable for identifying mature macrophages or dendritic cells include, but are not limited to, CD11c, CD14, CD40, CD80, CD83, CD86, or HLA-DR. Typically, labeled antibodies specifically directed to the marker are used to identify the cell population. The antibodies can be conjugated to other compounds including, but not limited to, enzymes, magnetic beads, colloidal magnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals*, (1992-1994). The metal compounds that can be conjugated to the antibodies include, but are not limited to, ferritin, colloidal gold, and particularly, colloidal superparamagnetic beads.

Mature macrophages or dendritic cells may also be identified histologically, by assessing cell morphology such as, nuclear reorganization, vacuole formation, cytoplasmic enlargement, and membrane ruffling. In addition, one skilled in the art can assess typical mature dendritic cell morphology, including stellate shape and/or well defined veils.

The mature macrophage or dendritic cells generated by the methods disclosed herein can also be used for tumor immunotherapy. In one embodiment, mature antigen presenting cells are generated to present a tumor antigen. These macrophages or dendritic cells are then administered to a subject with a tumor that expresses the antigen. In another embodiment, the mature macrophages or dendritic cells are administered in conjunction with a chemotherapeutic agent.

Mature macrophages or dendritic cells generated by the methods disclosed herein can be administered to a subject. In one specific, non-limiting example, a therapeutically effective amount of the mature macrophages or dendritic cells is administered to a subject to preferentially stimulate immune responses that block allergic responses (e.g. interferon production).

Mature macrophages or dendritic cells can be used to produce activated T lymphocytes. The method includes contacting the mature macrophage or mature dendritic cell with a T lymphocyte in vitro, thereby producing an activated T lymphocyte. These T cells can be administered to a subject.

In another embodiment, mature macrophages or dendritic cells are administered to a subject to boost an immune response against another antigen. In one specific, non-limiting example, the antigen is from an infectious agent, including but not limited to, an antigen from a bacterium, virus, or fungus. The dendritic cells can be from the same subject (autologous) or can be from a different individual (heterologous).

A method is also disclosed herein for inducing the differentiation of monocytes or dendritic cell precursors in vivo. The method includes administering a therapeutically effective amount of a DDR1-activating agent to a subject, thereby inducing differentiation of monocytes or dendritic cell precursors into differentiated macrophages or dendritic cells in the subject. The subject can be any mammal, such as a primate. In one specific, non-limiting example, the subject is a human, but veterinary use is contemplated.

Mature dendritic cells and macrophages provided by the disclosed methods are of use for immunotherapy, such as in situations in which a host response to an antigen is suboptimal. Thus, in several embodiments, the methods disclosed herein are of use in augmenting a response to an antigen. In specific, non-limiting examples, the antigen is a tumor antigen (e.g. an antigen used in tumor immunotherapy), an antigen from an infectious agent, or an antigen of use in a vaccine.

Method of Inducing Cytokine/Chemokine Production

A method is provided herein for the induction of cytokines and/or chemokines from mature leukocytes or dendritic cells. The method includes contacting an immature macrophage, immature dendritic cell or a neutrophil with a DDR1-inducing agent and a DDR1-activating agent, thereby inducing the production of cytokines and/or chemokines. The method further provides for the induction of an inmmune response in a subject that results from increased cytokine or chemokine production by a macrophage, mature dendritic cell, or a neutrophil contacted with a DDR1-activating agent. The method of inducing cytokine and/or chemokine production from mature leukocytes or dendritic cells can be performed either in vitro or in vivo.

The present disclosure relates to methods for generating enriched populations of mature leukocytes, such as neutrophils or macrophages, or dendritic cells that can function to increase cytokine and/or chemokine production in response to a DDR1-activating agent. Examples of chemokines that can be increased in response to DDR1-activating agents include IL-8, MIP-1α, or MCP-1 production. Examples of cytokines that are increased in response to DDR1-activating agents include, for example, IL-1β, IL-10, IL-12, and TNF-α.

The method includes contacting a neutrophil, an immature macrophage, or an immature dendritic cell with an effective amount of a DDR1-inducing agent and a DDR1-activating agent, thereby inducing the production of cytokines and/or chemokines. In one embodiment, a DDR1-expressing immature macrophage, or a DDR1-expressing immature dendritic cell is contacted with an effective amount (such as a therapeutically effective amount) of a DDR1-activating agent, thereby inducing cytokine and/or chemokine production. In some embodiments, the immature macrophage or immature dendritic cells are also contacted with a differentiation agent.

Methods of Inhibiting Cell Migration and Cytokine/Chemokine Production

A method is provided herein for inhibiting leukocyte and dendritic cell migration. The method includes contacting a dendritic cell precursor or a leukocyte, for example a neutrophil or a monocyte, with an agent that inhibits the expression of DDR1 (DDR1-inhibiting agent), thereby preventing leukocyte or dendritic cell migration. The method of inhibiting DDR1 expression, by contacting a dendritic cell precursor or leukocyte with a DDR1-inhibiting agent, further provides for the inhibition of an immune response in a subject.

A DDR1-inhibiting agent can be a protein or a nucleic acid. In one embodiment, a DDR1-inhibiting agent is a substance, such as an antibody, a chemical compound, a small molecule, a peptide, a peptidomimetic or a protein, that targets the gene and inhibits DDR1 expression. The agent can bind regulatory regions of the gene, such as the enhancer or promoter regions, or the agent can bind the coding region of the gene, thereby inhibiting DDR1 expression.

In another embodiment, the reduction of DDR1 expression in a leukocyte or dendritic cell may be obtained by introducing into cells an antisense or other suppressive construct based on the DDR1 encoding sequence or flanking regions thereof. For antisense suppression, a nucleotide sequence from a DDR1 encoding sequence, e.g. all or a portion of the DDR1 cDNA or gene, is arranged in reverse orientation relative to the promoter sequence in the transformation vector. For suppression of the DDR1 gene, transcription of an antisense construct results in the production of RNA molecules that are the reverse complement of mRNA molecules transcribed from the endogenous DDR1 gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA. Expression of DDR1 can also be reduced using small inhibitory RNAs, for instance using techniques similar to those described previously (see, e.g., Tuschl et al., Genes Dev 13:3191-3197, 1999; Caplen et al., Proc. Natl. Acad. Sci. U.S.A. 98:9742-9747, 2001; and Elbashir et al., Nature 411:494-498, 2001).

Suppression of endogenous DDR1 expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

A method is also provided herein that includes contacting a DDR1-expressing dendritic cell or leukocyte, such as a macrophage or a neutrophil, with an agent that decreases the activation of DDR1 thereby preventing leukocyte or dendritic cell migration. In one embodiment, the agent that decreases DDR1 activation inhibits the activation of DDR1.

In one embodiment, the agent that decreases the activation of DDR1 inhibits collagen from binding to DDR1 thereby decreasing the activation of DDR1. In one specific, non-limiting example, the agent that decreases the activation of DDR1 is an anti-DDR1 antibody that recognizes, and binds to, an epitope in the DDR1 collagen-binding site, thereby blocking the binding of collagen to DDR1 and inhibiting DDR1 activation. In other specific, non-limiting examples, the agent that decreases the activation of DDR1 includes, but is not limited to, a small molecule, a peptide, peptide mimetic, a chemical compound or a protein, thereby decreasing, or inhibiting, the activation of DDR1. In one embodiment, the agent that decreases the activation of DDR1 such as an antibody, inhibits or decreases the activation of at least one member of the DDR1 downstream signaling pathway, such as Shc.

A method is also provided herein for reducing or inhibiting cytokine and/or chemokine production. The method includes contacting a dendritic cell precursor or leukocyte such as, but not limited to, a monocyte, a macrophage, or a neutrophil, with a DDR1-inhibiting agent, thereby reducing or preventing cytokine and/or chemokine production. The DDR1-inhibiting agent can decrease DDR1 activation, thereby reducing or inhibiting cytokine and/or chemokine production. In specific, non-limiting examples, the production of MCP-1 is reduced or is inhibited when a dendritic cell precursor or a leukocyte is contacted with a DDR1-inhibiting agent. In other specific, non-limiting examples the production of MIP-1α, IL-1β, or IL-8 is either decreased or inhibited when a dendritic cell precursor or a leukocyte is contacted with a DDR1-inhibiting agent.

An agent that decreases or inhibits DDR1 activation, thereby preventing leukocyte migration or cytokine/chemokine production, can be given to a cell alone or in combination with other agents, such as an agent that decreases DDR1 expression. These agents can be administered in vivo or in vitro. In one embodiment, a DDR1-expressing leukocyte or a DDR1-expressing dendritic cell is contacted with an agent that decreases DDR1 expression or inhibits DDR1 activation in vitro and the cell contacted with the agent is subsequently administered to a subject. In another embodiment, a subject is administered a therapeutically effective amount of an agent that decreases DDR1 expession or inhibits DDR1 activation in leukocytes or dendritic cells.

In one embodiment, inhibition of leukocyte migration or inhibition of cytokine and/or chemokine production is of use clinically in subjects suffering from a disease of the immune system, such as chronic inflammatory disease. Chronic inflammatory disease includes, but is not limited to, atherosclerosis, rheumatoid arthritis, and lung fibrosis. In another embodiment, the method disclosed herein is of use in decreasing an allergic response in a subject.

Agents that Affect DDR1 Activation

The use of agents is provided herein, wherein the agents affect DDR1 activation. The agent can be a DDR1-activating agent, or an agent that decreases DDR1 activation. DDR1-activating agents are of use in inducing the maturation of dendritic cells and macrophages and are also of use in inducing cytokine and/or chemokine production, and enhancing leukocyte and dendritic cell maturation, thereby inducing an immune response. Agents that decrease DDR1 activation are of use in decreasing cytokine and/or chemokine production and decreasing leukocyte and dendritic cell migration, thereby inhibiting an immune response.

DDR1 can be either the DDR1a isoform or the DDR1b isoform. DDR1-activating agents include, but are not limited to, collagen, anti-DDR1 antibodies, chemical compounds, peptide mimetics, peptides, proteins, or small molecules. Any combination of DDR1-activating agents can be used to activate DDR1. In one specific, non-limiting example, collagen binds DDR1 and activates DDR1. In another specific, non-limiting example, a DDR1-activating agent binds DDR1 and mimics collagen, thereby activating DDR1. Agents that mimic collagen can activate DDR1 to the same degree as collagen, or these agents can activate DDR1 to a greater, or a lesser, degree than collagen.

DDR1-activating agents can cause the recruitment and/or phosphorylation of molecules of the DDR1 signaling pathway. In one embodiment, a DDR1-activating agent contacts a DDR1-expressing cell, such as a leukocyte or dendritic cell, activates DDR1 and causes the recruitment and/or phosphorylation of DDR1 signaling molecules. DDR1 signaling molecules include, but are not limited to, DDR1 Shc, and molecules of the p38 MAP kinase pathway such as p38 MAP kinase. In another embodiment, a DDR1-activating agent contacts a DDR1-expressing cell, such as a leukocyte or dendritic cell, activates DDR1 and causes the up-regulation of cell surface markers. Up-regulated cell surface markers include, but are not limited to, CD11c, CD14, CD40, CD80, CD83, CD86, or HLA-DR. A DDR1-activating agent in contact with a DDR1-expressing cell can activate leukocytes, such as neutrophils or lymphocytes, and increase the migration of leukocytes, for example in a three-dimensional collagen matrix, or induce cytokine secretion by the leukocyte. A DDR1-activating agent in contact with a DDR1-expressing leukoctye or dendritic cell can also induce the maturation of immature leukoctyes and immature dendritic cells into mature macrophages and mature dendritic cells, and induce cytokine and/or chemokine production.

A change in DDR1 activation can be measured using any number of parameters. In one embodiment, a change in activation is measured by the increase or decrease in the level of proinflammatory cytokines or chemokines produced by the cell expressing DDR1. Specific, non-limiting examples of cytokines released at increased levels following DDR1 activation include, but are not limited to, IL-1β, IL-10, and IL-12. Specific, non-limiting examples of chemokines released at increased levels following DDR1 activation include, but are not limited to, IL-8 MCP-1 and MIP-1α. Techniques which measure changes in the level of proinflammatory cytokines and chemokines include, but are not limited to, Western blot analysis, Northern blot analysis, in situ hybridization, EMSA and ELISA.

In one specific, non-limiting example, the agent is an antibody. An antibody that affects DDR1 activation can be a polyclonal antibody, a monoclonal antibody, a chimeric antibody (for example, an antibody that contains the binding specificity of a murine antibody, but in which the remaining portions are of human origin) or a humanized monoclonal antibody. In one embodiment, an antibody can increase or decrease the activation of DDR1 by binding to, and thereby blocking, the collagen-binding site on the DDR1 molecule. An antibody can also affect the activation of DDR1 either increasing or decreasing the activation of DDR1 by binding a site (epitope) on DDR1. The epitope can be anywhere on the DDR1 including, but not limited to, the collagen-binding site. Without being bound by theory, in one example, the binding of the antibody to the epitope can alter the conformation of DDR1 in such as way as to increase or decrease the activation of the DDR1 molecule.

An antibody that has an effect on DDR activation can be an intact antibody or a fragment of an antibody that is capable of binding antigen or that is immunologically active. A naturally occurring antibody (e.g., IgG) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., *Nature* 341:544-546, 1989) which consists of a VH domain; and (v) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al., *Science* 242:423-426, 1988; and Huston et al., *Proc. Natl. Acad. Sci. U.S.A.*, 85:5879-5883, 1988) by recombinant methods. Such single chain antibodies, as well as dsFv, a disulfide stabilized Fv (Bera et al., *J. Mol. Biol.* 281:475-483, 1998), and dimeric Fvs (diabodies), that are generated by pairing different polypeptide chains (Holliger et al., *Proc. Natl. Acad. Sci. U.S.A.* 90:6444-6448, 1993), are also included.

In one embodiment, antibody fragments for use in this disclosure are those which are capable of cross-linking their target antigen, e.g., bivalent fragments such as F(ab')$_2$ fragments. Alternatively, an antibody fragment which does not itself cross-link its target antigen (e.g., a Fab fragment) can be used in conjunction with a secondary antibody which serves to cross-link the antibody fragment, thereby cross-linking the target antigen. Antibodies can be fragmented using conventional techniques and the fragments screened for utility in the same manner as described for whole antibodies. An antibody is further intended to include humanized monoclonal molecules that specifically bind the target antigen.

"Specifically binds" refers to the ability of individual antibodies to specifically immunoreact with an antigen. This binding is a non-random binding reaction between an antibody molecule and the antigen. In one embodiment, the antigen is DDR1. Binding specificity is typically determined from the reference point of the ability of the antibody to differentially bind the antigen of interest and an unrelated antigen, and therefore distinguish between two different antigens, particularly where the two antigens have unique epitopes. An antibody that specifically binds to a particular epitope is referred to as a "specific antibody."

In one specific, non-limiting example, the agent that inhibits DDR1 activation is a peptide molecule. In one example a peptide molecule inhibits the activation of DDR1 by binding a site on a DDR1 molecule. Without being bound by theory, the peptide can prevent another agent from binding the DDR1 molecule or it can change the conformation of DDR1 and inhibit its activation. In another non-limiting example, a peptide molecule inhibits the interaction of a DDR1 molecule, or part thereof, with a molecule in the DDR1 signaling pathway. The molecule in the signaling pathway can be an extracellular, or intracellular molecule. Extracellular signaling molecules include, but are not limited to, collagen. Intracellular signaling molecules include, but are not limited to, Shc and p38 MAP kinase.

A peptide derived from a specific binding domain, such as a collagen binding domain in DDR1 may encompass the amino acid sequence of a naturally occurring binding site, any portion of that binding site, or other molecular entity that functions to bind an associated molecule, such as collagen. A peptide derived from such a binding domain will interact directly or indirectly with an associated molecule in such a way as to mimic the native binding domain. Such peptides may include competitive inhibitors, enhancers, peptide mimetics, and the like. All of these peptides, as well as molecules substantially homologous, complementary or otherwise functionally or structurally equivalent to these peptides may be used for purposes of the present disclosure.

Particular peptides that may be used include peptides derived from the intracellular sites on a DDR1 (for example, DDR1b). In one embodiment, the peptide is derived from the portion of DDR1b that binds Shc. In one specific, non-limiting example, the peptide is derived from the Shc PTB binding domain.

Peptides of the disclosure may be used to identify lead compounds for drug development. The structure of the peptides described herein can be readily determined by a number of methods such as NMR and X-ray crystallography. Information can be obtained from the examination of structure and activity relationships, for example identifying which peptide structure has the greatest effect on DDR1 activity. This information can be used to design either modified peptides, small molecules or lead compounds, which can be tested for desired properties as related to the target molecule, for example decreased DDR1, activity. In one specific, non-limiting example, the target molecule is DDR1b. In another specific, non-limiting example, the target molecule is DDR1a.

In one specific, non-limiting example, the agent is a small molecule. A small molecule that affects DDR1 activity includes, but is not limited to, a tyrosine kinase inhibitor. Specific, non-limiting examples of tyrosine kinase inhibitors include leflunomides, genistein, herbimycin A, 2-Hydroxy-5-(2,5-Dihydroxybenzylamino)-2-hydroxybenzoic acid, tyrphostin, and STI 571 (Gleevec™). In one embodiment, the tyrosine kinase inhibitors are naturally occurring molecules. Examples of naturally occurring tyrosine kinase inhibitors include genistein, which is a steroid-like substance derived from soybeans, and lavendustin, which is a natural substance produced by microbes. In another embodiment, the tyrosine kinase inhibitors are chemically synthesized. Examples of chemically synthesized tyrosine kinase inhibitors are the tyrphostins. Other small molecules include lipid-soluble molecules, such as PMA, and the like.

A method is provided for screening for an agent that induces the maturation of an immature macrophage or an immature dendritic cell into a mature macrophage or a mature dendritic cell. The method includes contacting a n immature macrophage or an immature dendritic cell expressing a DDR1 with an agent to determine if the agent is capable of specifically binding to the DDR1. An agent that specifically binds the DDR1 is selected. Specific binding of the agent to the DDR1 indicates that the agent can induce the maturation of an immature dendritic cell or an immature macrophage.

In one embodiment, a DDR1b-expressing cell is contacted with an agent and it is determined if the cell can be induced to increase expression of a cytokine or a chemokine. Induction of the expression of the cytokine or the chemokine indicates that the agent activates DDR1b. Expression of the cytokine or chemokine can be compared to a control, such as a standard value, or to expression of the cytokine or chemokine by a cell not contacted with the agent.

Agents that are used to affect DDR1 activation can be provided to a cell, tissue, or subject. Examples of cells that are treated with agents that affect DDR1 activation include, but are not limited to, monocytes, macrophages, neutrophils, lymphocytes, dendritic precursor cells, immature dendritic cells, and mature dendritic cells. Cells can either be primary cells or cells derived from cell lines generated in vitro. One specific, non-limiting example of a monocytic cell line is THP-1. THP-1 cells can be induced to differentiate into a cell expressing macrophage cell surface markers or DDR1.

In one embodiment, the same agent that affects DDR1 activation induces monocyte or immature dendritic cell maturation. In another embodiment, the agent that affects DDR1 activation is different than the agent that induces monocyte or immature dendritic cell maturation. Specific, non-limiting examples of agents that induce monocyte, THP-1 cell, or immature dendritic cell maturation include collagen and PMA. For example, a second agent can be provided in combination with collagen. In one specific, non-limiting example, DDR1-expressing cells contacted with collagen and IFN-γ or DDR1-expressing cells are contacted with collagen in combination with IFN-γ, TNF-α, GM-CSF, or PMA.

The agent disclosed herein can be provided in vivo or in vitro. For example, agents can be provided in vitro to cells either growing in suspension or on tissue culture plates. In one specific, non-limiting example, a cell that is contacted with an agent that affects DDR1 activation is provided to a subject.

Agents that affect DDR1 activation can be provided either sequentially or simultaneously with induction of DDR1 expression in a cell. In one specific, non-limiting embodiment, the agent that affects DDR1 activation is the same as the agent that induces DDR1 expression. In another specific, non-limiting embodiment, the agent that affects DDR1 activation is different than the agent that induces DDR1 expression. Specific, non-limiting examples of agents that induce DDR1 expression include GM-CSF, TNF-α, IL-1β, IFN-γ, LPS, PHA, and fetal calf serum.

Pharmaceutical Compositions and Administration

Compositions comprising an agent that affects the DDR1 activation and the interaction of a DDR1-expressing cell with antigen can be administered directly to the subject to trigger antigen uptake and maturation of dendritic cells in vivo, thereby enhancing antigen presentation at a specific site in vivo. For example, an agent that affects DDR1 activation may be co-administered in solution, or in a delivery vehicle, such as a liposome, which would facilitate delivery and uptake of the an agent that affects the interaction of DDR1 and collagen and antigen by the monocytes or other dendritic cell precursors.

In another embodiment, compositions comprising an agent that affects DDR1 activation can be used to treat a subject having a tumor. As discussed above, tumor treatments may be based upon the development of anti-tumor vaccines comprising an agent that affects DDR1 activation and a tumor antigen, or an agent that affects the DDR1 activation and mature, tumor antigen-presenting dendritic cells. Without being bound by theory, such vaccines not only elicit anti-tumor antibody production, but also activate natural killer cell lytic activity and antibody dependent cellular cytotoxicity (ADCC). Thus, in the latter case, administration of compositions comprising an agent that affects DDR1 activation also stimulate production of tumor specific cytotoxic immune cells in vivo which actively target and kill tumor cells.

As disclosed herein, an agent that affects DDR1 activation can be used to generate mature dendritic cells, such as antigen presenting cells, in vivo. Thus, in one embodiment, a therapeutically effective amount of an agent that affects DDR1 activation is administered locally, such as to a specific site in a subject in order to trigger maturation of dendritic cells at that site. In another embodiment, a therapuetically effective amount of an agent that affects DDR1 activation is administered systemically, such as by intravenous, subcutaneous, intramusclar, intradermal, intraarterial, pareternal, or subcutaneous injection, or by oral administration or inhalation, to induce the maturation of dendritic cells.

In one specific non-limiting example, an agent that affects DDR1 activation is administered in conjunction with a pharmacologically acceptable carrier. Pharmacologically acceptable carriers (e.g., physiologically or pharmaceutically acceptable carriers) are well known in the art. A suitable pharmacological composition can be formulated to facilitate the use of an agent that affects DDR1 activation in vivo and/or ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers comprising excipients, as well as optional auxiliaries that facilitate processing of the active compounds into preparations which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to intravenous, intramuscular, intraperitoneal, transmucosal, subcutaneous, transdermal, transnasal, inhalation, and oral administration.

Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. An agent that affects DDR1 activation can also be formuated for use in inhalation therapy. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Similarly, an agent that affects DDR1 activation can be formulated for intratracheal or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

The disclosure is illustrated by the following non-limiting Examples.

EXAMPLES

Example 1

DDR1a Promotes Migration of Leukocytes in Three-Dimensional Collagen Lattices

Reagents and Preparation of Polymorphonuclear (PAN) and Peripheral Blood Mononuclear Cells (PBMC).

Human recombinant tumor necrosis factor-α (TNF-α) ($2.5 \times 10^7$ U/mg), interleukin-1β (IL-1β) ($1 \times 10^7$ U/mg), interferon-γ (IFN-γ) ($1 \times 10^7$ U/mg), granulocyte macrophage-colony stimulating factor (GM-CSF) ($2 \times 10^7$ U/mg) were purchased from R&D systems (Minneapolis, Minn.). Human recombinant monocyte chemoattractant protein-1 (MCP-1) was from Peprotech Inc. (Rocky Hill, N.J.). Anti-human DDR1 immunoglobulin (Ig) G was from Santa Cruz Biotechnology (Santa Cruz, Calif.). Mouse monoclonal antibodies against phosphotyrosine (4G10) and β1-integrin were from Upstate Biotechnology (Lake Placid, N.Y.). Dextran T500, protein G-Sepharose (PGS), and Percoll® were from Amersham Pharmacia Biotech, Inc. (Piscataway, N.J.). [α-$^{32}$P] dCTP was from ICN (Costa Mesa, Calif.). The retroviral vector pLXSN, retro viral packaging cell line PT-67, a human normal lung cDNA library, and human β-actin cDNA were from Clontech (Palo Alto, Calif.). Phosphate buffered saline (PBS), RPMI-1640, and TRIZOL Reagent were from Life Technologies (Gaithersburg, Md.). Fetal calf serum (FCS) was from HyClone (Logan, Utah). Phytohemagglutinin (PHA), paraformaldehyde, formamide, bovine collage type I were from Sigma (St. Louis, Mo.). Vitrogen was from Cohesion (Palo Alto, Calif.). Lipopolysaccharide (LPS) was from Difco (Detroit, Mich.). Accu-Prep was from Accurate Chemical & Scientific Corp. (Westbury, N.Y.). Proteinase K and RNase A were from Boehringer Manheim (Indianapolis, Ind.). mRNAlocator-Hyb kit was from Ambion (Austin, Tex.). The Vectastain ABC-AP kit and Vector Red Substrate Kit were from Vector Laboratories, Inc. (Burlingame, Calif.).

Human PMN and PBMC were obtained from heparinized blood from human donors or leukapheresis preparations obtained by the Blood Bank, Clinical Center, National Institutes of Health (Bethesda, Md.). One volume of 5% dextran in PBS was added to three volumes of blood in 50 ml polypropylene tubes. After a 40 minute incubation at room temperature, the leukocyte-rich plasma layer was removed and overlaid onto Accu-Prep in 50 ml tubes, and the tubes were centrifuged at 800×g for 20 minutes at room temperature. PBMC fractions were collected, washed once with PBS at room temperature and twice with RPMI-1640 containing 10% FCS (complete medium) at 4° C., and resuspended in the complete medium. PMN were separated from erythrocytes by lysis in 0.2% NaCl, washed in complete medium three times at 4° C., and resuspended in the complete medium. In a few experiments, monocytes and lymphocytes were purified further by using iso-osmotic Percoll® gradient. The purity of monocytes and lymphocytes was higher than 90%.

Regulation of DDR1 mRNA Expression in Leukocytes

PMN and PBMC were maintained at a density of $5\times10^6$ cells/ml in the complete medium in six-well tissue culture cluster (Coster, Cambridge, Mass.; 3 ml/well). Total RNA was extracted from each culture by using TRIZOL® Reagent. PolyA mRNA was purified on Oligotex columns (Qiagen, Valencia, Calif.). Northern blot analysis was performed as described (Yoshimura, *J. Immunol.* 150:5025, 1993), except that ULTRAhyb (Ambion) was used. A human DDR1 cDNA (757-bp) was obtained by PCR from a U-105 human glioblastoma cell line cDNA library and was ligated into the EcoRI/HindIII site of the pBluescript (Stratagene, La Jolla, Calif.). The sense primer was 5'-CTTTACTGCTGCTGCTCTTG-3' (SEQ ID NO: 2; corresponding to residues between 68 and 87 in the nucleotide sequence of the trkE cDNA, GenBank accession number X74979) and the antisense primer was 5'-TTGCTCCATCCCACATAGTC-3' (SEQ ID NO: 3; corresponding to residues between 805 and 824 in the nucleotide sequence of the trkE cDNA).

DDR1 mRNA expression in PBMC and PMN was demonstrated by Northern blot analysis. Low-level DDR1 mRNA expression was detected in freshly isolated PBMC. The level of DDR1 mRNA increased progressively during incubation in RPMI 1640 containing 10% FCS. The level of DDR1 mRNA expression peaked by 16 hours, and the peak level was sustained up to 48 hours. A low level of DDR1 mRNA was also detected in freshly isolated PMN, and the expression level markedly increased after an 8 hour incubation in RPMI 1640 containing 10% FCS.

To demonstrate further the regulation by endogenous and exogenous proinflammatory agents of DDR1 mRNA expression in PBMC, PBMC were incubated in the presence or absence of 10% FCS, TNF-α (5 ng/ml), IL-1β (10 ng/ml), IFN-γ (50 U/ml), GM-CSF (10 ng/ml), LPS (1 μg/ml), or PHA (5 μg/ml) for 8 hours and the level of DDR1 mRNA expression was examined by Northern blotting. Freshly isolated PBMC expressed only a low level of DDR1 mRNA. The expression level was increased about eightfold when the cells were incubated in either RPMI 1640 or RPMI 1640 containing 10% FCS. Addition of TNF-α, IL-1β, GM-CSF, LPS, or PHA further augmented the expression levels of DDR1 mRNA. In contrast, IFN-γ partially inhibited the expression of DDR1 mRNA induced by in vitro incubation.

Expression of DDR1 mRNA and Protein in Leukocytes

To detect the expression of DDR1 protein in leukocytes, immunocytochemical and Western blot analysis was performed with an antibody against DDR1. Immunocytochemistry was performed by using the Vectastain ABC-AP kit (Vector Laboratories, Burlingame, Calif.). Leukocytes that settled onto silanated slides (CEL Associates, Inc., Houston, Tex.) were air-dried and fixed in 4% paraformaldehyde in PBS at 4° C. for 15 minutes. For better permeability of the antibody, the cells were treated with 0.1% Triton X-100/PBS for 5 minutes. After blocking nonspecific protein binding with diluted horse serum, the cells were incubated with anti-DDR1 polyclonal IgG (1 μg/ml) at 4° C. overnight. After being washed with PBS, the cells were reacted with biotinylated anti-rabbit IgG for 45 minutes, followed with ABC-AP reagent for 20 minutes. Alkaline phosphatase activity was visualized by using the Vector Red Substrate Kit. The slides were counter-stained with hematoxylin. Normal rabbit IgG was used instead of the primary antibody as negative control.

For Western blot analysis, cell lysates were prepared from freshly isolated PBMC, PBMC incubated overnight in RPMI 1640 containing 10% FCS, and MCF-7 cells. Cells were lysed on ice for 20 minutes in a buffer containing 50 mM Hepes, 150 mM NaCl, 1% Triton X-100, 10% glycerol, 10 mM NaF, 1 mM ethylenediamine tetraacetic acid, 200 mM sodium orthovanadate, 1 mg/ml leupeptin, 1 mM phenylmethylsulfonyl fluoride, 1 mg/ml aprotinin, and 1 mg/ml pepstatin A. The lysates were spun, and the supernatants were collected. The samples were incubated with approximately 20 μl packed volume of PGS for 1 hour at 4° C. After centrifugation, supernatants were collected, mixed with 1 μg/ml normal rabbit IgG or polyclonal anti-human DDR1 IgG, and incubated for 1 hour at 4° C. PGS (20 μl) was then added and incubated for another 1 hour. IgG-coupled PGS was washed with the buffer containing 50 mM Hepes, 150 mM NaCl, 0.1% Triton X-100, 10% glycerol buffer three times, and 20 μl double-strength sample buffer (20% glycerol, 6% sodium dodecylsulfate (SDS), 10% 2-mercaptoethanol) was added. The samples were boiled for 10, minutes. Eluted proteins were analyzed on 7.5% polyacrylamide gels by SDS polyacrylamide gel electrophoresis (SDS-PAGE) and transferred electrophoretically to nitrocellulose membranes (Amersham, Arlington Heights, Ill.) at 200 mA for 2 hours by a semi-dry system. The membranes were incubated with polyclonal anti-human DDR1 or anti-phosphotyrosine IgG, followed by sheep anti-mouse IgG coupled with horseradish peroxidase (Amersham). Peroxidase activity was visualized by the Enhanced Chemiluminescence Detection System (Amersham).

In situ hybridization was performed by using a nonradioactive system as described previously (Hirota et al., *Mol. Brain Res.* 15:47, 1992). The antisense and sense probes were transcribed by the DIG RNA labeling Kit (Roche Molecular Biochemicals, Indianapolis, Ind.). Paraffin sections (5-μm-thick) or PBMC that settled onto silanated glass slides, were post-fixed in 4% paraformaldehyde after proteinase K (5 μg/ml) treatment at 37° C. for 3 minutes. The tissues/cells were denatured with 0.2 N HCl for 10 minutes, acetylated with 0.1 M triethanolamine and 0.25% acetic anhydride at room temperature and were then incubated for 16 hours at 50° C. in a 30-μl solution containing 50% formamide, 10% dextran sulfate, 1 Denhardts solution, 0.6 M NaCl, 1 M Tris-HCl (pH 7.6), 250 μg/ml tRNA, 125 μg/ml salmon sperm DNA, and 20 ng of DIG-labeled RNA probe. After hybridization, the tissues/cells were washed with 2 standard saline citrate (SSC), 50% formamide for 30 minutes, and treated with 10 mg/ml RNase A for 30 minutes. After the final washes in 2×SSC and 0.2×SSC at 50° C. for 20 minutes each, hybridized probe was detected immunologically by using the Genius 3 Nonradioactive Nucleic Acid Kit (Roche Molecular Biochemicals). Positive signals obtained by this method resulted in a deep blue-purple staining. The tissues/cells were counterstained with hematoxylin and covered by coverslips for evaluation by light microscopy.

Freshly isolated unstimulated PBMC or PMN were negative for DDR1 protein. However, after overnight incubation in RPMI 1640 containing 10% FCS, immunoreactive DDR1 became detectable in PMN, monocytes, and lymphocytes using immunocytochemical techniques. The expression level of DDR1 in PMN was much lower than that in monocytes or lymphocytes.

DDR1 protein expression by PBMC was also demonstrated by Western blotting. There was no detectable DDR1 protein in freshly isolated PBMC. DDR1 protein was detected clearly after overnight incubation in RPMI 1640 containing 10% FCS. In order to study the kinetics of DDR1 protein expression, PBMC were incubated with or withour addition of TNF-α (5 ng/ml), or GM-CSF (10 ng/ml) for 36 hours and cell lysates were prepared. Cell lysates were subjected to immunoprecipitation with anti-DDR1 IgG or control IgG. The membrane was blotted with anti-DDR1 IgG. MCF-7 cells were used as DDR1 positive control. DDR1 protein expression in PBMC showed that DDR1 protein was detectable after a 12-hour incubation with 10% FCS. The expression level reached a peak by day 3, and the protein was still detectable after 6 days in culture. Activation of PBMC with TNF-α or GM-CSF increased the level of DDR1 protein expression. Activation of monocytes with GM-CSF, or lymphocytes with PHA, increased the DDR1 protein expression by each cell type, indicating that DDR1 expression can be up-regulated in both monocytes and lymphocytes.

Numerous mononuclear leukocytes were observed infiltrating the periphery of renal cell carcinoma, as detected by hematoxylin-eosin (H&E)-staining. There were no tumor cells in the region of leukocyte infiltration. By in situ hybridization with an antisense probe, DDR1 mRNA was readily detected in the cytoplasm of the infiltrating mononuclear cells. These cells were not stained with a sense probe. Some of the positive cells had abundant cytoplasm with extended pseudopod formation, characteristic of macrophages. Because DDR1 mRNA was not detected in freshly isolated PBMC by the same method, the DDR1 mRNA expression was up-regulated in cells that had emigrated into the extravascular space.

Identification of the Major Isoform of DDR1 in Leukocytes

There are at least five isoforms of DDR1 mRNA. The DDR1a and DDR1b isoforms differ by an in-frame insertion of 111-bp coding for additional 37 amino acids in the proline-rich juxtamembrane region, due to alternative splicing of this gene (Playford et al., *Genome Res.* 6:620, 1996). The 37-amino acid insertion found in DDR1b contains the LXN-PXY (SEQ ID NO: 1) motif that corresponds to the consensus-binding motif for the Shc phosphotyrosine binding domain. DDR1b, but not DDR1a, interacts with Shc (Vogel et al., *Mol. Cell,* 1:13, 1997). Another six-amino-acid insertion at the beginning of the kinase domain of DDR1b gives rise to the DDR1c isoform (Alves et al., *Oncogene,* 10:609, 1995). However, the biological significance of this six-amino-acid insertion remains uncertain.

To measure the expression levels of DDR1 isoforms in leukocytes, RT-PCR was performed with the Superscript II one-step RT-PCR system (Life Technologies). The sense primer used was 5'-GCTCCTGCTGCTCATCATTG-3' (SEQ ID NO: 4; corresponding to exon 9 of DDR1), and the antisense primer was 5'-TAATGGGGGACGCTGTTCTG-3' (SEQ ID NO: 5; corresponding to exon 12, of DDR1). Duplicate RT-PCR was performed on a minimum of two separately prepared RNA samples for each experiment. The primers were designed to detect the presence of the 111-bp insertion that is missing from DDR1a but present in DDR1b and c.

Transcripts isolated from PMN, monocytes, and lymphocytes after an 8 hour incubation at 37° C., all contained isoforms with or without the insertion. However, the amplification of the DDR1a isoform was higher than that of other isoforms. Because the isoforms with the 37-amino-acid insertion were consistently amplified significantly higher than the DDR1a isoform from the transcripts of MCF-7 cells by the same method, it is unlikely that DDR1a transcript was amplified preferentially by the method. There was no difference in the ratio of DDR1a and the others over a 48 hour interval with or without further activation with proinflammatory agents. Thus, the majority of the DDR1 isoform expressed in cultured leukocytes was DDR1a.

Induction by Collagen of Autophosphorylation of DDR1a and DDR1b Overexpressed in THP-1 Cells A human normal lung cDNA library in the pTriplex vector was screened to obtain full-length DDR1a and DDR1b cDNAs. The library was screened by using the PCR-amplified cDNA probe described above. After two rounds of screening, five positive phage clones were obtained and converted to plasmid clones by in vivo excision. DNA sequencing revealed that one of the clones, clone 11B, contained the full-length human DDR1b cDNA. The full-length DDR1a cDNA was generated from the clone 11B by exchanging the SacI-BamHI fragment of the clone 11B with the SacI-BamHI fragment of the clone 11A, which lacked 111-bp in the juxtamembrane region.

The full-length human DDR1a or DDR1b cDNA was ligated into the EcoRI/BamHI site of the retroviral vector pLXSN. The viral packaging cell line PT67, was transfected with each retroviral expression construct by a calcium phosphate method. Twenty-four hours after transfection, old media were replaced with fresh media, and the cells were selected in the presence of G418 for 5 days. Several clones were obtained after limiting dilution of the selected cells, and the viral titers in the culture supernatants were measured by infecting Balb-3T3 cells with serially diluted supernatants. Typically, the titers ranged from $5 \times 10^5$ to $1 \times 10^7$ cfu/ml. The culture supernatants containing high titers of retrovirus were harvested and filtered through 0.45-μm pore size Millex-HA (Millipore, Bedford, Mass.). The supernatants containing vector only, DDR1a, or DDR1b were then added to the human monocytic leukemia cell line, THP-1 (American Tissue Culture Collection, Rockville, Md.), in the presence of polybrene. After 24 hour infection, DDR1-expressing THP-1 cells were selected with G418 selection and cloned by limiting dilution.

To determine the biological role of the DDR1a isoform and compare with that of the DDR1b isoform in leukocytes, DDR1a or DDR1b was overexpressed in cells of the human monocytic THP-1 leukemic cell line. THP-1 cells did not express detectable levels of DDR1 mRNA by RT-PCR or DDR1 protein by Western blotting. THP-1 cells were infected with retrovirus expressing either DDR1a or DDR1b and were selected in the presence of G418. Multiple clones expressing different levels of DDR1a or DDR1b were obtained by limiting dilution. The expression of each DDR1 isoform in each clone was confirmed by RT-PCR. The expression of DDR1 protein was also confirmed by Western blotting.

Previous studies of DDR1 in different cell types resulted in conflicting observations. In embryonic kidney fibroblast 293 cells, COS cells, NIH 3T3 fibroblasts, and several tumor cell lines, expressed DDR1 could be autophosphorylated (Shrivastava et al., *Mol. Cell,* 1:25, 1997; Vogel et al., *Mol.*

Cell, 1:13, 1997; Alves et al., Oncogene, 10:609, 1995), whereas DDR1 in PC12 cells, either endogenously expressed or overly expressed, was not autophosphorylated (Foehr et al., FASEB J. 14:973, 2000).

Using the retrovirus-infected cell lines, the effect of collagen type I on the phosphorylation of DDR1 proteins was tested. Two million cells in 3 ml complete medium were added onto collagen type I-coated plastic plates and incubated at 37° C. for various times. Cell lysates were prepared and immunoprecipitation was performed with the anti-DDR1 antibody. One-fourth of the immunoprecipitated samples was subjected to SDS-PAGE and Western blotting. The membranes were blotted with anti-pTyr and anti-DDR1 antibody. Low levels of constitutive autophosphorylation of both receptors were detected. The levels of autophosphorylation increased slightly at 15 minutes and peaked at 90 minutes after activation of the cells on collagen type I-coated plastic plates. The peak level was maintained for up to 240 minutes for DDR1a, which is consistent with the previously reported delayed kinetics of DDR1b autophosphorylation in other cell types (Vogel FASEB J, (Suppl.), S77-S82, 1999). In contrast, autophosphorylation of DDR1b decreased after 90 minutes of collagen-activation. These results indicated that DDR1a and DDR1b have a different role in THP-1 cells.

Effects of Overexpression of DDR1a or DDR1b on Adherence and Morphology

To determine the effects of collagen on the functions of DDR1a- and DDR1b-overexpressing THP-1 cells, the cells were incubated on collagen-coated plastic plates. Twenty-four-well plates were coated with 100 µl/well human collagen type I (20 µg/ml) overnight at 4° C., and then with 200 µl/well 10 mg/ml bovine serum albumin (BSA) for 1 hour at 37° C. Cells were plated at the cell density of $1\times10^5$ cells/ml to the coated wells and were incubated for 30 minutes at 37° C. in 5% CO2 humidified atmosphere. Nonadherent cells were removed by washing three times with PBS. Cells that remained on the coated surface were considered to be adherent, and the number of cells in each 400 field was counted. Results were presented as mean ±SE per 400 field.

Figure 2:
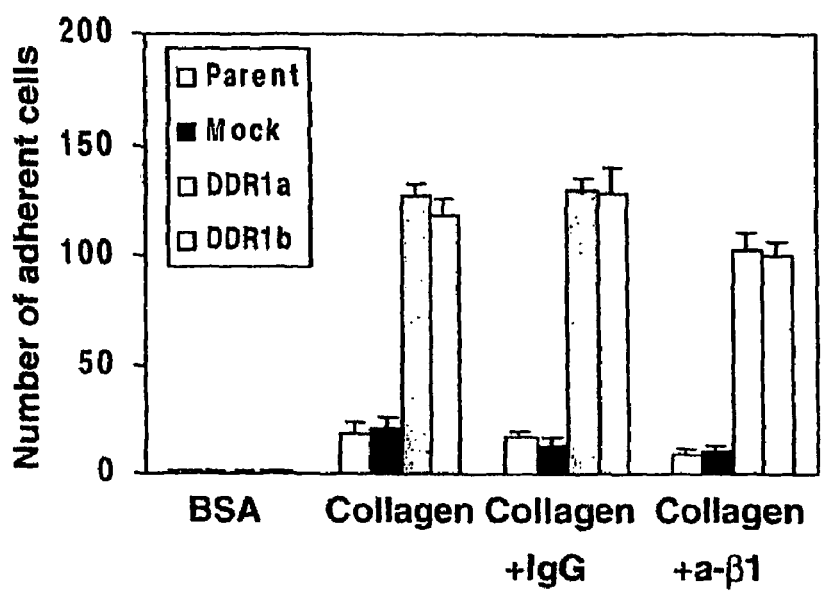
FIG. 2 is a graph demonstrating increased adherence of DDR1 a- and DDR1b-overexpressing THP-1 cells to collagen-coated plates. $5 \times 10^5$ cells/ml were cultured on either BSA (10 mg/ml)- or collagen (20 μg/ml) and BSA-coated plates for 30 (FIG. 2A) or 120 minutes (FIG. 2B) at 37° C. in a 5% $CO_2$ humidified incubator. Normal mouse IgG or anti-β1 integrin blocking IgG was added to measure the effect of β1 integrin in the assay. The number of adherent cells in each 400× visual field was counted. The results are presented as means ±SE of four individual fields. Data are representative of three experiments with two independent clones overexpressing either DDR1a or DDR1b.
Figure 2:
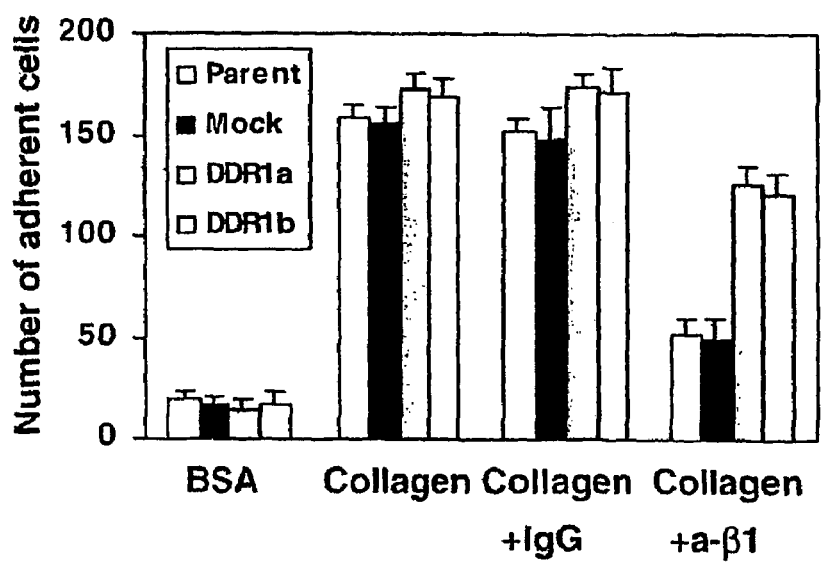

As shown in FIG. 2A, none of the cell lines showed significant adherence to BSA-coated plates after 30 minute incubation at 37° C. Small numbers of parental and mock-infected THP-1 cells adhered to collagen-coated plates. They could be inhibited largely by an anti-β1-integrin blocking antibody. In contrast, greater numbers of either DDR1a- or DDR1b-overexpressing THP-1 cells (~62% of total cells) adhered to collagen-coated plates after 30 minutes and the adhesion of these cells was not inhibited by the anti-β1 integrin blocking antibody. At 2 hours, all four cell lines exhibited increased adherence to collagen-coated plates (FIG. 2B). However, adherence of parental or mock-infected cells was largely inhibited by the anti-β1-integrin blocking antibody, whereas the antibody had much less of an effect on the adherence of DDR1a- or DDR1b-overexpressing cells. There was no significant difference in the levels of cell-surface β-1 integrin expression between cell lines measured by fluorescence activated cell sort (FACS). These results indicate that DDR1a or DDR1b-overexpressing cells can adhere to collagen-coated plates independent of β-1 integrin.

There was a dramatic morphological difference between DDR1a- and DDR1b-overexpressing cells after a 1 hour incubation. DDR1a-overexpressing cells extended long pseudopods. In contrast, DDR1b-overexpressing cells, as well as parental or mock-infected cells, did not show similar pseudopod extension. An identical morphological change was observed when DDR1a-overexpressing cells were seeded in three-dimensional collagen lattices. In contrast to the effects of collagen, coating the plates with fibronectin had no effect on the adherence or shape change of DDR1a- and DDR1b-overexpressing cells.

Effects of Overexpression of DDR1a and DDR1b on Random and Directed Migration of THP-1 Cells in Three-Dimensional Collagen Lattices The cell migration assay was performed by using the 24-well BioCoat Insert Chamber (Becton Dickinson, Bedford, Mass.). Cell suspension (500 µl; $1\times10^5$ cell/ml) in the complete medium was placed in each inner well that was separated from the outer well containing 700 µl of human recombinant MCP-1 (10 ng/ml) by a polycarbonate membrane with 8-µm-diameter pores. After a 3-hour incubation at 37° C., the numbers of cells that were adhering on the other side of the membrane and also had fallen into the outer wells were counted. To demonstrate the migration of cells through three-dimensional collagen lattices, purified bovine collagen solution (Vitrogen) was diluted in RPMI 1640 (1 mg/ml, pH 7.4). One hundred µl of the diluted solution was overlaid on a polycarbonate membrane of the inner wells to polymerize for 60, minutes at 37° C. in 5% $CO_2$ humidified atmosphere. Cell suspensions (500 µl; $1\times10^5$/ml) were then added to the inner wells. After an 8-hour incubation at 37° C., the numbers of cells that were adhering on the other side of the membrane and also had fallen into the outer wells were counted.

Figure 3:
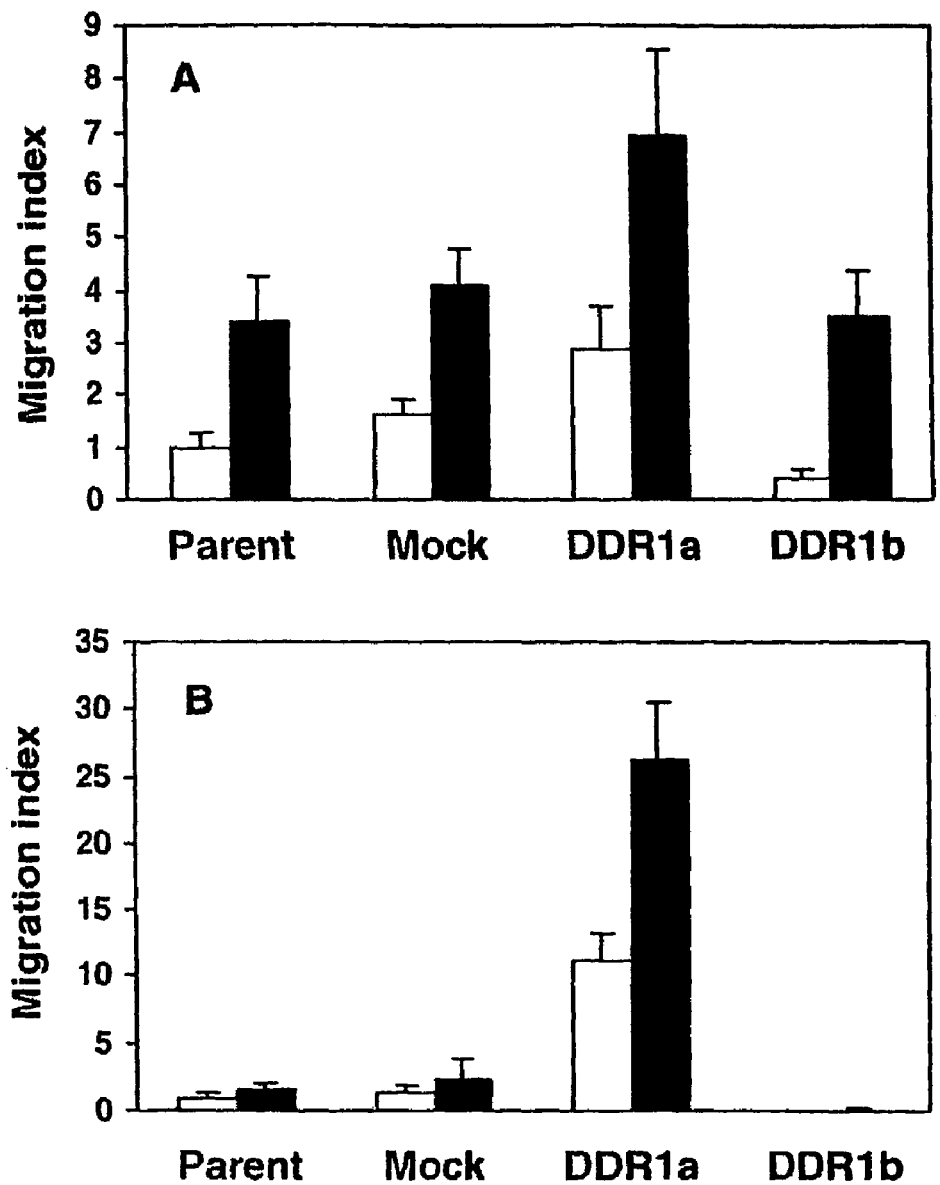
FIG. 3 is a series of graphs demonstrating enhanced migration of DDR1a-overexpressing THP-1 cells through three-dimensional collagen lattices. Migration of each cell type in response to medium (open column) or MCP-1 (closed column) was measured in the 24-well BioCoat Insert Chamber as described in Example 1 below.

The migration of DDR1a- or DDR1b-overexpressing THP-1 cells was demonstrated by using cell culture inserts. Inner wells containing cell suspension were separated from outer wells by a polycarbonate membrane with 8-µm-diameter pores. The complete medium or 10 ng/ml MCP-1 was added to the outer wells to measure random or directed migration of each cell line. As shown in FIG. 3A, a small number of parental cells migrated through 8-µm pores without MCP-1 in the outer wells. Migration of mock-infected cells was increased slightly but not significantly. Overexpression of DDR1a resulted in an approximately threefold increase in the number of migrating cells, whereas overexpression of DDR1b resulted in an approximately twofold decrease. When MCP-1 was placed in the outer wells, the migration of parental, mock-infected, and DDR1a- overexpressing TIP-1 cells increased two- to threefold, indicating that the migratory activity of DDR1a-overexpressing cells was enhanced. Although the response of DDR1b-overexpressing cells to the complete medium was lower in comparison with that of parental or mock-infected cells, the response to MCP-1 was at the same level. The migration of DDR1a-overexpressing cells was increased even more greatly when three-dimensional collagen lattices were generated over the polycarbonate membranes (FIG. 3B). Although the migration of parental or mock-infected cells in response to either the complete medium or MCP-1 was minimal in the presence of collagen lattices, the enhanced migratory response of DDR1a-overexpressing cells was still evident and the increase was ~12-fold. Migration of DDR1b-overexpressing cells was inhibited completely in collagen lattices. Addition of an anti-β1 integrin antibody had no effect on the enhanced migration of DDR1a-overexpressing cells in three-dimensional collagen lattices.

Example 2

DDR1b in Response to Collagen Transduces Signals that Promote Differentiation of Phorbol Ester-Primed Human Monocytic THP-1 Cells Reagents A rabbit polyclonal antibody against human DDR1 and a mouse monoclonal antibody against human Shc were from Santa Cruz Biotechnology (Santa Cruz, Calif.). Rabbit polyclonal antibodies specific for DDR1a or DDR1b, and mouse monoclonal antibodies against DDR1 were also prepared, as described below. Mouse monoclonal antibodies against phosphotyrosine (4G10) and β1-integrin were from Upstate Biotechnology (Lake Placid, N.Y.). Rabbit polyclonal antibodies against p38 MAP kinase, phosphorylated p38 MAP kinase, MAP kinase kinase (MKK) 3/MKK6 activating transcription factor 2 (ATF-2), phosphorylated ATF-2 extracellular signal-regulated kinase (ERK) and phosphorylated ERK were from Cell Signaling Technology (Beverly, Mass.). Sheep anti-mouse or anti-rabbit IgG coupled with horseradish peroxidase, and [$\alpha$-$^{32}$P]dCTP were from Amersham Pharmacia Biotech, Inc. (Pascataway, N.J.). Mouse monoclonal antibodies against CD14, CD11c, CD40, and HLA-DR, and control mouse monoclonal IgM were from PharMingen (San Diego, Calif.). Human HLA-DR α-chain cDNA was from Incyte Genomics Inc. (St. Louis, Mo.). Human β-actin cDNA was from Clontech (Palo Alto, Calif.). Phosphate buffered saline (PBS), RPMI 1640, G418, recombinant protein G-agarose (PGA), TRIzol Reagent®, Superscript RNase H-reverse transcriptase, and pre-cast tris-glysine SDS gel were from Invitrogen (Gaithersburg, Md.). FCS was from HyClone (Logan, Utah). Paraformaldehyde, formamide, human serum, propidium iodide (PI) and bovine collagen type I were from Sigma (St. Louis, Mo.). SB203580, PD98059, and cycloheximide (CHX) were from Biochem-Novabiochem (San Diego, Calif.). Human recombinant granulocyte-macrophage colony-stimulating factor (GM-CSF) was from PeproTech Inc. (Rocky Hill, N.J.).

Preparation of DDR1 Antibodies

Rabbit polyclonal antibodies specific for DDR1a or DDR1b were raised against a synthetic peptide (CVPNGSAYSGDY) (SEQ ID NO: 6) found only in DDR1a, or two overlapping peptides (CARPPRGPGPPTPAWAK) (SEQ ID NO: 7) and (PRGPGPPTPAWAKPTNC) (SEQ ID NO: 8) that are found only in DDR1b. The peptides were coupled to keyhole limpet hemocyanin (KLH) before injection into rabbits. Specific antibodies were affinity-purified from immune sera by purification over matrix-bounded peptides (UltraLink columns, Pierce, Rockford, Ill.) according to standard procedures. The specificity of the antibody was tested by Western blotting using cell lysates of DDR1a- or DDR1b-overexpressing THP-1 cells and glutathione-S-transferase (GST)-fusions of DDR1a and DDR1b intracellular domains.

Mouse monoclonal anti-DDR1 IgM 513 (Alves et al., FASEB J. 15:1321, 2001) was raised against the entire extracellular domain of DDR1. The antibody was produced by growing the hybridoma cells (513GA12) in protein-free medium (Protein Free Hybridoma Medium, GIBCO/Invitrogen). The isotype of the antibody produced is IgM. This antibody has the capacity to induce autophosphorylation of DDR1.

Cell Lines

Production of mock-infected, DDR1a- or DDR1b-overexpressing THP-1 cells was previously described (Kamohara et al., FASEB J. 15:2724, 2001). Each cell line was maintained in RMPI1640 supplemented with 10% FCS and 100 µg/ml gentamicin. To induce differentiation of THP-1 cells, cells were plated at the cell density of $5\times10^6$/ml and incubated at 37° C. in 5% $CO_2$ humidified atmosphere for various time periods in the presence of 10 nM PMA in tissue culture plates.

Effects of DDR1-Collagen Interaction on the Proliferation of PMA-Treated THP-1 Cells One hundred µl of cell suspension ($5\times10^6$/ml) were plated in 96-well tissue culture plates either collagen-coated or non-coated, and incubated at 37° C. in 5% $CO_2$ humidified atmosphere in the presence of 10 nM PMA for 48 hours. Cell proliferation was measured by using the CellTiter 96 Aqueous Non-Radioactive Cell Proliferation Assay Kit (Promega, Madison, Wis.) according to the manufacture's protocol. Trypan-blue staining was also used to measure the number of live cells in each culture.

Figure 4:
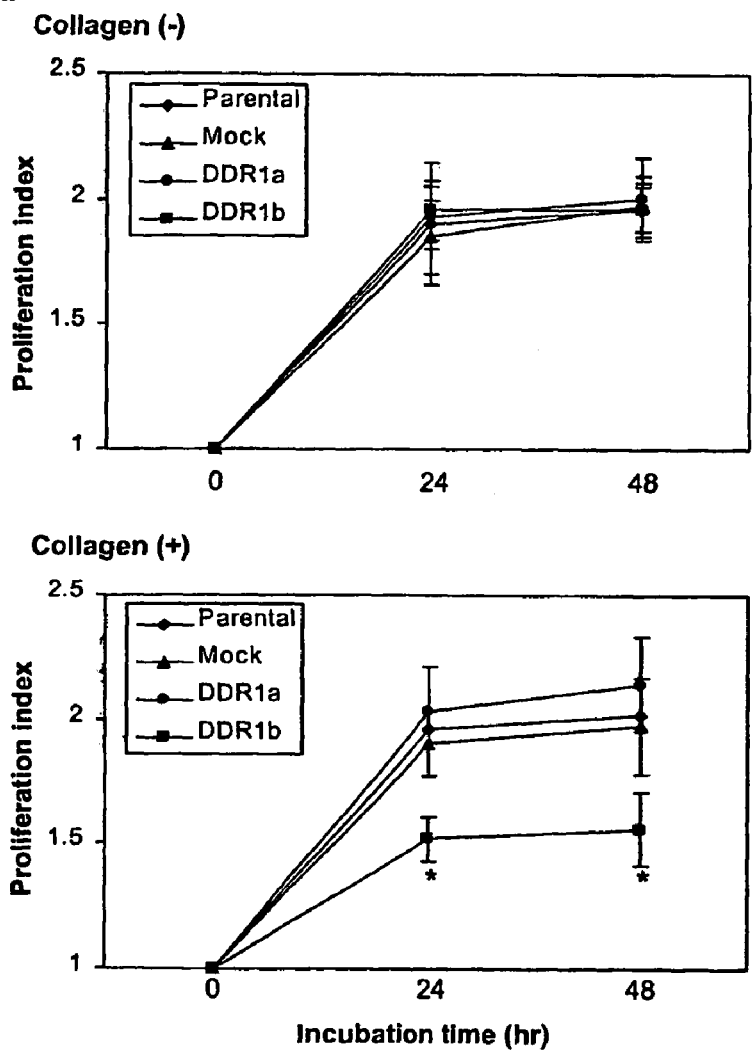
FIG. 4 is a series of images demonstrating the effects of collagen-activation of two DDR1 isoforms on cell proliferation. One hundred μl of cell suspension ($5 \times 10^6$/ml) were plated in 96-well tissue culture plates either uncoated or collagen-coated, and incubated at 37° C. in the presence of 10 nM phorbol 12-myristate 13 acetate (PMA) for 24 or 48 hours (FIG. 4A). Data are shown as the mean ±SD of 10 wells. *$p<0.01$ by Bonferroni/Dun with One Way Factorial ANOVA. The expression level of DDR1 in different cell lines after activation with PMA plus collagen for 48 hours is shown in FIG. 4B. Twenty μl of each cell lysate were loaded and Western blotting was performed. The expression levels of DDR1 in DDR1a- or DDR1b-overexpressing THP-1 cells before and after treatment with PMA plus collagen are shown in FIG. 4C. Twenty μl of each cell lysate were loaded and Western blotting was performed.
Figure 4:
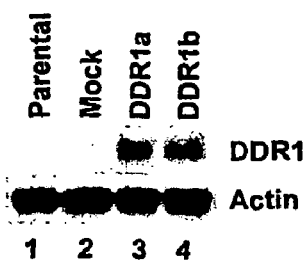
Figure 4:

One of the events associated with cell differentiation is a reduction in proliferation. To assess the effect of DDR1-collagen interaction on the proliferation of PMA-treated THP-1 cells, parental, mock, DDR1a-overexpressing, or DDR1b-overexpressing THP-1 cells were incubated on either uncoated or collagen-coated tissue culture plates. As shown in FIG. 4A, there was no significant difference in cell proliferation after PMA-treatment of each cell line on uncoated plates. However, when the cells were incubated on collagen-coated plates (FIG. 4A), the proliferation of DDR1b-overexpressing cells was decreased by about 50% at both 24 hour and 48 hour compared with that of parental, mock, or DDR1a-overexpressing cells. This was not due to increased cell death because the viability of the cells after PMA-treatment was almost identical as determined by trypan blue staining. There was also no detectable endogenous expression of DDR1 in PMA-treated parental cells by Western blotting. The expression levels of DDR1a or DDR1b in DDR1a- or DDR1b-overexpressing cells were similar (FIG. 4B, lanes 3, 4) and treatment with PMA plus collagen did not alter the expression levels in these cell lines (FIG. 4C). These results were confirmed using two independent clones of DDR1a- or DDR1b-overexpressing THP-1 cells.

Effects of DDR1-Collagen Interaction on the Expression of HLA-DR, CD11c, CD14 and CD40 by PMA-Treated THP-1 Cells Parental, mock, DDR1a-overexpressing, or DDR1b overexpressing THP-1 cells were plated at $5\times10^6$ cells/ml on either uncoated or collagen-coated plates and incubated at 37° C. for 24 or 48 hours in the presence of 10 nM PMA. One hundred thousand cells were suspended in 50 µl of cold PBS containing 0.1% $NaN_3$, 10 ng/ml BSA and 200 µg/ml human IgG in a Falcon 2052 tube, and incubated for 10 minutes on ice. One µg of mouse monoclonal antibody against CD11c, CD14 CD40, or HLA-DR, or control mouse IgG were added to each tube and the cells were incubated for another 15 minutes on ice. The cells were washed with PBS, and then incubated with 1 µg of FITC-conjugated goat anti-mouse IgG for 15 minutes on ice. At the end of incubation, propidium iodide (PI) (100 µM) was added to each tube. The cells were washed by PBS, and subsequently analyzed by using a FACS scan (Becton Dickinson). Dead cells, determined by the incorporation of PI, were gated out. Results were processed by using the Cellquest software (Becton Dickinson).

PMA-treatment of parental, mock, DDR1a-overexpressing, or DDR1b-overexpressing THP-1 cells for 48 hours resulted in the appearance of similar levels of HLA-DR-positive cells (26 to 28%) on uncoated plates. On collagen-coated plates, however, a significantly higher percentage (approximately 25%) of DDR1b-overexpressing cells expressed HLA-DR after a 24 hour incubation. Approximately 70% of the DDR1b-overexpressing cells expressed HLA-DR after a 48 hour incubation, whereas approximately 28% of cells in other cell lines expressed HLA-DR. This increased HLA-DR expression by DDR1b-overexpressing cells at 48 hours was not affected by a blocking antibody against β1 integrin. A kinetics study indicated that a significant HLA-DR expression was detected in collagen-activated PMA-treated DDR1b-overexpressing cells as early as 12 hours. Approximately 10% of the cells expressed HLA-DR, whereas only 2% of the cells in other cell lines expressed HLA-DR. The percentages of HLA-DR-positive cells in collagen-activated PMA-treated DDR1b-overexpressing cells were significantly higher than that in cell of other cell lines at 18, 24, 36, and 48 hours. Addition of anti-β1 integrin blocking antibody did not affect the percentage of HLA-DR expression at 24, 36, and 48 hours.

Figure 5:
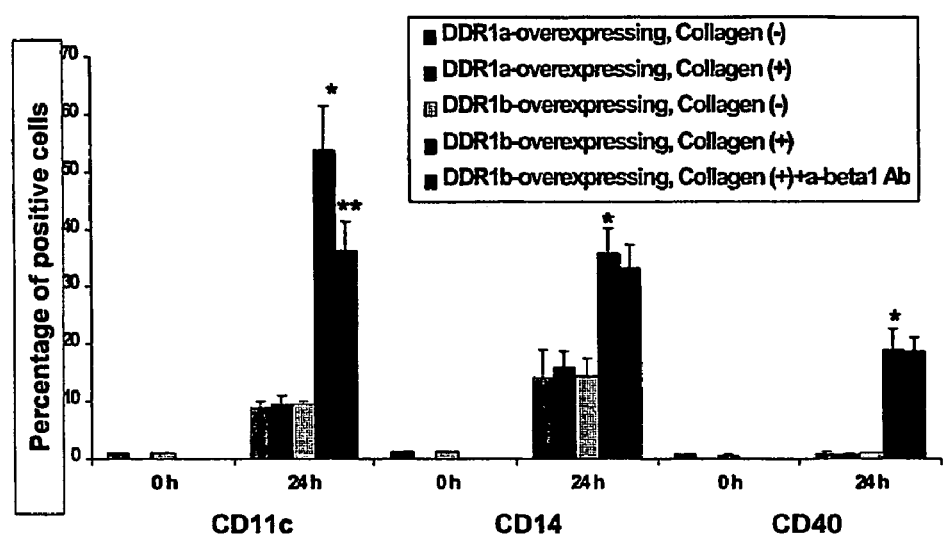
FIG. 5 is a graph showing the effects of collagen-activation of two DDR1 isoforms on the expression of CD11c, CD14, and CD40. Each cell line was plated at $5 \times 10^6$ cells/ml on either uncoated or collagen-coated plates and incubated at 37° C. for 24 hours in the presence of 10 nM PMA. Anti-1β integrin antibody (10 μg/ml) was used to block the effect of 1β integrin-collagen interaction. The percentage of CD11c, CD14, or CD40-positive cells is shown. Data are presented as the mean ±SD from three independent experiments.

The effects of collagen on the expression of CD11c, CD14, and CD40 were also measured in PMA-treated DDR1a- or DDR1b-overexpressing cells at 24 hours. As shown in FIG. 5, approximately 10% and 15% of the cells in each cell line expressed CD11c and CD14 on uncoated plates, respectively. However, approximately 53% and 35% of DDR1b-overexpressing cells expressed CD11c and CD14 on collagen-coated plates, whereas the percentages of CD11c- or CD14-positive cells in DDR1a-overexpressing cells were unchanged. A blocking antibody against β1 integrin significantly inhibited the expression of CD11c, but not CD14. The expression of CD40 was not induced in DDR1a-overexpressing cells even on collagen-coated plates. In contrast, approximately 19% of DDR1b-overexpressing cells expressed CD40 on collagen-coated plates. Again, the expression of CD40 was not affected by an anti-β1 integrin blocking antibody (Ab). The expression of these cell-surface molecules in parental and mock THP-1 cells was similar to that in DDR1a-overexpressing cells. These results were confirmed using two independent clones of DDR1a- or DDR1b-overexpressing THP-1 cells.

Up-Regulation of HLA-DR α-Chain and CIITA mRNA Expression in DDR1b-Overexpressing PMA-Treated THP-1 Cells Northern blotting with $^{32}$P-labeled HLA-DR α-chain cDNA probe was performed in order to determine whether the increased cell-surface HLA-DR expression on DDR1b-overexpressing cells cultured on collagen-coated plates was due to increased HLA-DR mRNA expression. Cells were cultured at a density of 5×10$^6$ cells/ml in RPMI 1640 containing 10% PCS in the presence of 10 nM PMA in collagen-coated or uncoated 6 well cluster tissue culture plates (Costar, Cambridge, Mass., 3 ml/well). Total RNA was extracted from each culture by using TRIzol Reagent. Northern blot analysis was performed as previously described (Yoshimura, *J. Immunol.* 150:5025 1993). Human HLA-DR α-chain and β-actin cDNAs were labeled with [α-$^{32}$P]dCTP by using rediprime II random prime labeling system (Amersham Pharmacia Biotech).

The expression of HLA-DR α-chain mRNA was up-regulated only in DDR1b-overexpressing cells at 12 hours. A study of the kinetics of HLA-DR α-chain mRNA expression revealed that the expression of HLA-DR α-chain mRNA was already elevated at 4 hours in DDR1b-overexpressing cells and the levels at 12 and 16 hours were about 5 times higher than that in other cells lines. This result was confirmed using two independent clones of DDR1a- or DDR1b-overexpressing THP-1 cells.

The expression of HLA DR α-chain mRNA is dependent on the expression of the class II transactivator (CIITA) (Beresford and Boss, *Nat. Immunol.* 2:652, 2001). Therefore, the effect of collagen-activation of PMA-treated DDR1b-overexpressing cells on CIITA mRNA expression was demonstrated. Total RNA was extracted from THP-1 cells treated with PMA and collagen for various times. First-strand cDNA synthesis was performed with 6 µg total RNA, 500 ng oligo-dT primer and Superscript RNase H-reverse transcriptase according to the manufacturer's direction. PCR was performed with a forward primer 5'-TTTCTGGGCACCCGC-CTCAC-3' (SEQ ID NO: 9) and a reverse primer 5'-CTGGGGGAAGGTGGCTGAGA-3' (SEQ ID NO: 10), specific for CIITA (564 bp). The primer pair, 5'-CGGATTTG-GTCGTATTGG-3' (SEQ ID NO: 11) and 5'-TCCTGGAA-GATGGTGATG-3' (SEQ ID NO: 12), specific for glyceraldehyde-3-phosphate dehydrogenase (GAPDH), was used as an internal control (294, bp). PCR conditions were as follows: 20, cycles of denaturation of 94° C. for 1 minute, annealing at 59° C. for 2 minutes, and extension at 72° C. for 2 minutes.

The expression of CIITA mRNA was detected by 5 hours after collagen-activation of DDR1b-overexpressing cells, but not in other cell lines. At 10 hours, all cell lines expressed mRNA for CIITA with or without collagen-activation. Thus, the expression of CIITA occurs much earlier in DDR1b-overexpressing cells than in other cell lines, although ultimately all cell lines actually express CIITA.

Phosphorylation of DDR1b and Shc in Collagen-Activated PMA-Treated DDR1b-Overexpressing THP-1 Cells The kinetics of DDR1 autophosphorylation in these cells was measured to demonstrate whether the differences in the cell proliferation and the expression of cell-surface molecules between DDR1a- and DDR1b-overexpressing cells is due to different DDR1 autophosphorylation patterns. Parental, mock, DDR1a- or DDR1b-overexpressing THP-1 cells were plated at 5×10$^6$/ml on uncoated tissue culture plates and stimulated with PMA (10 nM) for 24 hours, and then starved in RMPI 1640 without FCS for 10 hours. Subsequently cells were washed three times with PBS, and then incubated in the presence of 50 µg/ml collagen type I for various times.

Ten million cells were lysed on ice for 20 minutes in a buffer containing 50 mM NaCl, 20 mM Tris-HCl, 50 mM sodium fluoride, 30 mM Na$_4$P$_2$O$_7$, 5 mM EGTA, 3 mM sodium orthovanadate, 1% Triton X-100, 1 mg/ml leupeptin, 1 mM PMSF, 1 mg/ml aprotinin, 1 mg/ml pepstatinA and 100 µM sodium orthovanadate treated with H$_2$O$_2$. A lysis buffer containing 150 mM NaCl, 50 mM HEPES, 1% Triton-X 10% glycerol, 1 mM sodium fluoride, 1 mM EDTA, 2 mM sodium orthovanadate, 1 mg/ml leupeptin, 1 mM PMSF, 1 mg/ml aprotinin, 1 mg/ml pepstatinA and 100 µM sodium orthovanadate treated with H$_2$O$_2$, was also used for immunoprecipitation with anti-Shc Ab. The lysates were spun in a microcentrifuge for 20 minutes and the supernatants were collected. The samples were incubated with an approximately 20 µl packed volume of PGA for 1 hour at 4° C. After brief centrifugation, supernatants were collected, mixed with 1 µg/ml polyclonal anti-human DDR1 IgG, and incubated for 1 hour at 4° C. Twenty µl of PGS was then added and incubated for another 1 hour. IgG coupled PGA were washed with the washing buffer containing 50 mM Hepes, 150 mM NaCl, 0.1% Triton X-100, 10% glycerol three times, and 20 µl double-strength sample buffer (20% glycerol, 6% SCS, 10% 2-mercaptoetharol) was added. The samples were boiled for 10 minutes.

Eluted proteins were analyzed on 8% polyacrylamide gels by SDS-PAGE and transferred electrophoretically to nitrocellulose membranes at 150 mA for 1 hour by a semi-dry system. The membranes were incubated with either anti-DDR1 IgG, anti-phosphotyrosine IgG, or anti-human Shc IgG, followed by an appropriate secondary antibody coupled with horseradish peroxidase. Peroxidase activity was visualized by the Enhanced Chemiluminescence Plus Detection System (Amersham Pharmacia Biotech). To detect phosphorylated or nonphosphorylated p38 MAP kinase or ATF-2, 20 μl of cell lysates were directly mixed with 20 μl of sample buffer and then analyzed.

Autophosphorylation of DDR1a was first detected 90 minutes after collagen-activation. The level of phosphorylation slightly increased at 120 minutes, reached a peak at 4 hours, decreased at 8 hours, and became undetectable by 12 hours. In contrast, autophosphorylation of DDR1b was highly detectable as early as 30 minutes after collagen-activation, and reached a peak at 60 minutes. The level of DDR1b phosphorylation decreased at 90 minutes and returned to a basal level by 120 minutes.

In addition to tyrosine-phosphorylated DDR1b, another tyrosine-phosphorylated protein was detected around 46 kDa in DDR1b-overexpressing cells. Western blotting with anti-Shc antibody detected the presence of Shc in the same samples at the almost identical location as the 46 kDa protein band. Co-immunoprecipitation of DDR1b with Shc was further confirmed by immunoprecipitating Shc with anti-Shc antibody at high stringency. Since Shc was co-immunoprecipitated with DDR1b only when DDR1b was phosphorylated, the data indicate that the recruitment and phosphorylation of Shc were dependent on the activation of DDR1b by collagen.

Activation of p38 MAPK in PMA-Treated DDR1b-Overexpressing THP-1 Cells

Downstream signaling molecules that may play a role in the up-regulation of HLA-DR in collagen-activated PMA-treated DDR1b-overexpressing cells were identified in the following manner. Cells were incubated with collagen for 60 minutes since autophosphorylation of DDR1b was maximal at 60 minutes after collagen-activation. Several proteins were found to be tyrosine-phosphorylated after collagen-activation of each cell line. There were two tyrosine-phosphorylated bands that migrated to a molecular mass range between 30 and 50 kDa. By Western blotting, a 38 kDa protein was identified to be p38 MAP kinase. Phosphorylation of p38 MAP kinase was first detected 30 minutes after collagen activation of DDR1b-overexpressing cells and the level of phosphorylation increased thereafter. This delayed phosphorylation of p38 MAP kinase was probably due to the delayed kinetics of DDR1b autophosphorylation. Phosphorylation of p38 MAP kinase was not detected in DDR1a-overexpressing cells up to 120 minutes. The transcription factor ATF2, a substrate of p38 MAP kinase, was also phosphorylated in collagen activated PMA-treated DDR1b-overexpressing cells with delayed kinetics. To further confirm that the 38 kDa protein was p38 MAP kinase, p38 MAP kinase was immunoprecipitated with anti-p38, MAP kinase antibody and the membrane was blotted with anti-phosphotyrosine antibody. Phosphorylation of p38 MAP kinase was more evident 30 minutes following collagen activation and the level of phosphorylation was sustained for up to 120 minutes. Treatment of DDR1b-overexpressing cells with CHX before PMA-treatment completely inhibited the phosphorylation of p38 MAP kinase in response to collagen, indicating that protein synthesis is involved in the activation of p38 MAP kinase in these cells. Phosphorylation of other members of the MAP kinase family, ERK1, ERK2, and JNK could not be detected in collagen-activated PMA-treated DDR1b-overexpressing cells. The upstream MAP kinase kinases, MKK3 and MKK6, were absent in these cells, as previously reported (Benoist and Mathis, *Annu. Rev. Immunol.* 8:681, 1990).

Effect of p38 MAP Kinase Inhibitor SB203580, on the Expression of HLA-DR in Collagen-Activated PMA-Treated DDR1b-Overexpressing THP-1 Cells To demonstrate whether the increased HLA-DR expression in collagen-activated PMA-treated DDR1b-overexpressing cells was due to activation of p38 MAP kinase, DDR1b-overexpressing TIP-1 cells ($5 \times 10^6$/ml) were incubated in RPMI 1640 containing 10% FCS with 10 nM PMA plus collagen for 12 hours. The cells were then rinsed three times with RPMI 1640 containing 10% FCS, and incubated either with the p38 MAP kinase inhibitor SB203580, the the MEK (MAP or ERK kinase) ½ inhibitor PD98059, or dimethylsulfoxide (DMSO) for 30 minutes, followed by an additional 12 hour incubation in the presence of 10 nM PMA plus collagen. The expression of HLA-DR was analyzed by flow cytometry.

SB203580, dose-dependently inhibited the expression of HLA-DR at 24 hours, whereas PD98059, showed no effect. Thus, HLA-DR expression in collagen-activated PMA-treated DDR1b-overexpressing cells at 24 hours was due to the activation of p38 MAP kinase pathway.

Activation of DDR1 Induces Phosphorylation of p38 MAP Kinase and Subsequent HLA-DR Expression in Human GM-Macrophages In order to demonstrate whether the activation of DDR1b induces the phosphorylation of p38 MAP kinase and the subsequent differentiation of primary macrophages human peripheral blood mononuclear cells (PBMC) were isolated from leukapheresis preparations obtained by the Blood Bank, Clinical Center, National Institutes of Health (Bethesda, Md.). The leukocyte-rich preparation was overlaid on Accuprep in 50 ml tubes and the tubes were centrifuged at 800×g for 20 minutes at room temperature. PBMC fractions were collected, washed once with PBS at room temperature and twice with complete medium at 4° C. and resuspended in the same medium. Monocytes were further purified by using iso-osmotic Percoll gradient. At this stage, the purity of monocytes was higher than 90%. The cells ($5 \times 10^5$/ml) were allowed to adhere to the surface of 6-well plates. After a 5-hour incubation at 37° C., nonadherent cells were removed and adherent cells were induced to differentiate into macrophages by incubation in the presence of GM-CSF (50 ng/ml) for 5 to 7 days to produce GM-CSF-induced macrophages (GM-macrophages). Five-day GM-macrophages were incubated for additional 2 days with GM-CSF in the presence of an agonistic anti-human DDR1 monoclonal mouse against the extracellular domain of DDR1 (IgM 513). To measure the effect of SB203580, 5-day GM-macrophages were pretreated with SB203580, for 30 minutes.

The antibody preparation did not contain a detectable level of lipopolysaccharide (LPS) that is often found in commercially available collagen preparations (Suri and Austyn, *J. Immuno. Methods* 214:149, 1998), including the ones used in this study. Since LPS is a potent activator of macrophages, contamination of LPS could affect the outcome of the study. The expression of both DDR1a and DDR1b was induced during the differentiation of GM-macrophages. DDR1a was mainly expressed in an early stage of differentiation (1-4 days), whereas DDR1b expression was maximal in a late stage (5-7 days). Five-day GM-macrophages that mainly expressed DDR1b were used for the rest of the study.

Autophosphorylation of DDR1 (DDR1a+DDR1b) in response to agonistic antibody, but not to control antibody, was first detected at 30 minutes and continued up to 120 minutes. As in collagen-activated PMA-treated DDR1b-overexpressing THP-1 cells, tyrosine-phosphorylated Shc was co-immunoprecipitated with DDR1, and phosphorylation of p38 MAP kinase was detected in response to the agonistic antibody, but not with control antibody. Although MKK3/6 were present in GM-macrophages, phosphorylation of these kinases was not induced in response to agonistic anti-DDR1 antibody.

The expression of HLA-DR on GM-macrophages was also measured. Only 2% of freshly isolated monocytes expressed HLA-DR. Approximately 17% of 5-day GM-macrophages expressed HLA-DR and the percentage of HLA-positive cells increased to 39% when the cells were further incubated with agonistic antibody. Incubation with control IgM did not change the percentage of HLA-DR-positive cells. Pretreatment of 5-day GM-macrophages with SB203580, but not with DMSO, completely inhibited the agonistic antibody-induced increase of HLA-DR-positive cells. These results indicate that activation of DDR1, potentially DDR1b, up-regulates the expression of HLA-DR through activation of p38 MAP kinase in primary macrophages.

Example 3

Interaction of DDR1b with Collagen of the Extracellular Matrix Facilitates Macrophage Expression and Production of Cytokines and Chemokines through Activation of the p38 Mitogen Activated Protein Kinase Pathway Reagents A mouse monoclonal anti-β1-integrin blocking antibody was obtained from Upstate Biotechnology (Lake Placid, N.Y.). A mouse monoclonal anti-human IL-1β antibody was from R&D Systems (Minneapolis, Minn.). [$\alpha$-$^{32}$P]dCTP and [$\alpha$-$^{32}$P]dCTP were from Amersham (Arlington Heights, Ill.). The sources of human MCP-1, IL-8, and MIP-1α cDNAs were previously described (Yoshimura et al., *FEBS Letters* 244:487-493, 1989; Yamashiro et al., *J. Leukoc. Biol.* 65: 671-679, 1999). Human β-actin cDNA was from Clontech (Palo Alto, Calif.). Phosphate buffered saline (PBS), RPMI-1640, G418, and TRIZOL Reagent were from Invitrogen (Gaitherburg, Md.). FCS was from HyClone (Logan, Utah). Paraformaldehyde, formamide, human serum, propidium iodide, PMA and bovine collagen type I solution were from Sigma (St Louis, Mo.). SB203580, and CAPE were from Biochem-Novabiochem (San Diego, Calif.). The NF-κB-Luc plasmid containing four copies of the NF-κB site of the Ig κ-chain gene and the luciferase gene was obtained from Stratagene (La Jolla, Calif.). A mouse monoclonal anti-IκB antibody was obtained from Santa Cruz Biotechnology (Santa Cruz, Calif.). Accu-prep was from Accurate Chemical & Scientific Corp. (Westbury, N.Y.).

DDR1a-Overexpressing, DDR1b-Overexpressing, and Mock THP-1 Cells

The production of DDR1a- or 1b-overexpressing THP-1 cells was previously described (Kamohara et al., *FASEB J.* 15:2724, 2001). Briefly, the human monocytic leukemia cell line, THP-1, was transduced with control retrovirus containing the vector only (mock-transduced) or retrovirus expressing DDR1a or DDR1b. THP-1 cells transduced by each virus were selected with G418, and cloned by limiting dilution. The cloned THP-1 cells were maintained in RPMI 1640 medium supplemented with 100 µg/ml gentamycin and 10% FCS (complete medium). Cells were plated at $1 \times 10^6$/ml and treated with PMA (10 nM) for variable times on uncoated or collagen-coated tissue culture plates for quantification of cytokine or chemokine release.

Collagen-Activation of DDR1b Up-Regulates the Expression and Production of MCP-1 in PMA-Treated THP-1 Cells The effect of collagen-activation on the expression of MCP-1 mRNA in PMA-treated parental, mock-transduced, DDR1a-overexpressing, and DDR1b-overexpressing THP-1 cells was measured by Northern blotting. THP-1 cells were cultured at the cell density of $5 \times 10^6$, cells/ml in the complete medium in the presence of 10 nM PMA in 6 well tissue culture plates that were either uncoated or collagen-coated. Total RNA was extracted from each culture by using TRIzol reagent® and Northern blot analysis was performed as described (Yoshimura, *J. Immunol.* 150:5025, 1993). IL-1β cDNA was obtained by RT-PCR from a human monocyte cDNA library using the following primer pair: sense primer 5'-CGTATGGCAGGACAAATGCTTCTTC-3' (SEQ ID NO: 13) and anti-sense primer 5'-TTCCCTCCAGGCTGC-CATGAG-3' (SEQ ID NO: 14). Each cDNA was labeled with [$\alpha$-$^{32}$P]dCTP using Rediprime™ II random prime labeling system (Amersham Pharmacia Biotech).

In parental cells, a significant level of MCP-1 mRNA was detected at 16 hours and then the expression level rapidly increased. The slow kinetics of MCP-1 mRNA expression in PMA-treated parental cells were consistent with previous data (Ueda et al., *J. Biol. Chem.* 272:1092, 1997) indicating that collagen-activation had no effect on the parental cells. The kinetics and the level of MCP-1 mRNA expression in mock transduced and DDR1a-overexpressing cells were similar to that in parental cells on either uncoated or collagen-coated plates, although the expression of MCP-1 mRNA was slightly upregulated at 4, hours. In contrast, the level of MCP-1 mRNA expression was rapidly up-regulated in PMA-treated DDR1b-overexpressing cells on collagen-coated plates, reached a peak by 12 hours, and the peak expression level was sustained up to 48 hours.

In addition, the concentration of MCP-1 in the culture supernatant of each cell line was measured by ELISA. The concentration of MCP-1 was measured in the Lymphokine Testing Laboratory, Clinical Services Program, SAIC-Frederick (Frederick, Md.) by using an enzyme-linked immunosorbent assay (ELISA) kit (R&D Systems, Minneapolis, Minn.) specific for the chemokine.

Consistent with the Northern data, similar levels of MCP-1 were detected in PMA-treated parental, mock-transduced, and DDR1a-overexpressing cells, but there was no increase in MCP-1 concentration when these cells were incubated on collagen-coated plates. PMA-treated DDR1b-overexpressing cells also released a similar level of MCP-1 on uncoated plates. However, these cells released approximately 7-fold higher amounts of MCP-1 on collagen-coated plates. Addition of anti-β1 integrin antibody did not decrease the MCP-1 concentrations detected in the culture supernatants, indicating that the increased MCP-1 release was not dependent on the interaction between β1 integrins and collagen. There was no difference in the cell viability between the cell lines. These data strongly indicated that the interaction of DDR1b with collagen facilitated the expression and production of MCP-1 in PMA-treated THP-1 cells.

Collagen Activation of DDR1b Up-Regulates Tile Expression and Production of IL-8 MIP-1α; and IL-1β in PMA-Treated THP-1 Cells To demonstrate whether the expression of other proinflammatory cytokine and chemokines are also up-regulated in collagen-activated PMA-treated THP-1 cells, a cDNA array analysis was performed. Expression of cytokine mRNA was examined by using the Human Atlas cDNA Expression Arrays (Clontech, Palo Alto, Calif.) according to the manufacture's protocol. Briefly, total RNA was isolated from mock-transduced or DDR1b-overexpressing THP-1 cells that were incubated with PMA for 12 hours on collagen-coated plates. Approximately 500 μg of pooled total RNA from each cell line were treated with DNase I (50 U/ml), and then Poly A$^+$RNA was purified on oligotex spin columns (Qiagen, Valencia, Calif.). Five hundred ng of each Poly A$^+$RNA was used to synthesize $^{32}$P-labeled first-strand cDNA. Each Atlas array was prehybridized in 15 ml of ExpressHyb containing 100 μg/ml of heat-denatured sheared salmon sperm DNA at 68° C. for 30 minutes. The array was then hybridized in 5 ml of freshly prepared prehybridization solution containing 5×10$^5$ cpm/ml of $^{32}$P-labeled cDNA probe and Cot-1 DNA at 68° C. overnight. After hybridization, the array was washed with 2×SSC, 1% SDS at 68° C. for 20 minutes four times, followed with 0.1×SSC, 0.5% SDS at 68° C. for 20 minutes twice, and then exposed to Kodak XR5 films at −80° C. for 1-3 days.

In addition to MCP-1 mRNA, the expression of IL-1β and MIP-1α mRNA was markedly up-regulated in collagen-activated PMA-treated DDR1b-overexpressing cells at 12 hours. The expression of IL6 mRNA was slightly up-regulated. The expression levels of IL-8 mRNA were similar in both cells lines.

The expression of IL-1β, IL-8, and MIP-1α mRNA was next measured by Northern blotting. Consistent with the cDNA array result, the expression of IL-1β and MIP-1α mRNA was rapidly induced in collagen-activated PMA-treated DDR1b-overexpressing cells, and the expression levels in these cells were much higher than that in other cell lines at 12 hours. The peak expression level of MIP-1α mRNA was sustained up to 24 hours, whereas the expression level of IL-1β rapidly declined at 20 hours. Although significant up-regulation of IL-8 mRNA expression was not seen in DDR1b-overexpressing cells by the cDNA analysis, Northern blotting revealed that the expression of IL-8 mRNA was also rapidly up-regulated in DDR1b-overexpressing cells and the peak expression level was sustained up to 24 hours.

Figure 6:
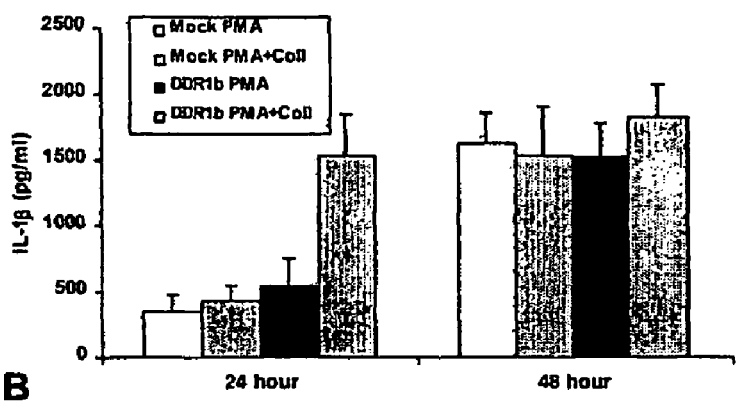
FIG. 6 is a series of graphs demonstrating the release of IL-1β (FIG. 6A), IL-8 (FIG. 6B), and MIP-1α(FIG. 6B) from collagen-activated PMA-treated parental, mock-transduced, DDR1a- or DDR1b-overexpressing THP-1 cells.
Figure 6:
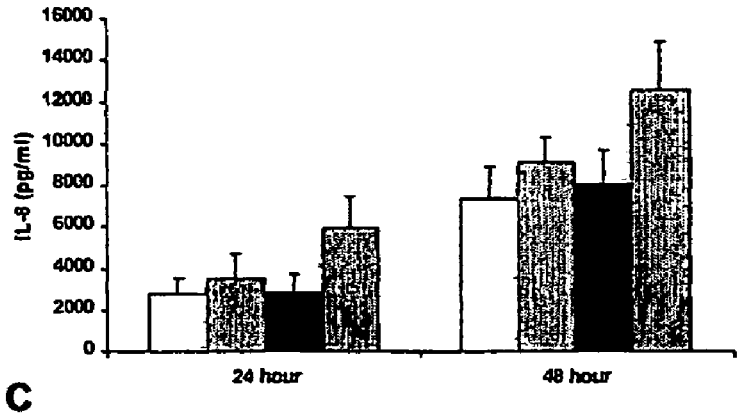
Figure 6:
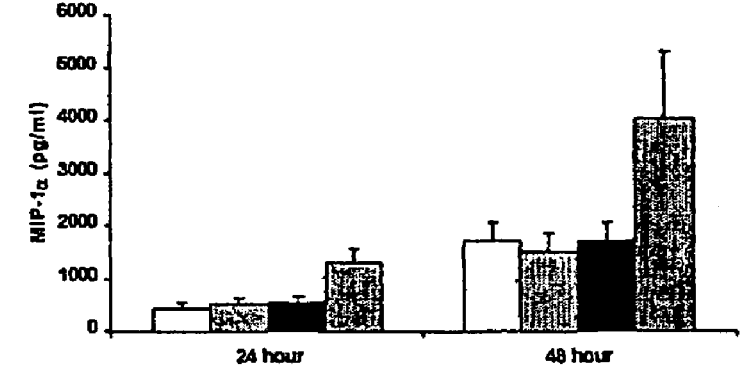

In addition, the concentrations of IL-1β, IL-8, and MIP-1α in the culture supernatants of each cell line were quantified by ELISA (FIG. 6). The concentration of IL-1β, IL-8, and MIP-1α were measured in the Lymphokine Testing Laboratory, Clinical Services Program, SAIC-Frederick (Frederick, Md.) by using enzyme-linked immunosorbent assay (ELISA) kits (R&D Systems, Minneapolis, Minn.) specific for each human cytokine and chemokine. The concentration of IL-1β in the supernatants of DDR1b-overexpressing cells was significantly higher than that in the culture supernatants of other cell lines at 24 hours, but there was no significant difference at 48 hours. This was consistent with the mRNA expression data that showed only a shift in the kinetics. The concentrations of IL-8 and MIP-1α were significantly higher in the culture supernatants of DDR1b-overexpressing cells at 24 and 48 hours in comparison with other cell lines. IL-1β is known to induce the expression of MCP-1, IL-8, and MIP-1α (Baggiolini et al., Adv. Immunol. 55:97-179, 1993), thus the effect of early production of IL-1β on the increased production of these chemokines was demonstrated by adding a neutralizing antibody against IL-1β to the cultures. The concentrations of these chemokines in the culture supernatants of DDR1b overexpressing THP-1 cells were not changed in the presence of the antibody, indicating that the rapid up-regulation of these chemokines in DDR1b-overexpressing cells was independent of IL-1β released by the same cells.

Increased IκB Degradation and NF-κB Nuclear Translocation in Collagen-Activated PMA-Treated DDR1b-Overexpressing THP-1 Cells Mock-transduced and DDR1b-overexpressing THP-1 cells were plated at 5×10$^6$ cells/ml and treated with 10 nM PMA on collagen-coated plates for varous times. Ten million cells were lysed on ice for 20 minutes in a buffer containing 50 mM NaCl, 20 mM Tris-HCl, 50 mM sodium fluoride, 30 mM Na$_4$P$_2$O$_7$, 5 mM EGTA, 3 mM sodium orthovanadate, 1% Triton X-100; 1 mg/ml leupeptin, 1 mM PMSF, 1 mg/ml aprotinin, 1 mg/ml pepstatin A and 100 μM sodium orthovanadate in H$_2$O$_2$ The lysates were spun and the supernatants were collected. Each sample was boiled in double-strength sample buffer for 10 minutes, electrophoresed on 10% polyacrylamide gels by SDS-PAGE, and transferred electrophoretically to nitrocellulose membranes at 150 mA for 1 hour by a semi-dry system. The membranes were incubated with mouse monoclonal anti-IκB antibody followed by sheep anti-mouse IgG coupled with horseradish peroxidase. Peroxidase activity was visualized by the Enhanced Chemiluminescence Detection System (Amersham).

The level of IκBα in mock-transduced cells was unchanged in response to collagen. However, in DDR1b-overexpressing cells the amounts of Iκbα decreased at 2 and 3 hours, and then increased to the original level, which is typical for IκBα degradation.

Nuclear translocation of NF-κB was examined by EMSA. Nuclear extracts were prepared by a method previously reported (Ueda et al., J. Biol. Chem. 272:31092, 1997), and aliquots were frozen at −80° C. For EMSA, end-labeled $^{32}$P-oligonucleotide probes corresponding to the NF-KB binding site of the Ig κ-chain (5'-AGTTGAGGGGACTITC-CCAGGC-3') (SEQ ID NO: 15) or MCP-1 (A2 site; 5'-AGAGTGGGAATTTCCACTCA-3') (SEQ ID NO: 16) gene were used. Each probe was incubated with 5 μg of nuclear extracts in 20 μl of binding cocktail (50 mM Tris-HCl, pH 7.4, 25 MM MgCl$_2$, 0.5 mM DTT, 50% glycerol) at 4° C. for 15 minutes. The DNA-protein complexes were resolved on a 5% polyacrylanide gel. The dried gels were exposed to X-ray films.

A low level of NF-κB/DNA complex was detected with nuclear extracts of mock-transduced cells and this level was not significantly changed after stimulation with collagen, PMA, or collagen plus PMA. Similar levels of NF-κB/DNA complex was also detected with nuclear extracts of DDR1b-overexpressing cells incubated in complete medium or stimulated with collagen or PMA. However, when the cells were incubated with PMN on collagen-coated plates, the amount of NF-κB/DNA complex was significantly increased. The increased binding was not affected by a p38 MAP kinase inhibitor, SB203580, but completely abolished by a NF-κB inhibitor, CAPE.

To demonstrate whether this increased nuclear translocation of NF-κB was responsible for the up-regulated expression of MCP-1 mRNA, a luciferase assay with plasmids containing the sequences of NF-κB binding sites of either the human Ig-κ chain or MCP-1 genes (pGLM-Enh) was performed. Mock-transduced or DDR1b-overexpressing THP-1 cells were transfected with 10 μg of the NF-κB-Luc plasmid, pGL-ENH, or pGL-MA1MA2 and 5 μg of pSV-β-galactosidase plasmid DNA (Promega, Madison, Wis.) per 100-mm tissue culture plate using Effectene Transfection Reagent (Qiagen, Valencia, Calif.) according to the manufacture's protocol. After a 12 hour incubation, cells were rinsed with PBS and then incubated with 10 nM PMA on collagen-coated plates in the presence of absence of SB203580 or CAPE for another 12 hours. Cells were collected and lysed using the Reporter Lysis Buffer (Promega, Madison, Wis.) according to the manufacture's protocol. Luciferase activity and β-galactosidase activities were measured according to the protocol provided by the manufacturer. The resulting luciferase activity was corrected based on the β-galactosidase activity in the same cell extract. Empty vectors were used as a control.

Figure 7:
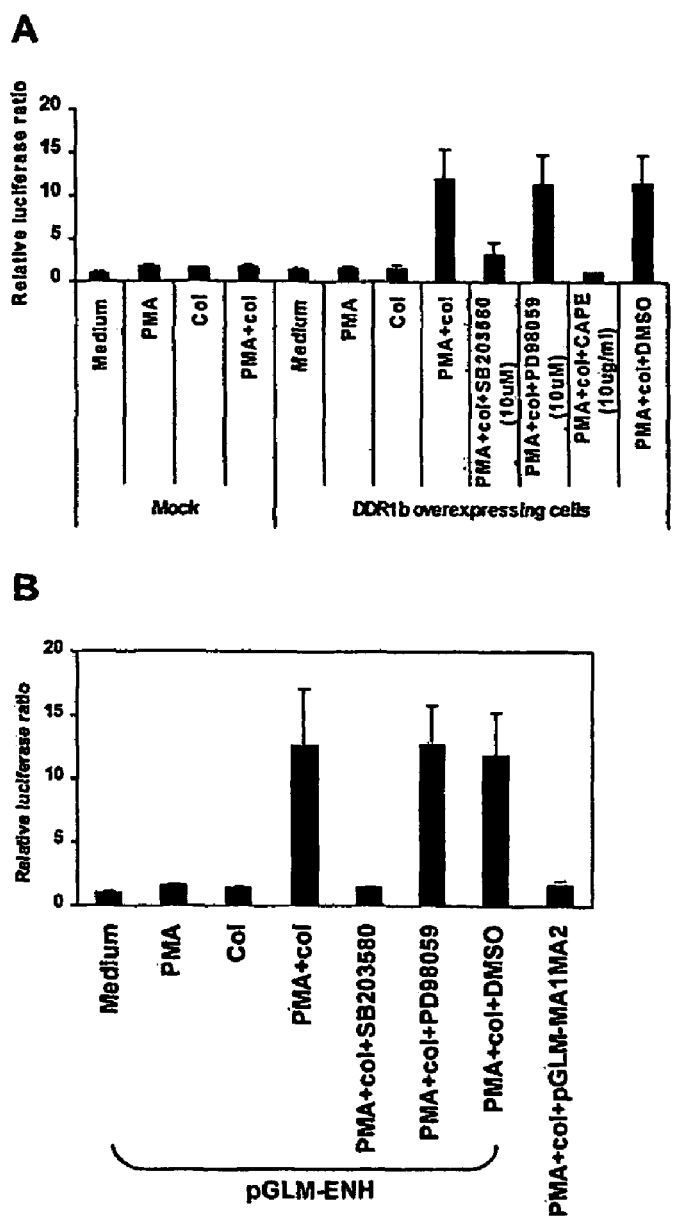
FIG. 7 is a series of graphs demonstrating the increased NF-κB enhancer activity in collagen-activated phorbol 12-myristate 13-acetate (PMA)-treated DDR1b-overexpressing THP-1 cells. For the results shown in FIG. 7A, mock-transduced or DDR1b-overexpressing THP-1 cells were transfected with 10 μg of the NF-κB-Luc plasmid and 5 μg of pSV-β-galactosidese plasmid DNA (Promega, Madison, Wis.) per 100-mm tissue culture plate using Effectene Transfection Reagent (Qiagen, Valencia, Calif.), according to the manufacture's protocol. After a 12-hour incubation, cells were rinsed with phosphate buffered saline (PBS) and then incubated with 10 nM PMA on collagen-coated plates in the presence of absence of SB203580, PD98059, CAPE or dimethylsulfoxide (DMSO) for another 12 hours. Cells were collected and lysed using the Reporter Lysis Buffer (Promega, Madison, Wis.), and luciferase activity and β-galactosidase activities were measured according to the protocol provided by the manufacturer. The resulting luciferase activity was corrected based on the β-galactosidase activity in the same cell extract. For the results shown in FIG. 7B, DDR1b-overexpressing THP-1 cells were transfected with 10 μg of the pGLM-ENH, or pGLM-MA1MA2 (Ueda et al., J. Bio. Chem. 272: 31092-9, 1997) and 5 μg of pSV-β-galactosidese plasmid DNA (Promega, Madison, Wis.) per 100-mm tissue culture plate using Effectene Transfection Reagent (Qiagen, Valencia, Calif.) according to the manufacture's protocol. After a 12-hour incubation, cells were rinsed with PBS and then incubated with 10 nM PMA on collagen-coated plates in the presence of absence of SB203580, PD98059, or DMSO for another 12 hours. Cells were collected and lysed using the Reporter Lysis Buffer (Promega, Madison, Wis.), and luciferase activity and β-galactosidase activities were measured according to the protocol provided by the manufacturer. The resulting luciferase activity was corrected based on the β-galactosidase activity in the same cell extract.

As shown in FIG. 7A, in mock-transduced cells there was no increase in luciferase activity in response to PMA, collagen, or PMA plus collagen. However, in DDR1b-overexpressing cells, luciferase activity was markedly increased in response to PMA plus collagen, which was dose-dependently inhibited by SB203580. CAPE also completely inhibited the increase induced by PMA plus collagen. Almost identical results were obtained with pGLM-Enh as shown in FIG. 7B. There was no increase in luciferase activity when pGLMA1MA2 that contained mutations in both NF-κB sequences was used. These results indicated that the increased expression of MCP-1 mRNA in collagen-activated PMA-treated DDR1b-overexpresing THP-1 cells was due to activation of NF-κB and p38 MAP kinase that resulted from the interaction between DDR1b and collagen.

Figure 8:
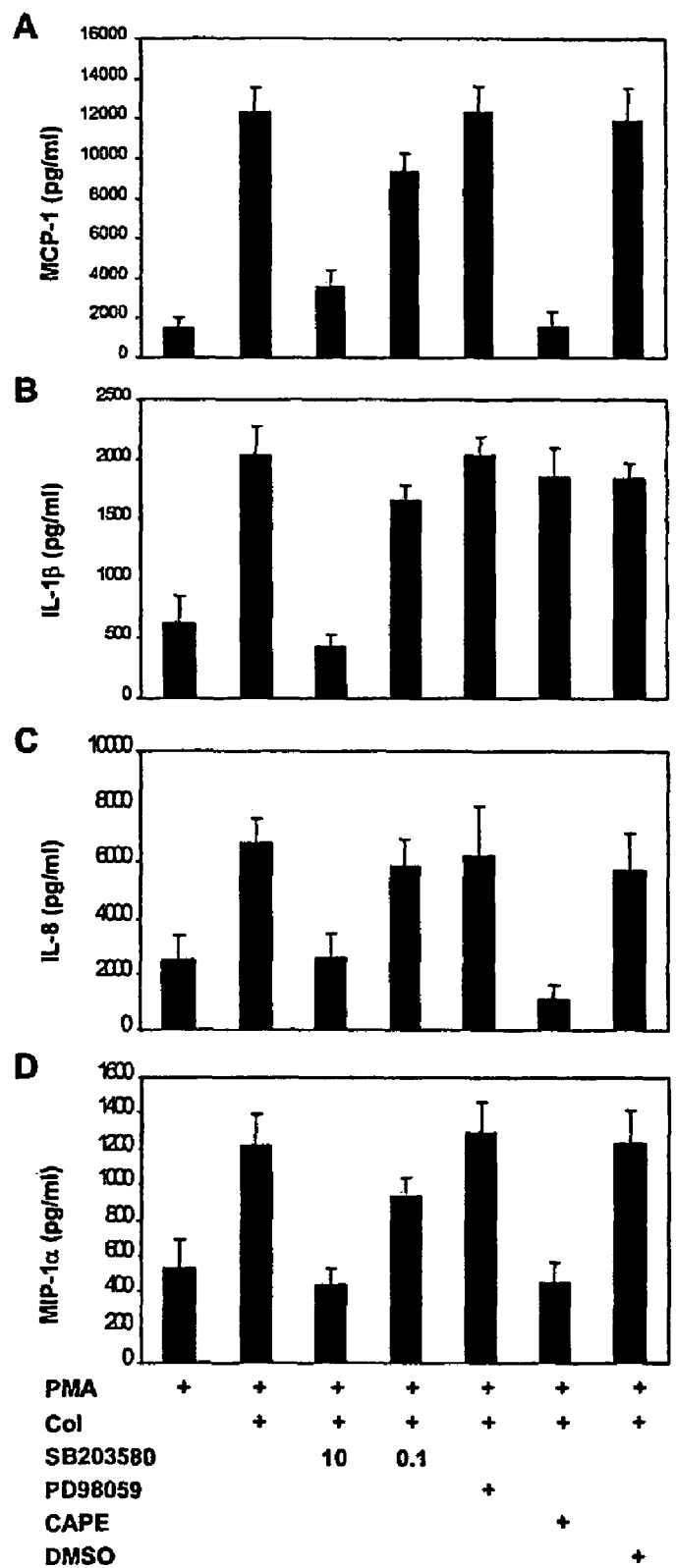
FIG. 8 is a series of graphs demonstrating that the release of MCP-1 (FIG. 8A), IL-1β (FIG. 8B), IL-8 (FIG. 8C), and MIP-1α (FIG. 8D) from collagen-activated PMA-treated DDR1b-overexpressing THP-1 cells is dependent on p38 MAP kinase and NF-κB.

SB203580, and CAPE Inhibit the Production of Cytokines by Collagen-Activated PMA-Treated DDR1b Overexpressing THP-1 Cells To further demonstrate the role of p38 MAP kinase and NF-κB in the up-regulated production of MCP-1, IL-1β, IL-8 and MIP-1α by collagen activated PMA treated DDR1b overexpressing cells, DDR1b-overexpressing THP-1 cells were incubated in the presence or absence of SB203580, or CAPE with PMA on collagen-coated plates for 48 hours, and the concentration of each protein was measured by ELISA. As shown in FIG. 8, SB203580, inhibited collagen-induced up-regulation of MCP-1, IL-1β, IL-8, and MIP-1α release, whereas PD98059, a MEK inhibitor, had no effect. CAPE also inhibited the release of MCP-1, IL-8, and MIP-1α, but not IL-1β. These results indicated that the interaction of DDR1b with collagen up-regulated the production of these three chemokines through activation of p38 MAP kinase and NF-κB. Up-regulation of IL-1β production was also dependent on the activation of p38 MAP kinase, but independent of NF-κB activation.

Activation of DDR1 Induces the Production of MCP-1 in Monocyte-Derived Macrophages Macrophages were prepared in vitro by incubating human blood monocytes with GM-CSF. Human PBMC were obtained from leukapheresis preparations obtained by the Blood Bank, Clinical Center, National Institute of Health (Bethesda, Md.). The leukocyte-rich preparation was overlaid on Accu-prep in 50 ml tubes and the tubes were centrifuged at 800×g for 20 minutes at room temperature. PBMC fractions were collected, washed once with PBS at room temperature and twice with complete medium at 4° C. and resuspended in the complete medium. Monocytes were further purified by using iso-osmotic Percoll gradient. At this stage, the purity of monocytes was higher than 90%. The cells ($5\times10^5$/ml) were allowed to adhere to the surface of 6 well plates. After a 5 hour incubation at 37° C., nonadherent cells were removed and adherent cells were cultured in the presence of GM-CSF (50 pg/ml) for 7 days to produce monocyte-derived macrophages. The monocyte-derived macrophages were stimulated with either collagen, DDR1-activating anti-DDR1 mouse monoclonal antibody, or control mouse IgM. After a 48 hour stimulation, the supernatants were collected to measure MCP-1 concentration.

GM-CSF-induced macrophages (GM-macrophages) were previously found to have features of alveolar macrophages (Akagawa *Int. J. Hematol.* 76:27, 2002). GM-macrophages expressed both DDR1a and DDR1b. When GM-macrophages were incubated in complete medium, only low levels of MCP-1 were detected in the culture supernatants. However, these cells released 7-fold higher levels of MCP-1 in response to DDR1-activating mouse monoclonal antibody. L up-regulated the release of MCP-1 by GM-macrophages, and addition of anti-DDR1 antibody further up-regulated the release of MCP-1 in concert with LPS.

Example 4

DDR1 is Responsible for Collagen-Mediated Phenotypic and Functional Maturation of Monocyte-Derived Human Dendritic Cells Reagents A rabbit polyclonal antibody against human DDR1 (C-20) and a mouse monoclonal Ab against human Shc were obtained from Santa Cruz Biotechnology (Santa Cruz, Calif.). A mouse monoclonal antibody against phosphotyrosine (4G10) was obtained from Upstate Biotechnology (Lake Placid, N.Y.). Rabbit polyclonal antibodies against phosphorylated or non-phosphorylated P38 MKK3/MKK6, ATF2, SPARK/JNK, or ERK were from Cell Signaling Technology (Beverly, Mass.). Sheep anti-mouse or rabbit IgG coupled with horseradish peroxidase were from Amersham Pharmacia Biotech, Inc. (Pascataway, N.J.). Mouse monoclonal antibodies against CD80, CD83, CD86, or HLA-DR, and a mouse monoclonal IgM were from PharMingen (SanDiego, Calif.). Tritium-thymidine was obtained from Amersham (Arlington Heights, Ill.). PBS, RPMI-1640, G418, recombinant protein G-agarose (PGA), and TRIzoL, Reagent were obtained from Invitrogen (Gaithersburg, Md.). FCS was from HyClone (Logan, Utah). Lipopolysaccharide (LPS), paraformaldehyde, formamide, human serum and propidium iodide (PI) were from Sigma (St Louis, Mo.). Human recombinant GM-CSF, IL-4 and TNF-α were from Pepro-Tech Inc. (Rocky Hill, N.J.). SB203580, was obtained from Biochem-Novabiochem (San Diego, Calif.).

Preparation of DDR1 Antibodies

Rabbit polyclonal antibodies specific for DDR1a or DDR1b were raised against a synthetic peptide (CVPNG-SAYSGDY; SEQ ID NO: 6) found only in DDR1a, or two overlapping peptides (CARPPRGPGPPTPAWAK; SEQ ID NO: 7) and (PRGPGPPTPAWAKPTNC; SEQ ID NO: 8) that are found only in DDR1b. The peptides were coupled to KLH before injection into rabbits. Specific antibodies were affinity-purified from immune sera by purification over matrix-bounded peptides (UltraLink columns, Pierce) according to standard procedures. The specificity of the antibody was demonstrated by Western blotting using cell lysates of DDR1a- or DDR1b-overexpressing THP-1 cells and GST-fusions of DDR1a and DDR1b intracellular domains. Mouse monoclonal anti-DDR1 IgM (513) was raised against the entire extracellular domain of DDR1. The antibody was produced by growing the hybridoma cells (513GA12) in protein-free medium (Protein Free Hybridoma Medium, GIBCO/

Invitrogen). The isotype of the antibody produced is IgM. This antibody has the capacity to induce autophosphorylation of DDR1.

Preparation of Human Monocyte-Derived DCs

Human PBMC were isolated from leukapheresis preparations obtained by the Blood Bank, Clinical Center, National Institutes of Health (Bethesda, Md.). The leukocyte-rich preparation was overlaid on Accu-prep in 50 ml tubes and the tubes were centrifuged at 800×g for 20 min at room temperature. PBMC fractions were collected, washed once with PBS at room temperature and twice with complete medium at 4° C. and resuspended in the same medium. Monocytes were further purified by using iso-osmotic Percoll gradient. At this stage, the purity of monocytes was higher than 90%. The cells ($5 \times 10^5$/ml) were allowed to adhere to the surface of 6-well plates. After a 5 hour incubation at 37° C., non-adherent cells were removed, and remaining adherent cells were subjected to the DC (Baggiolini et al., Adv. Immunol. 55:97-179, 1993). Over 95% of the adherent cells were positive for CD14 by flow cytometry analysis. Monocytes were briefly resuspended at a concentration of $1 \times 10^6$ cells/ml and cultured in complete medium containing 50 ng/ml GM-CSF and 50 ng/ml IL-4. Cells were cultured for 7 days, with cytokine added every second day, to obtain a population of immature monocyte-derived dendritic cells (DC). For maturation, immature DC (iDC) were treated with TNF-α (50 ng/ml) from day 5 to day 7. Mouse monoclonal anti-DDR1 antibody (513) (5 μg/ml) was used to specifically activate DDR1. Unrelated mouse monoclonal IgM was used as a control.

Expression of DDR1a and DDR1b is Induced During DC Maturation

Monocytes were incubated in the presence of IL-4 and GM-CSF for 5 days to produce iDCs, and then for an additional 2 days in the presence of IL-4, GM-CSF, and TNF-α to produce mature DCs (mDCs). To detect the DDR1 isoformns expressed by DC, cells were harvested on each day of the experiment, DDR1 was immunoprecipitated from the cell lysates, and the expression of DDR1a, DDR1b, and total DDR1 was determined by Western blotting.

Cells were washed three times with PBS, and $1 \times 10^7$, cells were lysed on ice for 20 minutes in 1 ml of lysis buffer containing 50 mM NaCl, 20 MM Tris-HCl, 50 mM sodium fluoride, 30 mM $Na_4P_2O_7$, 5 mM EGTA, 3 mM sodium orthovanadate, 1% Triton X-100, 1 mg/ml leupeptin, 1 mM PMSF, 1 mg/ml aprotinin, 1 mg/ml pepstatinA and 100 μM sodium orthovanadate in $H_2O_2$. The lysates were spun and the supernatants were collected and stored at −80° C. until use. The samples were incubated with an approximately 20 μl packed volume of PGA for 1 hour at 4° C. After centrifugation, supernatants were collected, mixed with 1 μg/ml polyclonal anti-human DDR1 antibody (C-20), and incubated for 1 hour at 4° C. Twenty μl of PGA were then added, and the samples were incubated for an additional 12 hours. IgG-coupled PGA was washed with the washing buffer containing 50 mM Hepes, 150 mM NaCl, 0.1% Triton X-100, 10% glycerol buffer three times, and 20 μl double-strength sample buffer (20% glycerol, 6% SDS, 10% 2-mercaptoethanol) was added. The samples were boiled for 10 minutes.

Eluted proteins were analyzed on 8% polyacrylamide gels by SDS-PAGE and transferred electrophoretically to nitrocellulose membranes at 150 mA for 1 hour by a semi-dry system. The membranes were incubated with various rabbit IgGs that recognize either only DDR1a, only DDR1b, or both forms of DDR1 (C-20), followed by sheep anti-rabbit IgG coupled with horseradish peroxidase. Peroxidase activity was visualized by the Enhanced Chemiluminescence Detection System (Amersham).

A high level of DDR1a was already expressed on day 1. The level of DDR1a reached a peak on day 2 and gradually decreased thereafter. In contrast, the level of DDR1b gradually increased, and reached the highest level on day 7. Since total DDR1 levels were similar between day 3 and day 7 it appears that DDR1a is the dominant isoform in an early stage of DC maturation, whereas DDR1b becomes the dominant isoform in mDCs.

Activation of DDR1 Promotes Phenotypic Maturation of DCs

Monocytes were plated at a density of $5 \times 10^6$ cell/ml and incubated for 5 days in the presence of 50 ng/ml GM-CSF and 50 ng/ml IL-4. Cells were cultured for 7 days, with cytokine added every second day, to obtain a population of immature monocyte-derived DCs. For maturation, iDCs were incubated with TNF-α (50 ng/ml) from day 5 to day 7. For activation of DDR1 on DCs, the cells were incubated in the presence of either agonistic anti-DDR1 IgM (513) or control IgM, and the expression of CD80, CD83, CD86, and HLA-DR was measured using a flow cytometer.

A hundred thousand cells were resuspended in 50 μl of cold PBS containing 0.1% sodium azide, 10 ng/ml bovine serum albumin (BSA) and 200 μg/ml of human IgG, and then incubated for 10 minutes on ice. Subsequently, the cells were incubated with antibodies against CD80, CD83, CD86 or HLA-DR for 15 minutes on ice, and followed by washing with PBS. After washing, cells were incubated with FITC-conjugated goat anti-mouse IgG for 15 minutes on ice. At the end of the incubation, PI was added to 100 μM. Cells were washed by PBS, and subsequently analyzed on a FACscan (Becton Dickinson). Dead cells, determined by their PI-staining, were gated out. Results were processed using CellQuest software (Becton Dickinson). For the experiments of p38 MAP kinase inhibition, iDC were pre-treated with SB203580, or DMSO for 30 minutes, and then cultured with TNF-α alone, TNF-α plus 513 agonistic anti-DDR1 IgM (5 μg/ml), or TNF-α plus control IgM (5 μg/ml). These experiments were repeated with cells from three different donors.

DDR1 activation significantly up-regulated the cell-surface expression of CD83, and CD86, but not of CD80, or HLA-DR, in iDCs. When TNF-α was used to induce DC maturation, the expression of CD80, CD83, CD86, and HLA-DR was up-regulated and addition of the 513 antibody, but not the control IgM, further increased the levels of CD83, CD86, and HLA-DR expression. These results indicated that activation of DDR1 by itself had a limited effect on DC maturation and was not competent to induce full maturation of DC, but rather further promoted phenotypic maturation of DC induced by TNF-α.

Activation of DDR1 Promotes Functional Maturation of DCs

The most important function of DCs is to present antigens to naïve T cells. To demonstrate that DDR1 activation contributes to the production of highly potent antigen-presenting mDCs, iDCs were incubated for 2 days in the presence or absence of TNF-α and/or LPS (inducers of DC maturation), either with or without the 513 antibody, and their capacity to present antigens by allogeneic MLR was measured. Human T cells were purified from PBMCs of healthy donors by magnetic separation using CD3+microbeads (Miltenyi Biotech Inc., Auburn, Calif.). T cells ($1 \times 10^5$) were placed in 96-well plates with increasing numbers of DC ($5 \times 10^2 - 1 \times 10^4$ cells) in 200 μl culture medium. On day four, 1 μCi/well of [$^3$H]

thymidine was added, and incorporation of radioactivity was measured after 15 hours of incubation. All tests were performed in triplicate.

Figure 9:
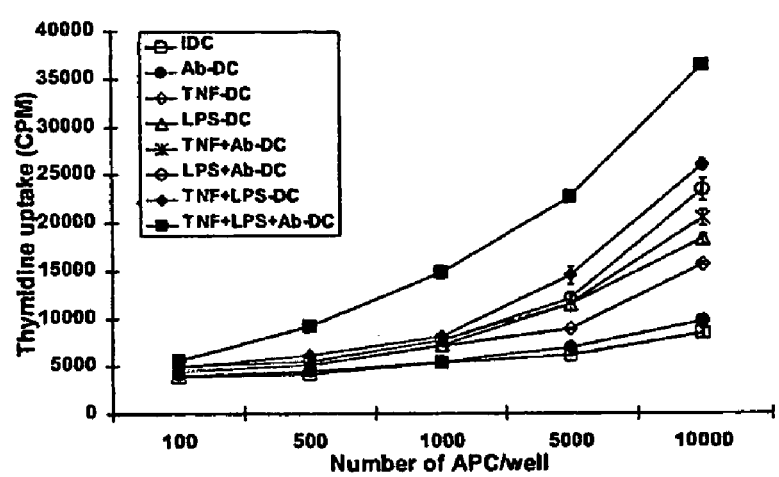
FIG. 9 is a graph showing the effect of DDR1 antibody on the antigen presenting capacity of DCs. DDR1 activation significantly up-regulated the antigen presenting capacity of tumor necrosis factor a (TNFα-), lipopolysaccharide (LPS-), and TNF-α plus LPS-induced mature DCs.

As shown in FIG. 9, immature (iDCs) showed only a weak activity to activate allogeneic MLR and activation of DDR1 with the 513 antibody had no effect. TNF-α- or LPS-induced mDCs markedly activated allogeneic MLR in a cell number-dependent manner. TNF-α plus LPS showed an additive effect. It was of great interest that activation of DDR1 significantly up-regulated antigen-presenting activity of TNF-α-, LPS-, and TNF-α plus LPS-induced mDCs. Thus, activation of DDR1 promotes functional maturation of DCs in combination with other DC maturation-inducing agents.

To further study the effect of DDR1 activation on the functional maturation of DCs, the release of IL-12, IL-10, and TNF-α was quantified. The concentrations of IL-10, IL-12, p70, and TNF-α were measured in the Lymphokine Testing Laboratory, Clinical Services Program, SAIC Frederick, Frederick, Md., with enzyme-linked immunosorbent assay (ELISA) kits (R&D Systems) specific for human IL-10, IL-12 p70 or TNF-α. The sensitivities of the assays were 5pg/ml for IL-10, 0.5 pg/ml for IL-12 p70 and 5 pg/ml for TNF-α. The release of IL-12 and TNF-α from LPS-induced mDCs was significantly up-regulated by activation of DDR1 ($P<0.001$); however, there was no difference in IL-10 release. Activation of iDC with the 513 antibody did not induce the release of either IL-12, IL-10, or TNF-α. (Statistical analyses were performed by Bonferroni/Dunn with One Way Factorical ANOVA.)

Activation of DDR1 Induces Autophosphorylation of DDR1 and the Recruitment of Shc To measure the kinetics of DDR1autophosphorylation, $1 \times 10^7$ iDC or TNF-α-induced mDCs were plated on dishes, serum-starved in RPMI 1640 containing 1% FCS for 10 hours, and subsequently activated with agonistic anti-DDR1 IgM (5 μg/ml) or control IgM (5 ug/ml) for varous times. Cell lysates were prepared, DDR1 was immunoprecipitated using anti-DDR1 Ab (C-20), and tyrosine-phosphorylation of DDR1 was analyzed by Western blotting using a mouse monoclonal anti-phosphotyrosine IgG and a sheep anti-mouse IgG coupled with horseradish peroxidase. Peroxidase activity was visualized by the Enhanced Chemiluminescence Detection System (Amersham).

In both iDCs and mDCs, autophosphorylation of DDR1 was detected at 30 minutes following activation and remained phosphorylated at 120, minutes. Treatment with control IgM did not induce autophosphorylation of DDR1 in either iDCs or mDCs.

In addition to tyrosine phosphorylated DDR1 another tyrosine phosphorylated protein was detected, whose molecular mass was approximately 46 kDa, 30 to 90 minutes after activation of DDR1. By Western blotting with an anti-Shc antibody, it was determined that this 46 kDa protein was Shc. The recruitment of Shc to DDR1b in DDR1b-expressing breast cancer cells or leukemic cell line THP-1 cells transduced to express DDR1b has been previously detected (Vogel et al., J. Biol. Chem. 175:5779-5784, 2000). The kinetics of Shc recruitment were also similar to that detected after activation of DDR1b overexpressed in THP-1 cells. Therefore, it is highly likely that the recruitment of Shc was via activation of DDR1b. The amounts of Shc co-immunoprecipitated from cell lysates of mDC were larger than that of iDCs. DDR1 remained phosphorylated at 8 hours following activation; however, the co-immunoprecititation of Shc was seen only between 30 and 90 minutes.

p38 MAP Kinase is a Target of DDR1 Signaling in DC

To detect phosphorylation of MAP kinases, ATF2, or MKK3/6, iDC and mDC were activated with agonistic 513 anti-DDR1 IgM or control IgM for varous times. Since TNF-α is known to activate p38 MAP kinase (Ono and Han, Cell. Signal. 12:1-13, 2000), cells were washed 6 times with PBS before activation in order to minimize the effect of TNF-α. Twenty μl of cell lysates were directly mixed with 20 μl of sample buffer and then analyzed.

p38 MAP kinase was phosphorylated 30 minutes after activation with the 513 antibody and remained phosphorylated after 120 minutes. The kinetics of p38 MAP kinase phosphorylation was similar to that of DDR1 autophosphorylation. The transcriptional factor ATF2, a substrate of p38 MAP kinase, was also phosphorylated with similar kinetics. Phosphorylation of p38 MAP kinase and ATF2 was also detected in TNF-a-induced mDCs with similar kinetics; however, the levels of phosphorylation were much greater in mDCs than in iDCs. In contrast to the 513 antibody, control IgM did not induce phosphorylation of p38 MAP kinase. Phosphorylation of other MAP kinases, such as ERK1, ERK2, or JNK, or MKK3/6, upstream kinase of p38 MAP kinase, were not detected in response to agonistic anti-DDR1 IgM, although they were rapidly activated in DCs in response to TNF-α stimulation.

DDR1-Mediated Phenotypic and Functional Maturation is Dependent on a p38 MAP Kinase Pathway To measure the involvement of the p38 MAP kinase pathway in DDR1-mediated up-regulation of CD80, CD83, CD86, and HLA-DR expression, iDC were pre-treated with a p38, MAP kinase inhibitor, SB203580. SB203580, almost completely inhibited the expression of CD80, CD83, CD86, and HLA-DR expression induced during TNF-α-induced DC maturation in the presence of either agonistic anti-DDR1 IgM or control IgM. Thus, both TNF-a-mediated and DDR1-mediated induction of CD80, CD83, CD86, and HLA-DR was dependent on the p38 MAP kinase pathway. The capacity to activate allogeneic MLR of TNF-α-induced DCs and its up-regulation by DDR1 activation were almost completely abrogated by SB203580. These results indicated that functional maturation of iDCs to mDCs were dependent on a p38 MAP kinase pathway.

Example 5

DDR1 is Inducible in Human Neutrophils and Plays a Role in the Production of MCP-1/CC-Chemokine Ligand 2 (CCL-2)

Reagents

A rabbit polyclonal antibody against human DDR1 (C-20) was obtained from Santa Cruz Biotechnology (Santa Cruz, Calif.). Phosphate buffered saline (PBS), RPMI 1640, recombinant protein G-agarose (PGA), and pre-cast tris-glysine SDS gel were from Invitrogen (Gaithersburg, Md.). Fetal calf serum (FCS) was from HyClone (Logan, Utah). Human serum, propidium iodide (PI), bovine collagen type I, and proteinase inhibitors were obtained from Sigma (St Louis, Mo.). Recombinant human TNFα (rTNFα) were from PeproTech (Rocky Hill, N.J.) and R&D Systems, Inc. (Minneapolis, Minn.). Recombinant GM-CSF, recombinant IFN-γ, neutralizing mouse monoclonal IgGs against human TNFα (clone 1825.121), GM-CSF (clone 3209.1), and IFN-γ (clone 25718.11) were obtained from R&D Systems. Dextran T-500 was from Pharmacia Biotech, Inc. (Piscataway, N.J.). Lymphoprep and Accu-Prep were from Accurate Chemical & Scientific Corp. (Westbury, N.Y.).

Preparation of Neutrophils

Human PMN and peripheral blood mononuclear cells (PBMC) were obtained from heparinized blood from human donors (10 units of heparin per ml of blood). One volume of 5% dextran (T-500 Pharmacia, Piscataway, N.J.) in phosphate buffered saline (PBS) was added to three volumes of blood in 50 ml polypropylene tubes. After a 40 minute incubation at room temperature, the leukocyte-rich plasma layer was removed and overlaid onto Lymphoprep in 50 ml tubes and the tubes were centrifuged at 800×g for 20 minutes at room temperature. PMN were separated from erythrocytes by lysis in 0.2% NaCl, washed in complete medium three times at 4° C. and resuspended in complete medium. PBMC contained in the PMN preparations obtained by this method were less than 0.5% by morphologic examination. Cell viability was higher than 98% by trypan blue staining.

IFN-γ and Collagen Synergize to Up-Regulate MCP-1 Production by Neutrophils

A panel of cytokines was previously tested for their ability to induce MCP-1 production in PMN and it was reported that TNF-α and IFN-γ could cooperate to induce a high level of MCP-1 production (Yamashiro et al., *J. Leukoc. Biol.* 69:698, 2001). To demonstrate whether the interaction of cytokine treated cells with collagen further augmented MCP-1 production, PMN were incubated on either uncoated or collagen-coated plates in the presence of different cytokines. There was no significant effect by collagen when no cytokine or TNF-α was added. As was previously observed, there was no significant MCP-1 release by IFN-γ treated cells. However, when the cells were incubated on collagen-coated plates with IFN-γ, there was a potent synergistic effect between these two stimuli. The majority of MCP-1 was released between 24 hours and 48 hours, showing a delayed kinetics of MCP-1 release. Collagen had no significant effect on GM-CSF-treated cells, but had a negative effect on cells treated with TNF-α plus IFN-γ or INF-α plus IFN-γ plus GM-CSF. The effect of IFN-γ was dose-dependent. As little as 0.8 U/ml (50 pg/ml) of IFN-γ and collagen up-regulated MCP-1 release.

IFN-γ Induces DDR1 Expression in Neutrophils

PMN were incubated in presence of IFN-γ or GM-CSF for 24 hours and the expression of cell-surface DDR1 was measured by flow cytometry using an antibody raised against the extracellular domain of the receptor. One hundred thousand cells were suspended in 50 µl of cold PBS containing 0.1% $NaN_3$, 10 ng/ml BSA and 200 µg/ml human IgG in a Falcon 2052, tube, and incubated for 10 minutes on ice. One µg of anti-DDR1 rabbit polyclonal antibody raised aginst the N-terminus of DDR1 (Transgenic, Inc., Kumamoto, Japan), or control mouse IgG was added to each tube and the cells were incubated for another 15 minutes on ice. The cells were washed with PBS, and then incubated with 1 µg of FITC-conjugated goat anti-mouse IgG for 15 minutes on ice. At the end of incubation, PI was added to each tube (100 µM). The cells were washed by PBS, and subsequently analyzed by using a FACS scan (Becton Dickinson). Dead cells, determined by the incorporation of PI, were gated out. Results were processed by using the Cellquest software (Becton Dickinson).

The anti-DDR1 antibody recognized cell-surface expression of DDR1 on DDR1a overexpressing THP-1 cells. Freshly isolated PMN did not express a significant level of DDR1. Incubation of cells in medium alone appeared to induce a very low level of DDR1. Addition of GM-CSF slightly increased the level of DDR1 expression. Interestingly, IFN-γ markedly increased the level of DDR1 expression. Addition of TNF-α almost completely inhibited the IFNγ-induced DDR1 expression.

The following Western blot method was used to detect DDR1a and DDR1b expression in neutrophils. One hundred million cells were lysed on ice for 20 minutes in a buffer containing 50 mM NaCl, 20 mM Tris-HCl, 50 mM sodium fluoride, 30 mM $Na_4P_2O_7$, 5 mM EGTA, 3 mM sodium orthovanadate, 1% Triton X-100, 1 mg/ml leupeptin, 1 mM PMSF, 1 mg/ml aprotinin, 1 mg/ml pepstatinA and 100 µM sodium orthovanadate treated with $H_2O_2$. The lysates were spun in a microcentrifuge for 20 minutes and the supernatants were collected. The samples were incubated with an approximately 20 µl packed volume of PGA for 1 hour at 4° C. After brief centrifugation, supernatants were collected, mixed with 1 µg/ml polyclonal anti-human DDR1 IgG, and incubated for 1 hour at 4° C. Twenty µl of PGS were then added and incubated for an additional hour. IgG coupled PGA were washed with the washing buffer containing 50 mM Hepes, 150 mM NaCl, 0.1% Triton X-100, 10% glycerol three times, and 20 µl double-strength sample buffer (20% glycerol, 6% SDS, 10% 2-mercaptoethanol) was added. The samples were boiled for 10 minutes. Eluted proteins were analyzed on 8% polyacrylamide gels by SDS-PAGE and transferred electrophoretically to nitrocellulose membranes at 150 mA for 1 hour by a semi-dry system. The membranes were incubated with either anti-DDR1a antibody or DDR1b (Sugen) rabbit IgG, followed by anti-rabbit IgG coupled with horseradish peroxidase. Peroxidase was visualized by the Enhanced Chemiluminescence Plus Detection System (Amersham Pharmacia Biotech). By Western blotting with an antibody specific for the DDR1a or DDR1b isoforms, the expression of both isoforms was detected.

Specific Activation of DDR1 in Combination with IFN-γ Induces MCP-1 Release

To confirm that activation of DDR1 was responsible for the increased release of MCP-1 by PMN treated with IFN-γ and collagen, 513 anti-DDR1 Ab was used instead of collagen. The concentrations of MCP-1 were measured in the Lymphokine Testing Laboratory, Clinical Services Program, SAIC-Frederick (Frederick, Md.) with an ELISA kit (R&D Systems) specific for human MCP-1.

PMN incubated with IFN-γ with the antibody, but not with a control IgM, displayed shape change and aggregation similar to that induced by the treatment with IFN-γ and collagen at 24 hours. By MCP-1 ELISA, high levels of MCP-1 were detected in the culture supernatants of cells treated with IFN-γ and the antibody. These levels were equivalent to the levels detected in the supernatants of cells treated with IFN-γ and collagen.

It will be apparent that the precise details of the methods or compositions described may be varied or modified without departing from the spirit of the described invention. We claim all such modifications and variations that fall within the scope and spirit of the claims below.

We claim:

1. A method of enhancing maturation of an immature macrophage or an immature dendritic cell that expresses Discoidin Domain Receptor 1 (DDR1), comprising:
contacting the immature macrophage or the immature dendritic cell with an effective amount of a DDR1-activating antibody that specifically binds DDR1 in the presence of a differentiation agent that comprises granulocyte-macrophage-colony stimulating factor (GM-CSF), interleukin-4 (IL-4), tumor necrosis factor-α (TNF-α), or a combination thereof, wherein the DDR1-activating antibody enhances the differentiation agent-mediated maturation of the immature macrophage or the immature dendritic cell,
thereby enhancing maturation of the immature macrophage or the immature dendritic cell that expresses DDR1.

2. The method of claim 1, further comprising contacting the immature macrophage or the immature dendritic cell that expresses DDR1 with an agent that up-regulates the expression of DDR1, wherein the agent that up-regulates DDR1 expression comprises interleukin-1β, lipopolysaccharide, phytohemagglutinin, fetal calf serum or a combination thereof.

3. The method of claim 1, wherein the antibody is a monoclonal antibody.

4. The method of claim 1, further comprising contacting the immature macrophage or the immature dendritic cell with a differentiation agent that enhances monocyte or dendritic cell maturation, wherein the differentiation agent comprises lipopolysaccharide, or phorbol 12-myristate 13-acetate, or a combination thereof.

5. The method of claim 1, wherein the immature macrophage or the immature dendritic cell is in vivo.

6. The method of claim 1, wherein the immature dendritic cell or the immature macrophage is in vitro.

7. A method for producing an antigen presenting macrophage or dendritic cell, comprising
contacting an immature macrophage or an immature dendritic cell with an agent that activates Discoidin Domain Receptor 1 (DDR1) in the presence of an antigen and a differentiation agent, wherein the differentiation agent comprises granulocyte-macrophage-colony stimulating factor (GM-CSF), interleukin-4 (IL-4), tumor necrosis factor-α (TNF-α), or a combination thereof, and wherein the DDR1-activating agent is a DDR1-activating antibody that specifically binds DDR1 and enhances the differentiation agent-mediated maturation of the immature macrophage or the immature dendritic cell,
thereby producing an antigen presenting mature dendritic cell or an antigen presenting macrophage.

8. The method of claim 7, wherein the antigen comprises a protein, a polypeptide, a polysaccharide, a DNA molecule, a RNA molecule, a whole cell lysate, an apoptotic cell, or any combination thereof.

9. The method of claim 7, wherein the antigen is a viral, bacterial or fungal antigen.

10. The method of claim 1, wherein contacting the immature macrophage or the immature dendritic cell with an effective amount of the DDR1-activating antibody activates intracellular signaling molecules.

11. The method of claim 10, wherein the activated intracellular signaling molecules comprise p38 MAP kinase or Shc.

12. The method of claim 1, wherein contacting the immature macrophage or the immature dendritic cell with an effective amount of the DDR1-activating antibody up-regulates the release of differentiation agent-mediated chemokines or cytokines from a mature macrophage or dendritic cell.

13. A method of enhancing maturation of an immature macrophage or an immature dendritic cell that expresses Discoidin Domain Receptor 1 (DDR1), comprising contacting the immature macrophage or the immature dendritic cell with an effective amount of
a DDR1-activating antibody that specifically binds DDR1 in the presence of
a differentiation agent that comprises granulocyte-macrophage-colony stimulating factor (GM-CSF), wherein the DDR1-activating antibody enhances the GM-CSF-mediated maturation of the immature macrophage or the immature dendritic cell, thereby inducing enhancing maturation of the immature macrophage or the immature dendritic cell that expresses DDR1.

14. The method of claim 13, further comprising contacting the immature macrophage or the immature dendritic cell that expresses DDR1 with an agent that up-regulates the expression of DDR1, wherein the agent that up-regulates DDR1 expression comprises tumor necrosis factor-α, interleukin-1β, lipopolysaccharide, phytohemagglutinin, fetal calf serum, or a combination thereof.

15. The method of claim 13, further comprising contacting the immature macrophage or the immature dendritic cell with a differentiation agent that enhances monocyte or dendritic cell maturation, wherein the differentiation agent comprises tumor necrosis factor-α, lipopolysaccharide, or a combination thereof.

16. The method of claim 13, wherein the antibody is a monoclonal antibody.

17. A method of enhancing maturation of an immature macrophage or an immature dendritic cell that expresses Discoidin Domain Receptor 1 (DDR1), comprising:
contacting the immature macrophage or the immature dendritic cell with an effective amount of a DDR1-activating antibody that specifically binds DDR1 in the presence of a differentiation agent that comprises granulocyte-macrophage-colony stimulating factor (GM-CSF), interleukin-4 (IL-4), and tumor necrosis factor-α (TNF-α), wherein the DDR1-activating antibody enhances the differentiation agent-mediated maturation of the immature macrophage or the immature dendritic cell, thereby enhancing maturation of the immature macrophage or the immature dendritic cell that expresses DDR1.

18. The method of claim 17, further comprising contacting the immature macrophage or the immature dendritic cell that expresses DDR1 with an agent that up-regulates the expression of DDR1, wherein the agent that up-regulates DDR1 expression comprises interleukin-1β, lipopolysaccharide, phytohemagglutinin, fetal calf serum, or a combination thereof.

19. The method of claim 17, further comprising contacting the immature macrophage or the immature dendritic cell with a differentiation agent that enhances monocyte or dendritic cell maturation, wherein the differentiation agent comprises tumor necrosis factor-α, lipopolysaccharide, or a combination thereof.

20. The method of claim 17, wherein the antibody is a monoclonal antibody.

21. A method of enhancing maturation of an immature macrophage or an immature dendritic cell that expresses Discoidin Domain Receptor 1 (DDR1), comprising:
contacting the immature macrophage or the immature dendritic cell with an effective amount of a DDR1-activating antibody that specifically binds DDR1 in the presence of a differentiation agent that comprises tumor necrosis factor-α (TNF-α), wherein the DDR1-activating antibody enhances the TNF-α-mediated maturation of the immature macrophage or the immature dendritic cell,
thereby enhancing maturation of the immature macrophage or the immature dendritic cell that expresses DDR1.

22. The method of claim 21, further comprising contacting the immature macrophage or the immature dendritic cell that expresses DDR1 with an agent that up-regulates the expression of DDR1, wherein the agent that up-regulates DDR1 expression comprises interleukin-1β, lipopolysaccharide, phytohemagglutinin, fetal calf serum, or a combination thereof.

23. The method of claim 21, further comprising contacting the immature macrophage or the immature dendritic cell with a differentiation agent that enhances monocyte or dendritic cell maturation, wherein the differentiation agent comprises lipopolysaccharide.

24. The method of claim 21, wherein the antibody is a monoclonal antibody.

25. The method of claim 7, wherein the differentiation agent comprises tumor necrosis factor-α (TNF-α).

26. The method of claim 25, further comprising contacting the immature macrophage or the immature dendritic cell with a differentiation agent that enhances monocyte or dendritic cell maturation, wherein the differentiation agent comprises lipopolysaccharide.

* * * * *

UNITED STATES PATENT AND TRADEMARK OFFICE
CERTIFICATE OF CORRECTION

| | |
|---|---|
| PATENT NO. | : 7,855,076 B2 |
| APPLICATION NO. | : 10/507385 |
| DATED | : December 21, 2010 |
| INVENTOR(S) | : Yoshimura et al. |

It is certified that error appears in the above-identified patent and that said Letters Patent is hereby corrected as shown below:

On the Title Page, Section (56) OTHER PUBLICATIONS:
    Page 1, right column, at Kamohara et al., "collage" should read --collagen--.
    Page 1, right column, at L' Hôte et al., "phsophorylation," should read --phosphorylation,--.

In the Specification:
    Column 1, line 57 "DDR1, appears" should read --DDR1 appears--.
    Column 1, line 59, "37," should read --37--.
    Column 1, line 66, "DDR1," should read --DDR1--.
    Column 2, line 2, "DDR1," should read --DDR1--.
    Column 2, line 4, "DDR1," should read --DDR1--.
    Column 2, line 10, "DDR1," should read --DDR1--.
    Column 2, line 11, "DDR1," should read --DDR1--.
    Column 2, line 18, "DDR1," should read --DDR1--.
    Column 2, line 26, "DDR1," should read --DDR1--.
    Column 2, line 33, "DDR1," should read --DDR1--.
    Column 2, line 36, "DDR1," should read --DDR1--.
    Column 2, line 40, "DDR1," should read --DDR1--.
    Column 2, line 42, "DDR1," should read --DDR1--.
    Column 2, line 43, "DDR1," should read --DDR1--.
    Column 2, lines 46-47, "denddritic" should read --dendritic--.
    Column 2, line 50, "DDR1," should read --DDR1--.
    Column 2, line 56, "contacting a" should read --contacting an--.
    Column 2, lines 56-57, "macrphage" should read --macrophage--.

Signed and Sealed this
Third Day of April, 2012

David J. Kappos
*Director of the United States Patent and Trademark Office*

Column 3, line 1, "IL-10,," should read --IL-10,--.

Column 3, line 4, "(MCP)-1,," should read --(MCP)-1,--.

Column 3, line 13, "MCP-1,," should read --MCP-1,--.

Column 3, line 18, "leukoctye." should read --leukocyte.--.

Column 3, line 30, "DDR1," should read --DDR1--.

Column 3, line 33, "DDR1 a-" should read --DDR1a- --.

Column 4, line 20, "(FIG. 6B)" should read --(FIG. 6C)--.

Column 4, line 29, "galactosidese," should read --galactosidase--.

Column 4, line 32, "manufacture's" should read --manufacturer's--.

Column 4, line 35, "presence of" should read --presence or--.

Column 4, lines 45-46, "galactosidese," should read --galactosidase--.

Column 4, line 48, "manufacture's" should read --manufacturer's--.

Column 4, line 51, "presence of" should read --presence or--.

Column 4, line 66, "a (TNFα-)," should read --α (TNFα),--.

Column 4, line 66, "(LPS-)" should read --(LPS)--.

Column 5, line 33, "probes" should read --probe--.

Column 5, line 35, "probes" should read --probe--.

Column 5, line 41, "1. Abbreviations" should read --I. Abbreviations--.

Column 6, line 52, "neutophil" should read --neutrophil--.

Column 7, line 26, "are not be" should read --are not--.

Column 7, line 40, "I, II, I, IV," should read --I, II, III, IV--.

Column 7, line 51, "principle" should read --principal--.

Column 7, line 59, "myleoid" should read --myeloid--.

Column 9, line 11, "37," should read --37--.

Column 9, line 40, "ineraction," should read --interaction,--.

Column 9, line 67, "included" should read --includes--.

Column 10, lines 46-47, "Arena viridae" should read --*Arenaviridae*--.

Column 10, line 48, "orbiviurses" should read --orbiviruses--.

Column 10, line 60, "Hepatitis C);" should read --Hepatitis C));--.

Column 10, lines 63-64, "such as. *M tuberculosis, M avium, M intracellulare,* and *M kansaii*" should read --such as *M. tuberculosis, M. avium, M. intracellulare,* and *M. kansasii*--.

Column 10, line 66, "*pyogeites*," should read --*pyogenes*--.

Column 10, line 67, "*agalactiae*," should read --*agalactiae*--.

Column 11, line 1, "*Streptococcus, (viridans,* group)." should read --*Streptococcus* (*viridans* group).--.

Column 11, lines 2-3, "*Streptococcus*, (*anaerobic*, sps.)." should read --*Streptococcus* (*anaerobic* sps.).--.

Column 11, line 3, "*pneuinoniae*," should read --*pneumoniae*,--.

Column 11, line 5, "*antracis*," should read --*anthracis*,--.

Column 11, lines 6-7, "*perfringers*," should read --*perfringens*,--.

Column 11, line 10, "*Leptospira*,." should read --*Leptospira*,--.

Column 13, line 21, "DDR" should read --DDR.--.

Column 13, line 35, "has" should read --have--.

Column 16, line 2, "umbillical" should read --umbilical--.

Column 16, line 12, "MW-1α." should read --MIP-1α.--.

Column 16, line 65, "DDR" should read --DDR1--.

Column 17, line 33, "U.S. Patent No. 5,994,126," should read --U.S. Patent No. 5,994,126--.

Column 17, line 60, "moncyte" should read --monocyte--.

Column 17, line 67, "AF353183," should read --AF353183);--.

Column 18, line 1, "can be a" should read --can be--.

Column 18, line 5, "in a mammalian cell systems," should read --in mammalian cell systems,--.

Column 18, line 23, "codon" should read --codon.--.

Column 18, line 28, "in are" should read --are--.

Column 19, line 66, "In a one" should read --In one--.

Column 20, line 2, "Among the specific" should read --The specific--.

Column 23, line 67, "leukoctye" should read --leukocyte--.

Column 24, line 1, "leukoctyes" should read --leukocytes--.

Column 24, line 33, "such as way" should read --such a way--.

Column 25, line 65, "DDR1," should read --DDR1--.

Column 26, line 20, "contacting a n" should read --contacting an--.

Column 27, line 16, "the an agent" should read --an agent--.

Column 27, line 42, "intramusclar," should read --intramuscular,--.

Column 27, line 42, "pareternal," should read --parenteral,--.

Column 28, line 2, "intraperitioneal," should read --intraperitoneal,--.

Column 28, line 14, "formuated" should read --formulated--.

Column 28, line 37, "(PAN)" should read --(PMN)--.

Column 28, line 59, "collage" should read --collagen--.

Column 30, line 34, "10," should read --10--.

Column 31, line 15, "withour" should read --without--.

CERTIFICATE OF CORRECTION (continued)
U.S. Pat. No. 7,855,076 B2

Column 33, line 36, "CO2" should read --$CO_2$--.

Column 34, line 26, "60," should read --60--.

Column 34, line 48, "TIP-1" should read --THP-1--.

Column 35, line 31, "tris-glysine" should read --tris-glycine--.

Column 36, line 2, "RMPI1640" should read --RPMI 1640--.

Column 36, line 16, "manufacture's" should read --manufacturer's--.

Column 36, line 30, "hour" should read --hours--.

Column 36, line 31, "hour" should read --hours--.

Column 36, line 56, "CD14 CD40," should read --CD14, CD40,--.

Column 37, line 18, "in cell of" should read --in cells of--.

Column 38, line 1, "cells" should read --cell--.

Column 38, line 22, "(294, bp)," should read --(294 bp),--.

Column 38, line 23, "20, cycles" should read --20 cycles--.

Column 38, line 44, "RMPI" should read --RPMI--.

Column 38, line 53, "Triton-X 10%" should read --Triton-X, 10%--.

Column 39, line 2, "2-mercaptetharol)" should read --2-mercaptoethanol)--.

Column 40, line 16, "TIP-1" should read --THP-1--.

Column 40, lines 20-21, "SB203580, the the MEK" should read --SB203580, the MEK--.

Column 40, line 37, "macrophages" should read --macrophages,--.

Column 41, line 43, "[α-$^{32}$P]dCTP" should read --[α-$^{32}$P]dATP--.

Column 41, line 50, "(Gaitherburg, Md.)." should read --(Gaithersburg, Md.)--.

Column 42, line 17, "5×10$^6$, cells/ml" should read --5×10$^6$ cells/ml--.

Column 42, line 40, "4, hours." should read --4 hours.--.

Column 43, line 5, "cytokine" should read --cytokines--.

Column 43, lines 9-10, "manufacture's" should read --manufacturer's--.

Column 43, line 32, "cells" should read --cell--.

Column 44, line 13, "varous" should read --various--.

Column 44, line 19, "$H_2O_2$" should read --$H_2O_2$.--.

Column 44, lines 39-40, "(5'-AGTTGAGGGGACTITC-CCAGGC-3')" should read --(5'-AGTTGAGGGGACTTTCCCAGGC-3')--.

Column 44, line 55, "PMN" should read --PMA--.

Column 45, line 3, "manufacture's" should read --manufacturer's--.

Column 45, line 6, "presence of" should read --presence or--.

Column 45, line 9, "manufacture's" should read --manufacturer's--.

Column 45, line 26, "DDR-1b-overexpresing" should read --DDR-1b-overexpressing--.

CERTIFICATE OF CORRECTION (continued)
U.S. Pat. No. 7,855,076 B2

Column 45, line 29, "SB203580," should read --SB203580--.

Column 45, line 36, "SB203580," should read --SB203580--.

Column 45, line 40, "SB203580," should read --SB203580--.

Column 46, lines 13-15, "L up-regulated" should read --LPS up-regulated--.

Column 46, line 32, "P38" should read --p38,--.

Column 46, line 47, "SB203580," should read --SB203580--.

Column 47, line 44, "20 MM" should read --20 mM--.

Column 48, line 38, "SB203580," should read --SB203580--.

Column 48, line 43, "CD83," should read --CD83--.

Column 48, line 43, "CD80," should read --CD80--.

Column 49, lines 16-17, "IL-12, p70" should read --IL-12 p70--.

Column 49, line 37, "varous" should read --various--.

Column 49, line 47, "120," should read --120--.

Column 49, line 66, "co-immunoprecititation" should read --co-immunoprecipitation--.

Column 50, line 4, "varous" should read --various--.

Column 50, line 17, "TNF-a-induced" should read --TNF-α-induced--.

Column 50, line 32, "p38," should read --p38--.

Column 50, line 32, "SB203580, almost" should read --SB203580 almost--.

Column 50, line 56, "tris-glysine" should read --tris-glycine--.

Column 51, line 40, "or INF-α" should read --or TNF-α--.

Column 51, line 51, "2052," should read --2052--.

Column 51, line 52, "aginst" should read --against--.

Column 52, line 4, "IFNγ-induced" should read --IFN-γ-induced--.

In the Claims:

Column 59, line 48, "thereby inducing enhancing" should read --thereby enhancing--.